United States Patent
Rousso et al.

(10) Patent No.: US 12,017,092 B2
(45) Date of Patent: Jun. 25, 2024

(54) APPARATUS AND METHOD FOR TREATING KIDNEYS

(71) Applicant: MDSG Innovation Ltd., Rehovot (IL)

(72) Inventors: Benny Rousso, Rishon-LeZion (IL); Lior Eshel, Rishon-LeZion (IL); Assaf Erell, Ramat-Gan (IL); Naama Winetraub, Holon (IL)

(73) Assignee: MDSG Innovation Ltd., Rehovot (IL)

( * ) Notice: Subject to any disclaimer, the term of this patent is extended or adjusted under 35 U.S.C. 154(b) by 577 days.

(21) Appl. No.: 16/500,451

(22) PCT Filed: Apr. 3, 2018

(86) PCT No.: PCT/IL2018/050397
§ 371 (c)(1),
(2) Date: Oct. 3, 2019

(87) PCT Pub. No.: WO2018/185767
PCT Pub. Date: Oct. 11, 2018

(65) Prior Publication Data
US 2020/0188696 A1    Jun. 18, 2020

Related U.S. Application Data

(60) Provisional application No. 62/480,707, filed on Apr. 3, 2017.

(51) Int. Cl.
*A61N 7/00*    (2006.01)
(52) U.S. Cl.
CPC ........ *A61N 7/00* (2013.01); *A61N 2007/0004* (2013.01); *A61N 2007/0043* (2013.01);
(Continued)
(58) Field of Classification Search
CPC ................ A61N 7/00; A61N 2007/004; A61N 2007/0043; A61N 2007/0047;
(Continued)

(56) References Cited

U.S. PATENT DOCUMENTS

| | | |
|---|---|---|
| 5,115,805 A | 5/1992 | Bommannan et al. |
| 6,251,088 B1 | 6/2001 | Kaufman et al. |

(Continued)

FOREIGN PATENT DOCUMENTS

| | | |
|---|---|---|
| EP | 0800788 | 10/1997 |
| WO | WO 01/52931 | 7/2001 |

(Continued)

OTHER PUBLICATIONS

Barasch and Ronco et al., (2012). NGAL Curve for the Early Diagnosis of AKI in Heart Failure Patients. In: Vincent, JL. (eds) Annual Update in Intensive Care and Emergency Medicine 2012. Annual Update in Intensive Care and Emergency Medicine, vol. 2012. Springer, Berlin, Heidelberg (Year: 2012).*

(Continued)

*Primary Examiner* — Boniface N Nganga

(57) ABSTRACT

A method and/or system are provided for improving kidney function and/or increasing Glomerular Filtration Rate (GFR) of the renal system, by applying acoustic and/or ultrasonic energy to one or more of the kidneys. The method suggests either focused or non-focused (or combined) energy delivery, optionally in a noninvasive approach, which could also be implemented invasively and/or by implantable device. Potential applications of this technique, include, but are not restricted to, treatment of renal disorders such as CKD (Chronic Kidney Disease) and/or AKI (Acute Kidney Injury), short term or long term intervention in kidney function for therapeutic or diagnostic purposes, modifying urine output in heart failure, modulating blood volume and/or pressure, and modulating clearance of compounds in the blood are typically difficult to extract from the kidneys, such as iodine, other imaging contrast media, and similar compounds.

57 Claims, 28 Drawing Sheets

(52) U.S. Cl.
CPC ............... *A61N 2007/0047* (2013.01); *A61N 2007/0052* (2013.01); *A61N 2007/0073* (2013.01); *A61N 2007/0078* (2013.01); *A61N 2007/0082* (2013.01)

(58) Field of Classification Search
CPC .... A61N 2007/0052; A61N 2007/0073; A61N 2007/0078
See application file for complete search history.

(56) References Cited

U.S. PATENT DOCUMENTS

| | | | |
|---|---|---|---|
| 7,653,438 | B2 | 1/2010 | Deem et al. |
| 8,382,672 | B2 | 2/2013 | Andrews |
| 8,585,597 | B2 | 11/2013 | Dae et al. |
| 8,845,629 | B2 | 9/2014 | Demarais et al. |
| 8,858,440 | B2 | 10/2014 | Tyler |
| 9,108,037 | B2 | 8/2015 | Sliwa et al. |
| 9,420,990 | B2 | 8/2016 | Dae et al. |
| 2003/0036697 | A1* | 2/2003 | Ottoboni ............ A61K 49/223 600/431 |
| 2004/0127793 | A1* | 7/2004 | Mendlein ............ A61B 8/4209 600/442 |
| 2004/0174772 | A1* | 9/2004 | Jones .................... G10K 11/02 367/152 |
| 2008/0045882 | A1 | 2/2008 | Finsterwald |
| 2009/0298047 | A1* | 12/2009 | Barasch ................ G01N 33/70 435/4 |
| 2011/0152986 | A1 | 6/2011 | Allen et al. |
| 2011/0208095 | A1 | 8/2011 | Jolesz et al. |
| 2011/0257561 | A1 | 10/2011 | Gertner et al. |
| 2012/0065552 | A1* | 3/2012 | Andrews ................ A61B 8/08 601/2 |
| 2012/0209118 | A1* | 8/2012 | Warnking ............ A61B 8/085 601/2 |
| 2013/0158385 | A1* | 6/2013 | Barnes ............... G01R 33/4814 600/411 |
| 2014/0194786 | A1 | 7/2014 | Gertner et al. |
| 2014/0200489 | A1* | 7/2014 | Behar .................... A61N 7/00 601/3 |
| 2014/0336665 | A1 | 11/2014 | Gavala et al. |
| 2015/0133950 | A1 | 5/2015 | Shelton et al. |
| 2016/0113699 | A1 | 4/2016 | Sverdlik et al. |
| 2017/0007853 | A1 | 1/2017 | Alford et al. |

FOREIGN PATENT DOCUMENTS

| | | | | |
|---|---|---|---|---|
| WO | | WO 02/24050 | | 3/2002 |
| WO | | WO 2004/075977 | | 9/2004 |
| WO | | WO-2013111136 A2 | * | 8/2013 ............ A61B 18/24 |
| WO | | WO-2018071908 A1 | * | 4/2018 ............ A61N 7/00 |
| WO | | WO 2018/185767 | | 10/2018 |

OTHER PUBLICATIONS

Supplementary European Search Report and the European Search Opinion dated Apr. 29, 2021 From the European Patent Office Re. Application No. 18780551.0. (14 Pages).

Supplementary Partial European Search Report and the European Provisional Opinion dated Dec. 21, 2020 From the European Patent Office Re. Application No. 18780551.0. (12 Pages).

International Preliminary Report on Patentability dated Oct. 17, 2019 From the International Bureau of WIPO Re. Application No. PCT/IL2018/050397. (11 Pages).

International Search Report and the Written Opinion dated Aug. 9, 2018 From the International Searching Authority Re. Application No. PCT/IL2018/050397. (17 Pages).

Fischer et al. "Renal Ultrafiltration Changes Induced by Focused US", Radiology, 253(3): 697-705, Dec. 2009.

Gigliotti et al. "Ultrasound Prevents Renal Ischemia-Reperfusion Injury by Stimulating the Splenic Cholinergic Anti-Inflammatory Pathway", Journal of the American Society of Nephrology, 24(9): 1451-1460, Published Online Aug. 1, 2013.

Khalid et al. "Kidney Ischaemia Reperfusion Injury in the Rat: The EGTI Scoring System as A Valid and Reliable Tool for Histological Assessment", Journal of Histology & Histopathology, 3(Art.1): 1-7, Jan. 4, 2016.

McDannold et al. "Blood-Brain Barrier Disruption Induced by Focused Ultrasound and Circulating Preformed Microbubbles Appears to Be Characterized by the Mechanical Index", Ultrasound in Medicine and Biology, 34(5): 834-840, May 2008.

Melnikov et al. "Neutrophil-Independent Mechanisms of Caspase-1- and IL-18-Mediated Ischemic Acute Tubular Necrosis in Mice", The Journal of Clinical Investigation, 110(8): 1083-1091, Oct. 2002.

Miloradovic et al. "Vibroacustic Microvibrations Enhance Kidney Blood Supply, Glomerular Filtration and Glutathione Peroxidase Activity in Spontaneously Hypertensive Rats", General Physiology and Biophysics, 34(1): 89-94, Jan. 2015.

Shankar et al. "Potential Adverse Ultrasound-Related Biological Effects. A Critical Review", Anesthesiology, 115(5): 1109-1124, Nov. 2011.

Tanaka et al. "Nonpharmacological, Biomechanical Approaches to Control Inflammation in Acute Kidney Injury", Nephron, 137(4): 277-281, Published Online Jun. 9, 2017.

Whalen et al. "A Novel Rodent Model of Severe Renal Ischemia Reperfusion Injury", Renal Failure, 38(10): 1694-1701, Published Online Feb. 12, 2016.

Yang et al. "Focused Ultrasound-Modulated Glomerular Ultrafiltration Assessed by Functional Changes in Renal Arteries", PLOSONE, 8(1): e54034-1-e54034-6, Jan. 10, 2013.

* cited by examiner

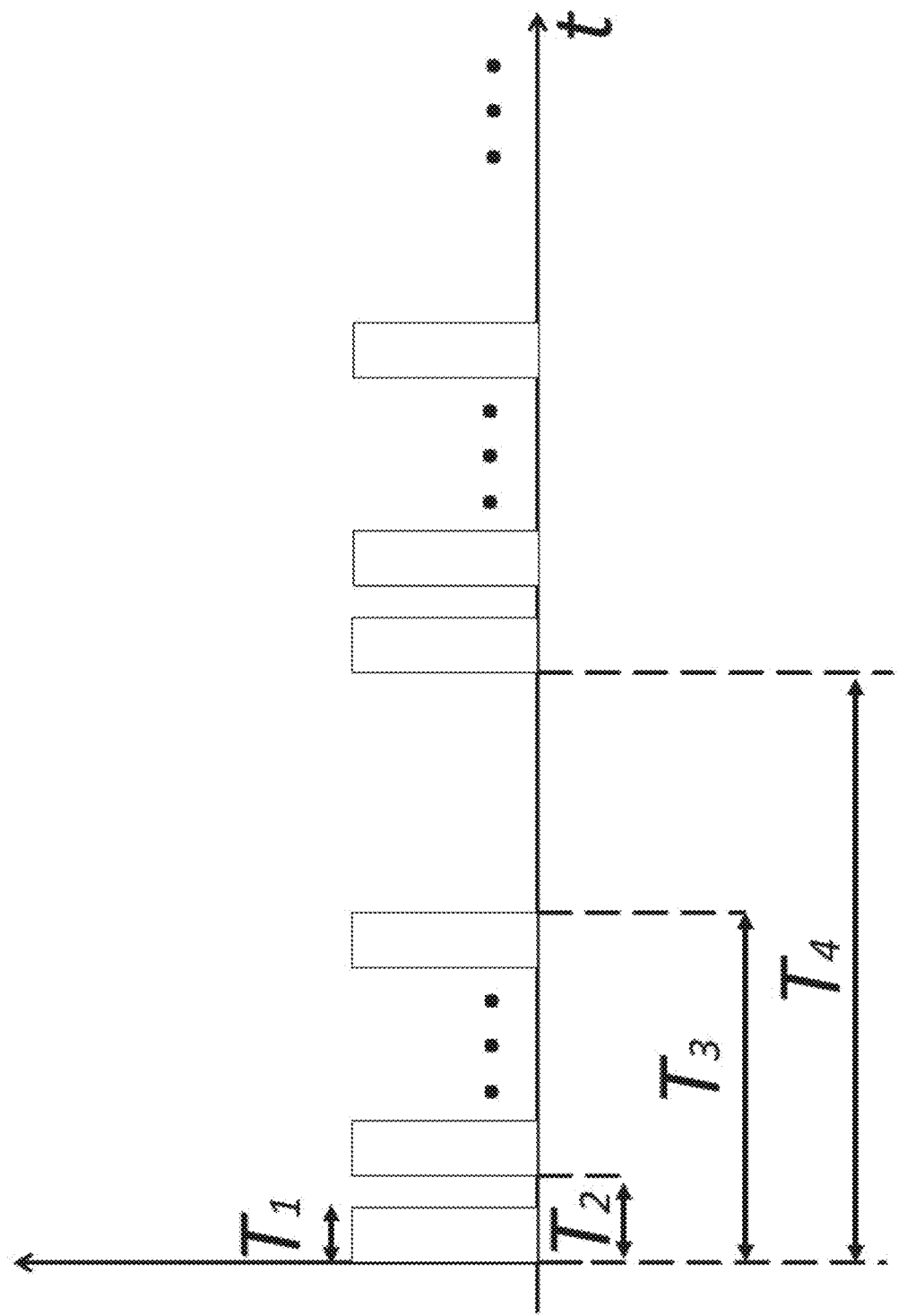

APPARATUS AND METHOD FOR TREATING KIDNEYS

RELATED APPLICATIONS

This application is a National Phase of PCT Patent Application No. PCT/IL2018/050397 having International filing date of Apr. 3, 2018, which claims the benefit of priority under 35 USC § 119(e) of U.S. Provisional Patent Application No. 62/480,707 filed on Apr. 3 2017. The contents of the above applications are all incorporated by reference as if fully set forth herein in their entirety.

FIELD AND BACKGROUND OF THE INVENTION

The kidneys include a complex collection of microstructures that co-function, which include, among others, the nephron as a whole, and sub-components such as glomeruli, Bowmen capsule, tubule, loop of Henle, collection duct, blood vessels and capillaries, nephrons, etc. The kidneys' Glomerulus, is a network of small blood vessels (e.g., capillaries)—that acts as a barrier between blood and urine, and performs the first filtration stage of blood, by mechanisms of diffusion and osmosis. In some of patients with renal disorders, the renal filtration process is impaired causing a variety of illnesses. The quality of renal filtration is commonly estimated by the Glomerular Filtration Rate GFR measure or similar estimates. Additionally, the collection duct system of the kidney includes tubule and ducts, which participate and control electrolytes and fluid balance, by reabsorption and excretion. Various clinical conditions and disorders are categorized as pre-renal, intrinsic and post-renal, depending on the stage in the filtration and reuptake processes they relate to. Some of the function or disorders are associated with blood flow (From the heart and through the renal artery and capillaries), blood pulsatility, and pressure gradients, whether systemically or locally. Some of the function or disorders are associated with the various control and feedback mechanisms of the kidney—whether of homeostasis, or concentration balances, hormonal feedback or of neuronal feedback. Some of the function or disorders are associated with the tubular structure, tubular damage, tubular regeneration, epithelial cells detaching from tubular wall, protein casts formation. Some of the function or disorders are associated with infection of other nephron-toxic conditions. Among the post-renal disorders, some are associated with blockade, kidney stones formation and infection. Some disorders are related to sepsis, to toxins affecting the kidney, to allergies and inflammatory processes, to proteins accumulated in the glomerular region or the tubular region, to sclerosis of the capillaries and to endothelial damage.

In most cases, treatment of chronic kidney disorders is based on reduction of risk factors for chronic conditions (e.g. reduction of glucose, lipids, sodium, etc.) and in maintaining volume, blood pressure and cardiac output, but not in pathways that recover the kidney itself. The use of diuretics and ACE-inhibitors affect kidney function, but normally in the context of balancing the cardiovascular system and not for the purpose of recovery of the kidney itself.

Historically, ultrasound was used for imaging tissue at very low intensities and short duration, and alternatively, it was used for treatment by very high intensities for achieving tissue ablation (by High Intensity Focused Ultrasound, HIFU) or breaking kidney stones (lithotripsy). These therapies achieve damage to the tissue and the stones and are associated with generation of high degree of thermal damage and cavitation damage, at the focused target area, but often also to some extent in the vicinity—in surrounding healthy tissue of the kidney and neighboring organs. While ultrasound is being used to treat a disorder, they are usually associated with major side effects that reduce to some extent the kidney function. All these imaging techniques and treatment techniques are commonly used for short term, in procedures that span over several minutes.

Several published studies have explored potential impact of ultrasound on tissue, and an important extensive summary of such potential aspects was published in "Potential Adverse Ultrasound-related Biological Effects: A Critical Review", Anesthesiology 11 2011, Vol. 115, 1109-1124. Some studies (e.g. "Vibroacustic microvibrations enhance kidney blood supply, glomerular filtration and glutathione peroxidase activity in spontaneously hypertensive rats", Gen. Physiol. Biophys. (2015), 34, 89-94) looked at microvibrations at frequencies of a few Hz (e.g. 7 Hz or 30 Hz) and up to several KHz (e.g. 4.51 (Hz) to observe changes, but these are possibly less likely to have meaningful effect on renal system in clinical use due to one or more of the following or other reasons: limit on power to avoid the disturbing sound that is produced, and predominantly due to the non-specific nature of the energy in this frequency range to any target tissue or mechanism, and lack of ability to focus any such energy on a desired target region (the wavelength is far greater than any possible focusing on a desired region), thus could be prone to side effects on other tissue, safety aspects or alternatively too low energy to obtain any clinically meaningful benefit. Some studies (e.g. "Renal Ultrafiltration Changes Induced by Focused US", Radiology, Volume 253: Number 3—December 2009) attempted to use higher frequencies, in the range of about 260 KHz and focused ultrasound, however, they required addition of contrast agent (microbubbles) to observe any effect—and with that become non useful for clinical applications, both because the use of microbubbles is invasive and complex and irrelevant for chronic use, and because this type of frequency and microbubbles generate cavitation, which has negative safety implication on the tissue.

U.S. Pat. No. 8,382,672B2 discloses "devices, systems, and methods treatment of patients can be used to help mitigate injury to the kidneys by applying cyclical mechanical pressure energy at low intensities. The energy often be selectively directed from non-invasive transducers disposed outside the patients. The energy will typically comprise low frequency ultrasound energy, shock wave energy, or the like, and may induce the generation and/or release of nitric oxide, thereby enhancing perfusion and ameliorating tissue damage. Superimposed micro and macro duty cycles may help avoid thermal and other injury to tissues of the patient during treatment. Bilateral treatments are facilitated by a support structure that orients at least one transducer toward each kidney".

Patent application US20110152986A1 discloses "a therapeutic device for relieving an affected organ or part of the body comprises a mass of material such as beeswax which in use is capable of maintaining a temperature range of 36 to 38 degrees Celsius at the affected part of the body when retained on the skin near the affected part. The invention also extends to articles of apparel containing such a therapeutic device".

SUMMARY OF THE INVENTION

According to an aspect of some embodiments of the present invention there is provided a method of modifying kidney activity, comprising: irradiating at least a portion of a kidney by applying to the kidney ultrasonic energy at a frequency, repetition rate and amplitude suitable to affect kidney function; repeating said irradiating until said affect kidney function is achieved.

According to some embodiments of the invention, said frequency is higher than 5 Megahertz (MHZ).

According to some embodiments of the invention, said irradiating comprises irradiating at a main frequency selected to have a wavelength of a size or harmonic of a kidney structure to be affected.

According to some embodiments of the invention, said amplitude is from about 0.1 microsecond to about 100 microseconds.

According to some embodiments of the invention, said irradiating is performed for a period of time from about 1 hour to about 24 hours.

According to some embodiments of the invention, said irradiating is performed intermittently.

According to some embodiments of the invention, said applying is from outside the body.

According to some embodiments of the invention, said applying is from inside the body by means of an implantable device.

According to some embodiments of the invention, said applying is from inside the body by means of an endoscopy device.

According to some embodiments of the invention, said affected kidney function comprises filtration.

According to some embodiments of the invention, said affected kidney function comprises an increase in glomerular filtration rate.

According to some embodiments of the invention, said affected kidney function comprises reuptake by a tubular structure.

According to some embodiments of the invention, said affected kidney function comprises blood pressure control.

According to some embodiments of the invention, said systolic blood pressure is reduced by at least 5% for at least 10 minutes.

According to some embodiments of the invention, said affected kidney function comprises metabolic activity.

According to some embodiments of the invention, the rate of creation of at least one metabolite is changed by at least 10% on the average for 10 minutes.

According to some embodiments of the invention, said affected kidney function comprises hormone secretion.

According to some embodiments of the invention, said affected kidney function comprises excretion of contrast material.

According to some embodiments of the invention, said contrast material is a contrast material injected during imaging procedure.

According to some embodiments of the invention, contrast material comprises iodine.

According to some embodiments of the invention, at least 10% of said contrast material is secreted into the urine during up to 24 hours from when said irradiating starts.

According to some embodiments of the invention, at least 50% of said contrast material is secreted into the urine during up to 24 hours from when said irradiating starts.

According to some embodiments of the invention, at least 50% of said contrast material is secreted into the urine during up to 4 hours from when said irradiation starts.

According to some embodiments of the invention, a degree of kidney dysfunction caused by contrast material is reduced by at least 10%, as measured after 24 hours.

According to some embodiments of the invention, irradiating comprises avoiding causing damage by said irradiating.

According to some embodiments of the invention, avoiding comprises avoiding thermal damage.

According to some embodiments of the invention, comprises avoiding heating kidney tissue by more than 5 degrees Celsius.

According to some embodiments of the invention, comprising avoiding heating kidney tissue by more than 3 degrees Celsius.

According to some embodiments of the invention, comprising pausing during said irradiating to allow heat transfer away from said irradiated kidney portion.

According to some embodiments of the invention, avoiding comprises irradiating while avoiding cavitation.

According to some embodiments of the invention, comprising sensing and modifying said irradiating based on said sensing.

According to some embodiments of the invention, said sensing comprises sensing a negative effect of said irradiating.

According to some embodiments of the invention, sensing comprises sending one or more of increase in blood pressure, increase in heart rate, pain indicators, protein in urine, heat using a heat sensitive imaging sequence and cavitation by ultrasound reflection.

According to some embodiments of the invention, said irradiating comprises irradiating to have an immediate effect on said kidney function.

According to some embodiments of the invention, said irradiating comprises irradiating to have an effect on said kidney function during said irradiating.

According to some embodiments of the invention, said irradiating comprises irradiating to have an effect on said kidney function at 24 hours after irradiating is stopped.

According to some embodiments of the invention, said irradiation directly affects glomerular networks of the kidney.

According to some embodiments of the invention, said irradiation directly affects mechanosensors of the kidney.

According to some embodiments of the invention, said irradiation directly affects nerves of the kidney.

According to some embodiments of the invention, said irradiation directly affects semi-permeable membranes of the kidney.

According to some embodiments of the invention, said irradiation irradiating over a period of less than 24 hours, followed by a non-irradiating period of at least 24 hours.

According to some embodiments of the invention, said irradiation is synchronized to a physiological measurement.

According to some embodiments of the invention, said irradiation is synchronized to a cardiac cycle.

According to some embodiments of the invention, said irradiation is synchronized to a cardiac systole.

According to some embodiments of the invention, said irradiation is synchronized to a cardiac diastole.

According to some embodiments of the invention, said irradiation is synchronized to an arrival of a pulse wave to a part of said kidney.

According to some embodiments of the invention, said irradiation is synchronized to a change in blood flow to an irradiated kidney.

According to some embodiments of the invention, said irradiation comprises continuous wave radiation.

According to some embodiments of the invention, said irradiation comprises pulsed irradiation.

According to some embodiments of the invention, irradiation has a repetition rate selected to have effect on nerve tissue.

According to some embodiments of the invention, said irradiation comprises bursts of irradiation applied at a rate between 20 and 200 Hz.

According to some embodiments of the invention, said irradiation comprises bursts of irradiation applied at a rate between 50 and 120 Hz.

According to some embodiments of the invention, said irradiation has at least one of a waveform and a repetition rate selected to have effect on endothelial tissue in the kidney.

According to some embodiments of the invention, said irradiation has a burst duration and intra-burst delay selected to allow tissue cooling of the irradiated tissue.

According to some embodiments of the invention, said irradiation comprises not irradiating in the presence of ultrasound contrast material in the kidney.

According to some embodiments of the invention, said irradiation comprises not irradiating in the presence of micro bubbles in the kidney.

According to some embodiments of the invention, irradiation assists in transport across a kidney membrane.

According to some embodiments of the invention, said irradiation assists in clearing microscopic blockage from a kidney membrane.

According to some embodiments of the invention, said irradiation comprises depositing at least 75% of the energy within a volume of the kidney.

According to some embodiments of the invention, said irradiation comprises delivering an energy density outside of the kidney that is less than 50% of a deposition level inside the kidney.

According to an aspect of some embodiments of the present invention there is provided an apparatus for treating a kidney configured to deliver ultrasonic radiation to at least one kidney following at least one protocol to perform a suitable waveform and power and duration causing said ultrasonic radiation to positively affect kidney function.

According to some embodiments of the invention, the apparatus comprises: at least one transducer suitable to deliver ultrasonic radiation to a kidney; and circuitry for powering said at least one transducer with said suitable waveform and power and duration causing said ultrasonic radiation to positively affect kidney function.

According to some embodiments of the invention, the apparatus comprises at least one sensor and wherein said circuitry modifies said powering according to a signal from said sensor.

According to some embodiments of the invention, said at least one transducer comprises a plurality of flexibly interconnected transducers.

According to some embodiments of the invention, said at least one transducer comprises a phased array.

According to some embodiments of the invention, said at least one transducer comprises a beam-forming transducer.

According to some embodiments of the invention, said apparatus is implantable in the body of the user.

According to some embodiments of the invention, said at least one transducer is incorporated in an endoscopy device.

Some examples of some embodiments of the invention are described below, noting that implementations can include features form one or more of these example embodiments.

Example 1

A method of modifying kidney activity, comprising: irradiating at least a portion of a kidney by applying to the kidney ultrasonic energy at a magnitude and frequency suitable to affect kidney function or other renal system function.

Example 2

A method according to example 1, wherein said applying is from outside the body.

Example 3

A method according to example 1, wherein said affected kidney function comprises filtration.

Example 4

A method according to example 3, wherein said effect comprises an increase in glomerular filtration rate.

Example 5

A method according of example 3, wherein following irradiating for at least 10 minutes including any intra-irradiation pauses, said filtration is increased by at least 10% on the average for a period of at least 10 minutes.

Example 6

A method according of example 3, wherein following starting said irradiating, filtration is immediately increased by at least 10% on the average for a period of at least 10 minutes.

Example 7

A method according to example 1, wherein said affected kidney function comprises reuptake by a tubular structure.

Example 8

A method according to example 7, wherein following irradiating for at least 10 minutes said reuptake is increased by at least 10% on the average for at least 10 minutes.

Example 9

A method according to example 7, wherein said reuptake is immediately increased by at least 10% on the average for at least 10 minutes.

Example 10

A method according to example 1, wherein said affected kidney function comprises blood pressure control.

Example 11

A method according to example 10, wherein systolic blood pressure is reduced by at least 5% for at least 10 minutes.

Example 12

A method according to example 10, wherein said applying is for cumulative duration of at least one hour every day, and systolic blood pressure is reduced by at least 5% for at least during said at least one hour relative to the average level in the hour preceding said one hour.

Example 13

A method according to example 1, wherein said affected kidney function comprises metabolic activity.

Example 14

A method according to example 13, wherein the rate of creation of at least one metabolite is changed by at least 10% on the average for 10 minutes.

Example 15

A method according to example 1, wherein said affected kidney function comprises hormone secretion.

Example 16

A method according to example 13, wherein the rate of hormone secretion of at least one hormone is changed by at least 10% on the average for 10 minutes.

Example 17

A method according to example 1, wherein said affected kidney function comprises contrast material handling.

Example 18

A method according to example 17, wherein said contrast material is a contrast material injected during imaging procedure.

Example 19

A method according to example 17, wherein said contrast material comprises iodine.

Example 20

A method according to example 17, wherein at least 10% of said contrast material is secreted into the urine during up to 24 hours from when said irradiating starts.

Example 21

A method according to example 17, wherein at least 50% of said contrast material is secreted into the urine during up to 24 hours from when said irradiating starts.

Example 22

A method according to example 17, wherein at least 50% of said contrast material is secreted into the urine during up to 4 hours from when said irradiation starts.

Example 23

A method according to example 17, wherein a degree of kidney dysfunction caused by contrast material is reduced by at least 10%, as measured after 24 hours.

Example 24

A method according to any of the preceding examples, wherein irradiating comprises avoiding causing damage by said irradiating.

Example 25

A method according to example 24, wherein avoiding comprises avoiding thermal damage.

Example 26

A method according to example 24, comprising avoiding heating kidney tissue by more than 5 degrees Celsius.

Example 27

A method according to example 24, comprising avoiding heating kidney tissue by more than 3 degrees Celsius.

Example 28

A method according to any of examples 24-27, comprising pausing during said irradiating to allow heat transfer away from said irradiated kidney portion.

Example 29

A method according to any of examples 24-28, wherein avoiding comprises irradiating while avoiding cavitation.

Example 30

A method according to any of the preceding examples, comprising sensing and modifying said irradiating based on said sensing.

Example 31

A method according to example 30, wherein said sensing comprises sensing a negative effect of said irradiating.

Example 32

A method according to example 31, wherein sensing comprises sending one or more of increase in blood pressure, increase in heart rate, pain indicators, protein in urine, heat using a heat sensitive imaging sequence and cavitation by ultrasound reflection.

Example 33

A method according to any of the preceding examples, wherein said irradiating comprises irradiating to have an immediate effect on said kidney function.

Example 34

A method according to any of the preceding examples, wherein said irradiating comprises irradiating to have an effect on said kidney function during said irradiating.

Example 35

A method according to any of the preceding examples, wherein said irradiating comprises irradiating to have an effect on said kidney function at 24 hours after irradiating is stopped.

Example 36

A method according to any of the preceding examples, wherein said irradiation directly affects glomerular networks of the kidney.

Example 37

A method according to any of the preceding examples, wherein said irradiation directly affects mechanosensors of the kidney.

Example 38

A method according to any of the preceding examples, wherein said irradiation directly affects nerves of the kidney.

Example 39

A method according to any of the preceding examples, wherein said irradiation directly affects semi-permeable membranes of the kidney.

Example 40

A method according to any of the preceding examples, wherein said irradiation irradiating over a period of less than 24 hours, followed by a non-irradiating period of at least 24 hours.

Example 41

A method according to any of the preceding examples, wherein said irradiation irradiating over a period of more than 24 hours.

Example 42

A method according to any of the preceding examples, wherein said irradiation is synchronized to a physiological measurement.

Example 43

A method according to example 42, wherein said irradiation is synchronized to a cardiac cycle.

Example 44

A method according to example 43, wherein said irradiation is synchronized to a cardiac systole.

Example 45

A method according to example 43, wherein said irradiation is synchronized to a cardiac diastole.

Example 46

A method according to example 43, wherein said irradiation is synchronized to an arrival of a pulse wave to a part of said kidney.

Example 47

A method according to example 42, wherein said irradiation is synchronized to a change in blood flow to an irradiated kidney.

Example 48

A method according to any of the preceding examples, wherein said irradiation comprises continuous wave radiation.

Example 49

A method according to any of the preceding examples, wherein said irradiation comprises pulsed irradiation.

Example 50

A method according to example 1, wherein said irradiation has a main frequency selected to have a wavelength of a size or harmonic of a kidney structure to be affected.

Example 51

A method according to example 50, wherein said main frequency is greater than 5 MHz.

Example 52

A method according to example 50, wherein said main frequency is between 8 and 20 MHz.

Example 53

A method according to example 50, wherein said main frequency is between 10 and 15 MHz.

Example 54

A method according to example 49 or example 50, wherein said irradiation has a repetition rate selected to have effect on nerve tissue.

Example 55

A method according to example 54, wherein said irradiation comprises bursts of irradiation applied at a rate between 20 and 200 Hz.

Example 56

A method according to example 54, wherein said irradiation comprises bursts of irradiation applied at a rate between 50 and 120 Hz.

Example 57

A method according to any of examples 49-56, wherein said irradiation has at least one of a waveform and a repetition rate selected to have effect on endothelial tissue in the kidney.

Example 58

A method according to any of examples 49-54, wherein said irradiation has a burst duration and intra-burst delay selected to allow tissue cooling of the irradiated tissue.

Example 59

A method according to any of the preceding examples, wherein said irradiation comprises not irradiating in the presence of ultrasound contrast material in the kidney.

Example 60

A method according to example 59, wherein said irradiation comprises not irradiating in the presence of micro bubbles in the kidney.

Example 61

A method according to example 59, wherein said irradiation assists in transport across a kidney membrane.

Example 62

A method according to example 59, wherein said irradiation assists in clearing microscopic blockage from a kidney membrane.

Example 63

A method according to any of the preceding examples, wherein said irradiation comprises depositing at least 75% of the energy within a volume of the kidney.

Example 64

A method according to any of the preceding examples, wherein said irradiation comprises delivering an energy density outside of the kidney that is less than 50% of a deposition level inside the kidney.

Example 65

Apparatus for treating a kidney, comprising: at least one transducer suitable to deliver ultrasonic radiation from outside a body to a kidney; and circuitry for powering said at least one transducer with a suitable waveform and power and duration causing said ultrasonic radiation to positively affect kidney function.

Example 66

Apparatus according to example 65, comprising at least one sensor and wherein said circuitry modifies said powering according to a signal from said sensor.

Example 67

Apparatus according to example 65 or example 66, wherein said at least one transducer comprises a plurality of flexibly interconnected transducers.

Example 68

Apparatus according to any of examples 65-67, wherein said at least one transducer comprises a phased array.

Example 69

Apparatus according to any of examples 65-68, wherein said at least one transducer comprises a beam-forming transducer.

Example 70

Apparatus according to any of examples 65-69, wherein said circuitry is configured to carry out the method of any of examples 1-63.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product.

Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as radiation control, might be expected to use completely different methods, e.g., making use of expert knowledge and/or the pattern recognition capabilities of the human brain, which would be vastly more efficient than manually going through the steps of the methods described herein.

The scope of the present invention includes embodiments described in the articles and patent publications cited in the Background of the Invention of this application. Any embodiment, technique and apparatus described in one or more of such references are combined with the techniques and apparatus described herein, and form an exemplary embodiment of the present invention.

All values, durations, frequencies, amplitudes, doses and dose ranges given in this application are for a typical adult human having a typical body mass of between about 50 and about 90 kg. For children, or underweight or overweight adults, the values may be used as described (e.g. frequencies, durations) or may be adjusted (e.g. doses and power—for as long as within safe ranges and limits on the Mechanical Index (MI) and Thermal Index for soft tissue (TIS) values, and possibly frequencies—if needed to adapt for depth of tissue) appropriately, as known by those skilled in the art.

It will be appreciated by persons skilled in the art that the present invention is not limited to what has been particularly shown and described hereinabove. Rather, the scope of the present invention includes both combinations and sub-combinations of the various features, parameters, described hereinabove, as well as variations and modifications thereof that are not in the prior art, which would occur to persons skilled in the art upon reading the foregoing description.

Similarly, each of the energy parameters, probe structure, beam forming, mechanical structures and mechanisms, algorithms, decision processes, circuits, treatment protocols, triggering events for initiating treatment, sensors, transducers, duration of treatments, location of treatment, feedback mechanisms, clinical conditions, clinical risk factors, measured parameters, clinical endpoints, methods, devices and/or others that are described in any of the sections, paragraphs, drawings, experiments, results and/or background may be combined with others that are described in any one or more of the other sections, paragraphs, drawings, experiments, results and/or background, and form an exemplary embodiment of the present invention.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 8 is a schematic representation of an example of the digital signal, in accordance with some embodiments of the invention;

Figure 1:
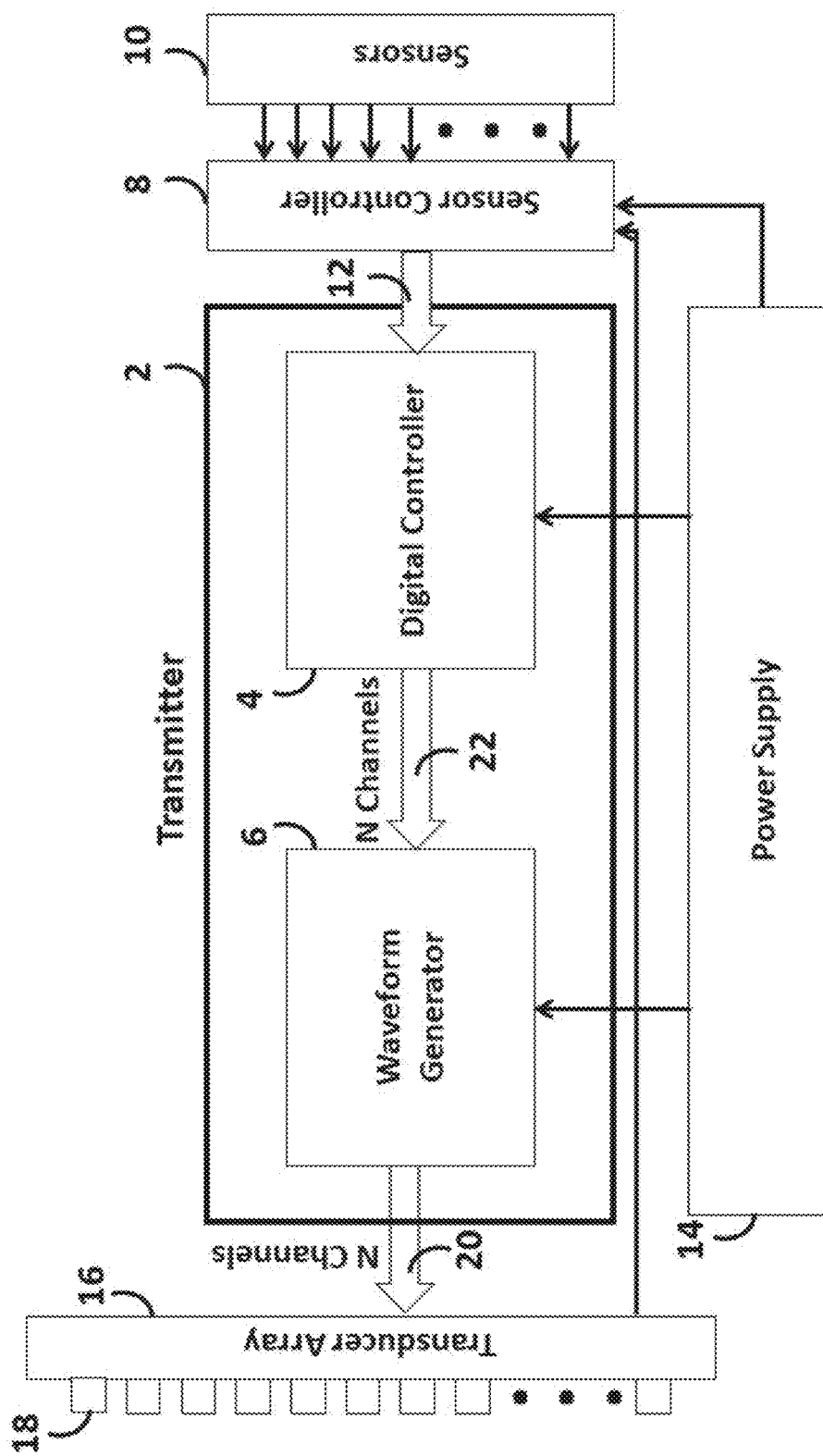
FIG. 1 is a schematic representation of an example of an embodiment of the device, in accordance with some embodiments of the invention.

DESCRIPTION OF SPECIFIC EMBODIMENTS
OF THE INVENTION

Overview

A broad aspect of some embodiments of the present invention relates to modifying renal function in a subject by emitting ultra sound radiation to the kidneys.

In some embodiments, the renal function is modified before and/or after the subject shows any renal dysfunction. In some embodiments, the renal function is modified as treatment when the subject presents acute renal failure. In some embodiments, the renal function is modified as treatment when the subject presents chronic renal failure.

In some embodiments, the renal function is modified before and/or during and/or after the subject is subjected to a medical intervention.

In some embodiments, the renal function is modified from outside the subject's body. In some embodiments, the renal function is modified from inside the subject's body.

In some embodiments, the renal function is modified for prolonged periods, for example from about 10 hours to about 24 hours. In some embodiments, affecting the renal function is performed for short periods, for example from about 1 hour to about 5 hours. In some embodiments, affecting the renal function is performed for intermittent periods, for example for a few hours, then stop for another few hours, then commencing again for another few hours.

In some embodiments, the renal function is modified while the subject is mobile. In some embodiments, renal function is modified while the subject is on bed rest.

In some embodiments, the renal function is modified by affecting the kidney's organelles and/or glomerulus and/or the circle of Henle and/or the Bowmen region and/or tubular and/or capillary blood vessels in the kidney's area.

In some embodiments, the renal function is modified by using acoustic signals.

In some embodiments, the renal function modification do not induce thermal or cavitation side effects.

In some embodiments, the renal function is modified by a device that emits acoustic signals.

In some embodiments, the device is a wearable device. In some embodiments, the device is incorporated in furniture.

In some embodiments, the device is incorporated to a catheter. In some embodiments, the device is implanted in the body of the subject.

In some embodiments, the frequency has a beam dimension, for example, from about 1 to about 100 micrometers, from about 100 to about 1000 micrometers, from about 50 to about 500 micrometers.

In some embodiments, the acoustic signals affecting the renal function have frequencies above 5 megahertz (MHz). In an embodiment, the acoustic signals affecting the renal function have frequencies from about 4 to about 7 MHz. In some embodiments, the acoustic signals affecting the renal function have frequencies from about 5 to about 10 MHz. In some embodiments, the acoustic signals affecting the renal function have frequencies from about 7 to about 13 MHz. In some embodiments, the acoustic signals affecting the renal function have frequencies from about 10 to about 50 MHz.

In some embodiments, affecting the renal function is performed in a focused manner (localized area) in the kidney. In some embodiments, affecting the renal function is performed in a wide manner (wide general area) of the kidney.

An aspect of some embodiments of the present invention relates to the use of ultrasonic radiation for the treatment of kidney deficiencies. In some embodiments, the kidney deficiency is acute kidney injury (AKI). In some embodiments, the kidney deficiency is chronic kidney disease (CKD). In some embodiments, the kidney deficiency is or contrast-induced nephropathy (CIN).

An aspect of some embodiments of the present invention relates to assisting in the regeneration of kidney tissues.

In some embodiments, providing assistance in the regeneration is done before and/or during and/or after a potential kidney damaging event.

In some embodiments, the potential kidney damaging event is ischemia and/or low blood pressure in anesthesia and/or low blood flow in anesthesia and/or injection of contrast material and/or sepsis and/or heart problems and/or hemorrhagic shock and/or liver failure and/or chronic kidney disease (CKD) and/or acute kidney injury (AKI) and/or acute tubular necrosis (ATN) and/or contrast-induced nephropathy (CIN).

An aspect of some embodiments of the present invention relates to providing protection to the kidney tissues, before and/or during and/or after a potential kidney damaging event by ultrasound radiation of the kidneys.

An aspect of some embodiments of the present invention relates to providing a treatment for improving renal function and/or assist with renal tissue regeneration and/or provide protection to the kidney from damage, by using ultrasound radiation, where the ultrasound radiation do not provide and/or is configured to not be a thermal treatment.

This invention, in some embodiments thereof, optionally provides a method and a system for improving renal function, assist with regeneration, improve recovery, treatment of AKI, protection in the presence of a stress e.g. ischemia or low blood pressure/flow in anesthesia, by treating using ultrasonic radiation on the kidneys. In some embodiments, the invention optionally provides a method and a system for improving renal function, by treating using ultrasonic radiation on the kidney's organelles. In some embodiments, the invention optionally provides a method and a system for improving renal function, by treating using ultrasonic radiation on the glomerulus and/or tubular and/or capillary blood vessels and/or the loop of Henle and/or the Bowmen capsule, in the kidney's area, with frequency components suitable to obtain a change in their function, and without a need for any high power, thermal effect or cavitation damage, or any contrast medium or other ultrasound absorbing material. In an exemplary embodiment, the predominant frequency ranges used for obtaining the desired effect are above 500 KHz, for example, in the range of above 1 MHz, optionally most of the energy is to be delivered to the tissue in the range of 2-25 MHz, optionally for resonating with glomeruli and/or Bowmen capsule and/or tubule and/or loop of Henle and/or collection duct and/or blood vessels and/or capillaries and/or nephrons, and optionally even higher frequencies for interacting with the same, for example most of the energy to be delivered in frequencies of about 4 MHz and up to 100 MHz. Optionally, the application ranges are in the ranges of >6 MHz, or for example 5-20 MHz, for example 5-15 MHz, or 1-12 MHz, or 10-15 MHz. In some exemplary embodiments of the invention, the application is by irradiation with ultrasound from outside the body.

It is noted that the approaches documented in the literature did not use or envision low-intensity ultrasound applied on its own to the tissue for prolonged periods (e.g., 1-24 hours, 1-8 days, 1-6 weeks, 1-10 months or longer or intermediate or shorter periods), as may be provided with some embodiments of the invention.

In some exemplary embodiments, the application of ultrasound irradiation is in configurations, methods, devices, waveforms, intensities, frequencies and/or control mechanisms which exploit the mechanism of action and design that are related directly to the function of glomeruli and/or Bowmen capsule and/or tubule and/or loop of Henle and/or collection duct and/or blood vessels and/or capillaries and/or nephrons.

In some exemplary embodiments, the energy deposited is aimed to be deposited mainly in kidney tissue (e.g., wholly within the kidney or within 1 cm of the kidney). Optionally, at least 30%, 50%, 75% or intermediate percentages of the energy are deposited in the kidney and/or the kidney achieves energy concentrations of at least a factor of 2 over nearby tissue.

In some embodiments, the energy is delivered in a focused manner, or to a wide area of the kidney, or by scanning multiple regions, or by parallel applying to multiple focused locations, or combinations thereof. In an example, scanning uses electrically controlled beam forming, e.g. by phased array of signals delivered concurrently using multiple transducers, or by a mechanical scanning, or by multiple independently transmitting transducers, or by multiple transducers, each with its own beam and waveforms, delivered at sequentially to different regions of the target organ, and/or combinations thereof.

In an exemplary embodiment, the system provides a semi-continuous waveform of energy, or a continuous waveform of energy, or a sequence of pulses or signals. In an example, the energy control if configured to generate an acoustic effect with each signal, pulse and/or burst having a maximal mechanical index lower than 1.9, for example, lower than 1.5, or lower than 1, or lower than 0.7, or lower than 0.5, or lower than 0.3. In an example of the present invention, the energy control is configured to generate an acoustic effect without generating any excessive heating in any tissue, such excessive heating is defined by a temperature change of no more than 10 degrees Celsius (deg C.), or preferably no more than 6 deg C., preferably no more than 4 deg C., or preferably no more than 2 deg C., or no more than 1 deg C. In some embodiments, during treatment application, an elevation in the temperature of the site of radiation is no higher than 2 degrees Celsius over the present temperature of the site at the moment of the treatment. In some embodiments, during treatment application, an elevation in the temperature of the site of radiation is no higher than 1 degree Celsius over the present temperature of the site at the moment of the treatment. In some embodiments, during treatment application, no elevation and/or unnoticeable change and/or non-significant change in the temperature of the site of radiation is detected and/or induced over the present temperature of the site at the moment of the treatment. In an exemplary embodiment, the thermal index is lower than 6, for example, lower than 4, or lower than 2. In an example of the present invention, the average emitted acoustic power is lower than 20 Watts, preferably lower than 10 Watts, for example in the range of 0.05 to 5 Watts, for example in the range of 0.5-3 Watts, for example about 1-2 Watts.

In some embodiments, the treatment for improving renal function and/or assist with renal tissue regeneration and/or provide protection to the kidney from damage, by using ultrasound radiation, do not provide and/or is configured to not be a thermal treatment.

In an exemplary embodiment, the energy is provided by one or more sequences of multiple signals, each having a single or multiple pulses or spikes, at one or more frequencies, and/or with sinusoidal or other shape, and/or with a sweep over several frequencies, and/or as chirp signal. In an example, each such signal is configured not to exceed the mechanical index threshold, and the repetition rates are designed not to exceed the thermal index threshold.

In some embodiments, the duration of each signal is continuous—e.g., if very low signal power is used, or by short signals, for example, each can be typically up to 5 seconds (sec), preferably shorter than 1 second, for example, shorter than 0.1 sec, for example shorter than 0.05 sec, for example, shorter than 1 msec or intermediate in length or longer. In an exemplary embodiment, with higher signal amplitude and mechanical index close to but lower than the maximal mechanical index, a signal duration of 10 milliseconds (msec) or shorter may be used, for example up to 1 msec, or shorter than 0.1 msec, for example up to about 50 micro sec, or up to about 10 microseconds, or shorter, or intermediate in length or longer. In some embodiments, continuous wave and/or duty cycle greater than 50% is implemented, with overall power not to exceed heating limitations.

In some embodiments, the repetition rates of the signals is set to potentially interact with timing properties that typically characterize stretch receptors response and/or cycles of autonomous sympathetic or para-sympathetic response, for example between 10 Hz and 200 Hz, for example between 30 Hz to 120 Hz, for example between 50-100 Hz, for example about 80 Hz. In some embodiments, the repetition rate can be higher, for example between 1 KHz and 100 KHz, for example between 5 KHz and 20 KHz, for example about 10 KHz. In an example, a sweep over multiple repetition rates, either selected once, or continuously through a range, or randomly within a range can be used, or combinations thereof.

In some embodiments, the systems include one or more sensors for or is configured to receive a sensor signal indicative of a physiological measure, for example, one or more of blood pressure, its cycles, or the heart rate, either mechanically or by ECG or by imaging, or by ultrasound or by sound, or by light emission or reflection, or similarly. In some embodiments, the system times the delivery of the acoustic signals to the systolic phase and/or to the diastolic phase and/or to an intermediate phase of the cardiac cycle or of the arterial blood pressure cycle, to achieve efficiency or to avoid capillary damage. In some embodiments, the system delivers the signals not synchronized to the cardiac cycle or to the arterial blood pressure cycle. In some embodiments, the system delivers the signals in an anti-synchronized manner to the cardiac cycle or to the arterial blood pressure cycle.

In some embodiments, the system comprises one or more cavitation sensors or receive information indicative of cavitation that evaluates the cavitation threshold near the one or more transducers, and/or at different tissue locations (e.g., in kidney or other tissue). In some embodiments, the system adjusts the signal amplitude, main frequencies, and/or duration to avoid cavitation, for example by keeping the signal amplitude, main frequencies, and/or duration at less than 0.9 or less than 0.5 or less than 0.3 or less than 0.1 or less than 0.05 of the values that could be identified as potentially causing cavitation.

In some embodiments, optionally in order to avoid long term cumulative heat, for example if proximity to bones is suspected, the energy may be applied as bursts of signals, in a total duration of a certain length, with relaxation time between bursts to ensure no excessive heat is accumulated. For example, a burst duration, after which a relaxation time is applied, can be of about 0.1 sec, or about 1 sec, or about 5 sec or shorter, intermediate or longer durations. In an exemplary embodiment burst duration can be selected in a range within 0.01 sec to 60 sec, or within 1 and 10 sec or shorter or longer or intermediate length durations. In an exemplary embodiment of the present invention, the relaxation time between bursts is set to be greater than 0.1 sec, for example greater than 1 sec, or greater than 5 sec or intermediate times. In an example, the duty cycle, being the ratio between burst duration to the total of burst duration and relaxation time (the repetition duration) is set to be about 0.1 or about 0.5 or between 0.01 to 0.8 or greater or shorter duty cycles. In some embodiments, it is calculated so that the thermal index, taking into account the signal energy, signal duration, repetitions of the signal within a burst, burst duration and relaxation time shall not exceed 6.0, or for example lower than 4, or lower than 2 or lower than 1.

In some embodiments, the system comprises one or more temperature sensors (e.g., by analyzing temperature sensitive imaging sequences, such as MRI or ultrasound imaging sequences) or receive information indicative of temperature, that evaluates the temperature changes and threshold near the one or more transducers, and/or at different tissue locations. In some embodiments, the system adjusts the signal amplitude, main frequencies, and/or duration and/or duty cycles and/or repetition rates, and/or burst duration, to avoid heating accumulation beyond a certain predefined level, for example by keeping the energy delivery parameters at less than 0.9 or less than 0.5 or less than 0.3 or less than 0.1 or less than 0.05 (or intermediate values) of the values that could be identified as potentially causing undesired heating. In some embodiments, the sensors are implanted sensors in the body of the subject.

In an exemplary embodiment, multiple transducers are configured to focus on a sonicated region having up to K times effective regional overlap (e.g., between 1 and 100, for example, between 3 and 20). In an exemplary embodiment, such transducers are timed not to deliver the signals simultaneously, thus keeping the mechanical index limit, or have overlapping delivery time thus adjust the signal properties to lower mechanical index so that the cumulative mechanical index is not exceeding the desired threshold. In an example embodiment, the repetition rates and burst durations are set to limits to produce K-times lower thermal index from each transducer, thus not exceeding the cumulative thermal index.

In an exemplary embodiment, the irradiated ultrasonic signal that is applied in each signal delivery comprises one or more of a spike, sine, chirp and/or combinations thereof. In an example, the signal duration is in the order of magnitude of 0.1, 1, 10, or 100 microsec. In an example, a burst comprises a sequence of signals, for example at about 20 Hz, 50 Hz, 80 Hz, 100 Hz, or 120 Hz, or in a range between these values, or lower or higher rates. In some embodiments, the sequence of signals may be at a rate of about 1 KHz, 5 KHz, 10 KHz, 20 KHz, 50 KHz, or in a range between these values or lower or higher rates. In an example, signal delivery and/or burst delivery is timed to systole/diastole/other phase of the blood pressure, or not synchronized with it. In an example, burst duration is selected to be, for example, about 0.1 sec, 1 sec, 5 sec, or 10 sec, or a duration between these values.

In an exemplary embodiment, one or more of the transducers has flat or rounded shape, determining the energy focusing of the interface facing the body. In some embodiments, the shape of each transducer is configured to form a narrow beam having an effective focal region at a depth within the body between about 1 and 20 centimeters (cm), for example depth between about 2 and 7 cm, for example between about 3 and 5 cm. In an example, the device includes several configurations of transducers that can be selected or interchanged, for different depth of focusing in the body, for example, a configuration for about 1-3 cm depth, a configuration for about 2-4 cm depth, a configuration about 3-6 cm depth, and a configuration for about 4-7 cm depth. In an example, for effective use with the high frequency range of above 5 Mhz (for example 10-15 MHz), such depth of focusing is associated with the use of multiple transducers, each having a diameter of less than about 2 cm, for example less than 1.5 cm, for example less than 1 cm, preferably less than 0.7 cm, for example, about 1, 2, or 5 mm.

In some embodiments, multiple small transducers are placed in a containing structure mounted next to the skin, preferably with an acoustic coupling element facing a kidney, each transducer having less than 1 cm diameter, each having a narrow beam, operating in frequencies of above 5 MHz, each having a target depth in the range of 2 to 6 cm are used. In another example, a phase array is used, for example with 30-300 transducers, to scan a region, having narrow beams formed for a peak at a distance of about 2 to 6 cm, and the beams are electrically controlled to scan the kidney region.

In some embodiments, the dimension of the narrow beam is, for example, from about 1 micrometer to about 100 micrometers. In some embodiments, the dimension of the narrow beam is, for example, from about 50 micrometers to about 500 micrometers. In some embodiments, the dimension of the narrow beam is, for example, from about 100 micrometers to about 1000 micrometers.

In an exemplary embodiment, the system is integrated with an imaging system, optionally the kidney location and boundaries are identified on the imaging system and the energy is delivered within the target area identified by or on the imaging system. In an exemplary embodiment of the present invention, the imaging is ultrasonic imaging. In an example of the present invention, 2D and/or 3D ultrasonic imaging transducers are used for delivering the energy with the control circuitry and/or software configured to deliver energy according to the parameters, setting, algorithms and thresholds defined in the present invention. In an example of the present invention, the same ultrasonic transducers are used for both imaging of the kidney and for delivering the energy to the kidney. In some embodiments, the imaging system detects the kidney using a reference model of the shape of the kidney. In some embodiments, the imaging system detects the boundaries or parts of the kidney, it matches them to the model, and utilizes this information to assist in defining the location of other tissues in the kidney and/or in the vicinity of the kidney. In some embodiments, the information of the location of other tissues in the kidney and/or in the vicinity of the kidney is used for the activation and/or deactivation of the device in the specific locations.

In an exemplary embodiment, an elastic and/or stiff interfacing material is used for coupling the transducers to the skin. In an exemplary embodiment of the present invention, the coupling material includes a container filled with fluids and/or the coupling material is made of gel with acoustic impedance and acoustic speed similar to that of water and/or skin and/or other body tissue. In an exemplary embodiment of the present invention, the transducer and/or the belt and/or the holding structure (e.g. in bed-mounted device) has a slot for inserting the coupling material and for holding it with good contact to the transducer and to the skin of the patient. In an exemplary embodiment of the present invention, the coupling material is exchangeable and disposable, thus maintaining clean surface and reuse of the belt and transducers (between days on same patient or among patients) while keeping hygienic device and skin contact.

In an exemplary embodiment, the acoustic/ultrasonic energy source is mounted over the patient around the pelvis, possibly using a belt, a sticker or other attachment means. In an example, the device is battery operated, with a controller mounted within or on or nearby the belt, and one or more transducers placed adjacent to one or more kidneys. In an exemplary configuration it can be used daily, during day time or during night time or both, it can be used while the patient is mobile, or as a bedside device, or part of a supporting structure integrative with the bed, or as part of a chair or sofa. In some embodiments the system and method are adapted for use in a clinic, and in some embodiments the system and method are adapted for use at home. In some embodiments the system and methods are for use by an operator and in some embodiments the system and methods are adapted to be operated by the patient. In some embodiments the system and methods are for use when the patient is under anesthesia, sedation or loss of consciousness or stabilized or immobilized, and in some embodiments the system and methods are adapted to be use on/by a patient that is awake, conscious, mobile or ambulatory. In an exemplary embodiment it can be used as a device mounted on and/or integrated into a bed during intensive care, or a regular hospitalization bed, or as part of the bed supporting a patient in an operation room or in a catheterization room or at home. Alternatively or additionally, it can be integrated into an invasive device and/or an implantable device for chronic treatment. Optionally, the device is programmed and/or otherwise configured for one or more of these uses.

In exemplary embodiment, the treatment is applied for several minutes, for example from about 30 minutes to about 270 minutes, (e.g. for improved clearance of fluids and/or of compounds from the blood, for example during heart failure treatment for improving fluids exertion or as an add-on to diuretics and/or during catheterization with contrast media for improving clearance of the contrast media and/or iodine and/or other high viscous material which is otherwise not well cleared from the kidney and cause kidney damage), hours, for example from about 2 hours to about 48 hours, (e.g. during treatment of heart failure or AKI or other acute renal failure situations, or abnormal blood pressure levels), intermittently for a few hours once a day or once in several days, for example 2-4 hours a day once a day or more times a day, (e.g. in treatment of CKD or abnormal blood pressure levels), over several days, weeks or in other chronic settings. This treatment can be used to potentially delay the deterioration process that leads to dialysis or kidney transplant, and/or it can be used as an add-on treatment to dialysis. In some exemplary embodiments, the system is integrated with a dialysis system. In some exemplary embodiments, the system implements similar ultrasonic energy to enhance the ex-vivo filtration processes implemented as part of the dialysis system (on the tubes, on the membranes and/or other components of the dialysis system), for example, with frequencies that are adapted for the tubes dimensions, and/or adapted to the membrane pores dimensions, and/or that are similar to those implemented in the body as described in the present invention, and/or in other frequencies, and/or combinations thereof. In some embodiments, the system is activated at the same time as the dialysis, while in some other embodiments the system is activated at times between dialysis, and in some other embodiments the system is activated intermittently during the dialysis, and in some other embodiments the system is activated with partial overlap with the time of dialysis, and in some embodiments the system is activated at a delay from the start or end of the dialysis. In some exemplary embodiments, the system is used in conjunction in-vivo peritoneal dialysis, wherein in some embodiments the system delivers the energy to the kidneys while in some other embodiments the system delivers the energy to the belly, to affect the filtration and osmosis processes in the peritoneum, and in some embodiments the energy is delivered to both the kidneys and the peritoneum.

In some embodiments, the invention provides a method and a system for prevention and/or amelioration of development of one of renal damage, for example including, any of ATN (acute tubular necrosis), AKI (acute kidney injury), CIN (contrast induced nephropathy), acute renal failure, acute renal dysfunction.

In some embodiments, the invention optionally provides a method and a system for the treatment of renal damage, including, for example, any of ATN (acute tubular necrosis), AKI (acute kidney injury), CIN (contrast induced nephropathy), acute renal failure, and acute renal dysfunction.

In some embodiments, the invention optionally provides a method and a system for the treatment of CKD (chronic renal disorder).

In some embodiments, the invention optionally provides a method and a system for acute improvement of renal function.

In some embodiments, the invention optionally provides a method and a system for chronic improvement of renal function.

In some embodiments, the invention optionally provides a method and a system for the improvement of regeneration processes of the renal system (post injury, or in general).

In some embodiments, the invention optionally provides a method and a system for the reduction of protein casts in the renal system (e.g.: in the tubules). In some embodiments, the invention optionally provides a method and a system for the reduction in damage of glomeruli and/or Bowmen capsule and/or tubule and/or loop of Henle and/or collection duct and/or blood vessels and/or capillaries and/or nephrons. In some embodiments, the invention optionally provides a method and a system for the reduction in tubular damage. In some embodiments, the invention optionally provides a method and a system for the reduction in blood (serum) Creatinine. In some embodiments, the invention optionally provides a method and a system for the improvement in Glomerular filtration rate. In some embodiments, the invention optionally provides a method and a system for the improvement in Creatinine clearance. In some embodiments, the invention optionally provides a method and a system for the improvement in renal output/urine output/urine flow rate. In some embodiments, the invention optionally provides a method and a system for the improvement in contrast media clearance by the kidney (e.g.: iodine/iohexol).

In some embodiments, the invention optionally provides a method and a system for the improvement of any of the abovementioned situations in a safe manner, and/or without causing any substantial acute or chronic damage and/or without causing substantial elevation in Urine Protein/Creatinine ratio and/or without causing any substantial thermal or cavitation damage and/or without need for using any microbubbles for increasing the impact of the ultrasonic energy, without utilizing heat as the predominant mean for generating the desired effect.

Exemplary Device

In some embodiments, the described techniques are applied in practice by a device or devices, which generate ultrasonic vibrations at a subject's kidneys. In some embodiments, the devices have several different mechanical configurations (described below), but, in some embodiments, the devices share a similar electronic system.

In some embodiments, the electronic system is, as schematically disclosed, for example, in FIG. 1. In some embodiments, the main component of the electrical part of the device is the transmitter 2. In some embodiments, the transmitter 2 comprises a digital controller 4 and a waveform generator 6. In some embodiments, the electronic system comprises a sensor controller 8 which receives measurements from a set of sensors 10, and sends command data to the digital controller 4, over a digital interface 12. In some embodiments, a power supply unit 14 which provides power to the different components of the device. In some embodiments, the transmitter 2 provides electrical input to N transducers 18 of a Transducer Array 16 through N channels 20.

In some embodiments, the electronic system is composed of at least one part. In some embodiments, the electronic system is composed of at least two parts. In some embodiments, the parts are either identical or different from each other. In some embodiments, each part is targeted at one of the two kidneys.

Exemplary Transducer Array

Figure 2:
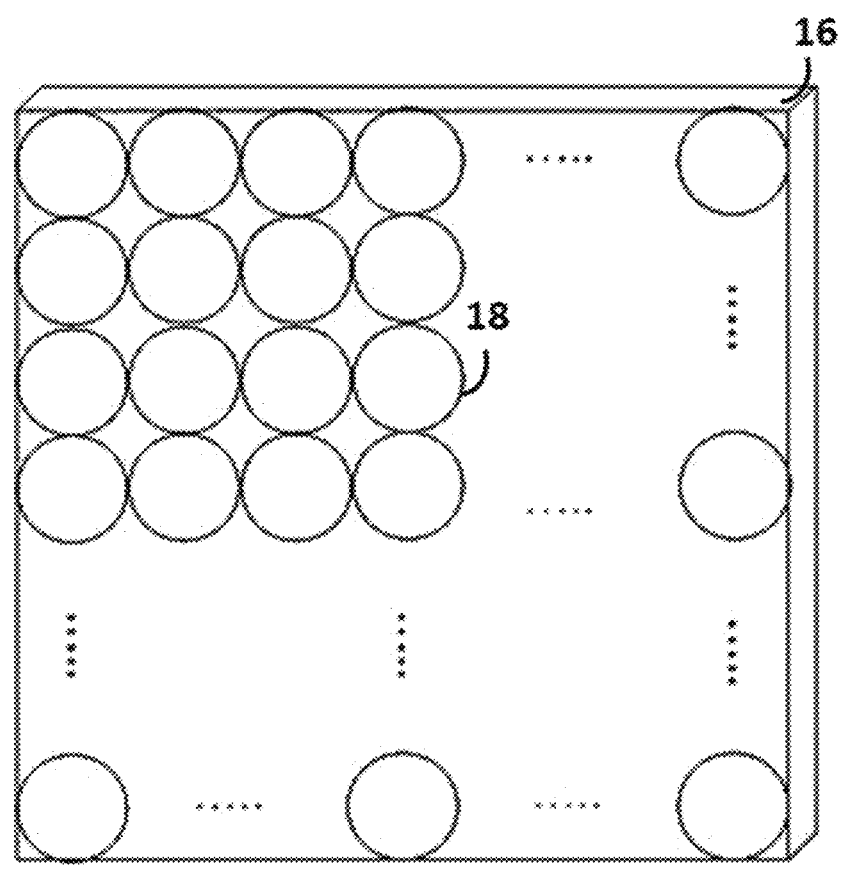
FIG. 2 is a schematic representation of an example of an embodiment of a transducer array, in accordance with some embodiments of the invention.

In some embodiments, the transducer array 16 is composed of a single transducer element. In some embodiments, the transducer array 16 is composed of multiple transducers arranged in a row (1 dimensional). In some embodiments, the transducer array 16 is composed of a grid (2 dimensional). Optionally, the transducer array is an array of N transducers, which may be arranged in 2-dimensional rectangular form as depicted in the example in FIG. 2—in front view.

In some embodiments, the transducer array is a non-phased array, which comprises a single-element probe (monolithic probe), which emits a beam in a fixed direction. In some embodiments, the transducer array is a phased array, comprising multiple element probes, by which the beam can be focused and swept electronically without moving the probes.

In some embodiments, the transducer array 16 may also act as a receiving element (connected and processed to/by the sensor controller 8), picking up reflected ultrasonic waves and using them to form an image or other types of information. In some embodiments, this information includes: estimation of distance to the kidney, Doppler effect flow velocities within the sonicated space, organ edge detection, automatic organ classification, detection of gas/air pockets in different organs (e.g. intestine, stomach), detection of lack of proper coupling between the transducer array and the patient's skin, renal artery blood flow imager or tracker, image stabilization/tracker that traces fiduciary/reference points in the body and/or placed on the body.

In some embodiments, the transducer array 16 is housed in a chamber connected by a cable to the other elements of the device.

In some embodiments, the chamber is stiff. In some embodiments, the chamber is flexible. In some embodiments, the chamber is shaped in different forms (e.g.: cylinder, a flat disc, etc.).

In some embodiments, apart from the transducer array, the chamber may house also other parts of the system, such as the waveform generator, the digital controller, the sensor controller, various sensors, or an energy source such as a battery.

In some embodiments, the chamber may be fixed to the patient, or held in contact with the patient during treatment sessions. In some embodiments, it may be in contact with the patient in different positions and orientations, and the transducer array may move inside it in a pre-programmed manner and/or in response to measured parameters.

In some embodiments, the chamber may include automatic acoustic gel dispensing, in a pre-programmed manner, manual manner or in accordance with the measured acoustic coupling. In some embodiments, the transducer chamber may also include a physical pressure sensor, and the sensor controller will raise an alarm and/or retract the transducer if pressure seems too high to maintain patient safety.

Exemplary Sensors

In some embodiments, apart from receiving the reflected ultrasound signal picked up by the transducer array, the sensor controller receives measurements from a set of sensors, based on which it sends commands to the digital controller. In some embodiments, the set of sensors 10 include, but are not limited to, a cavitation detector, a blood pressure meter, heart rate meter, temperature sensor, vital signs monitor, ECG, SpO2, water/saline/fluid intake, urine flow meter, or a meter of the presence of blood or proteins in the urine. In some embodiments, these measurements may be used to estimate the treatment efficiency, efficacy, provide warning of patient stress or discomfort, and to adjust or stop the treatment in response.

In some embodiments, the sensors can include measurement of thermal changes (to enable control and immediate avoidance of thermal changes at the tissue), and detection of cavitation (to enable immediate avoidance of cavitation). In some embodiments, the sensors include identification of renal artery, to enable automatic (or manual) moving and orientating the energy to kidney regions relative to the location of the renal artery, and to enable measurement of blood flow, peak flow velocity and pulsatility index in the renal artery.

In some embodiments, the sensors may include sensors related to the urine, including urine flow, cumulative urine output, creatinine levels, protein levels, protein-to-creatinine ratio, and/or the chemical levels in the urine. The measured parameters may be used to close the loop in the controller in order to control the treatment delivery.

In some embodiments, the sensors are incorporated in the device. In some embodiments, the sensors are located outside the device as independent parts.

Exemplary Digital Controller and Waveform Generator

Figure 3A:
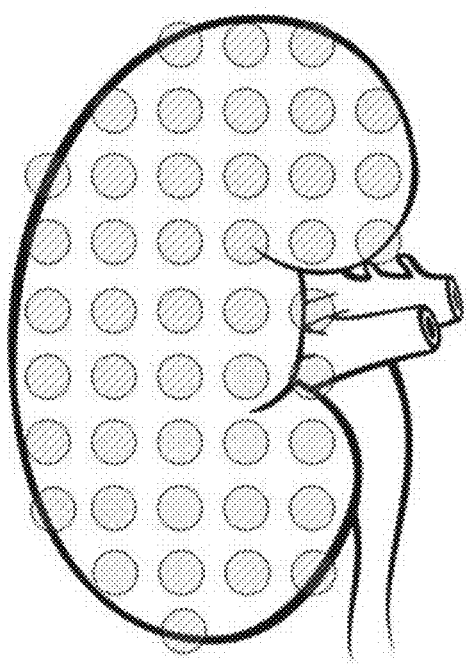
FIGS. 3a and 3b are schematic representation of an example of an embodiment of the activation pattern, in accordance with some embodiments of the invention.

In some embodiments, the digital controller drives the waveform generator, and is in charge of determining the various parameters of the sonication. In some embodiments, such parameters include, for example, the sonication times and durations, waveform parameters and shape, amplitude or area of sonication. In some embodiments, for example, the digital controller generates and outputs N low-power, digital signals (sequences of logical '0's and '1's—22), paced by an internal or external clock. In some embodiments, the digital controller creates phase delays between the signals, in order to focus the ultrasonic beam in a single or multiple of focal points in the sonicated region—through a mechanism of beamforming—as illustrated in FIG. 3a. In some embodiments, other waveforms may be formed, including sinus, saw-tooth, Gaussian-shaped, gauss-shaped sinusoidal patterns, and other shapes and duty cycles or continuous, or combinations thereof.

Optionally, the portion of a kidney being treated in accordance with some embodiments of the invention as described herein is between 2% and 100% of the kidney, for example, between 10% and 60% of a kidney or between 20 and 40% of a kidney. In some embodiments, it may be for example over 30%, for example over 50%, for example over 70%, for example 100% of the kidney. The portions may be calculated on a volumetric basis, or on a cross-sectional basis.

Figure 3B:
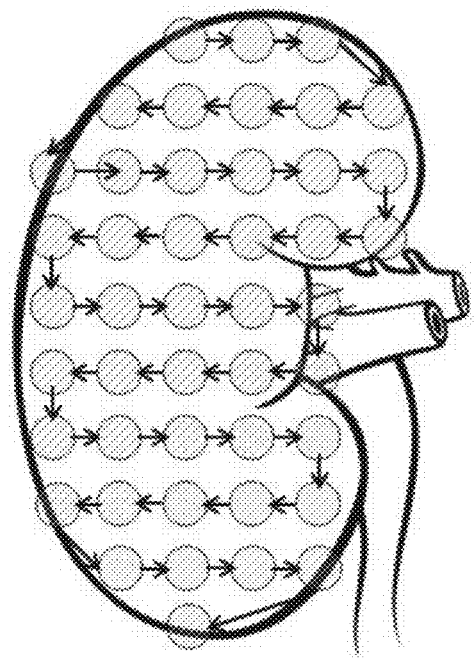
Figure 4:
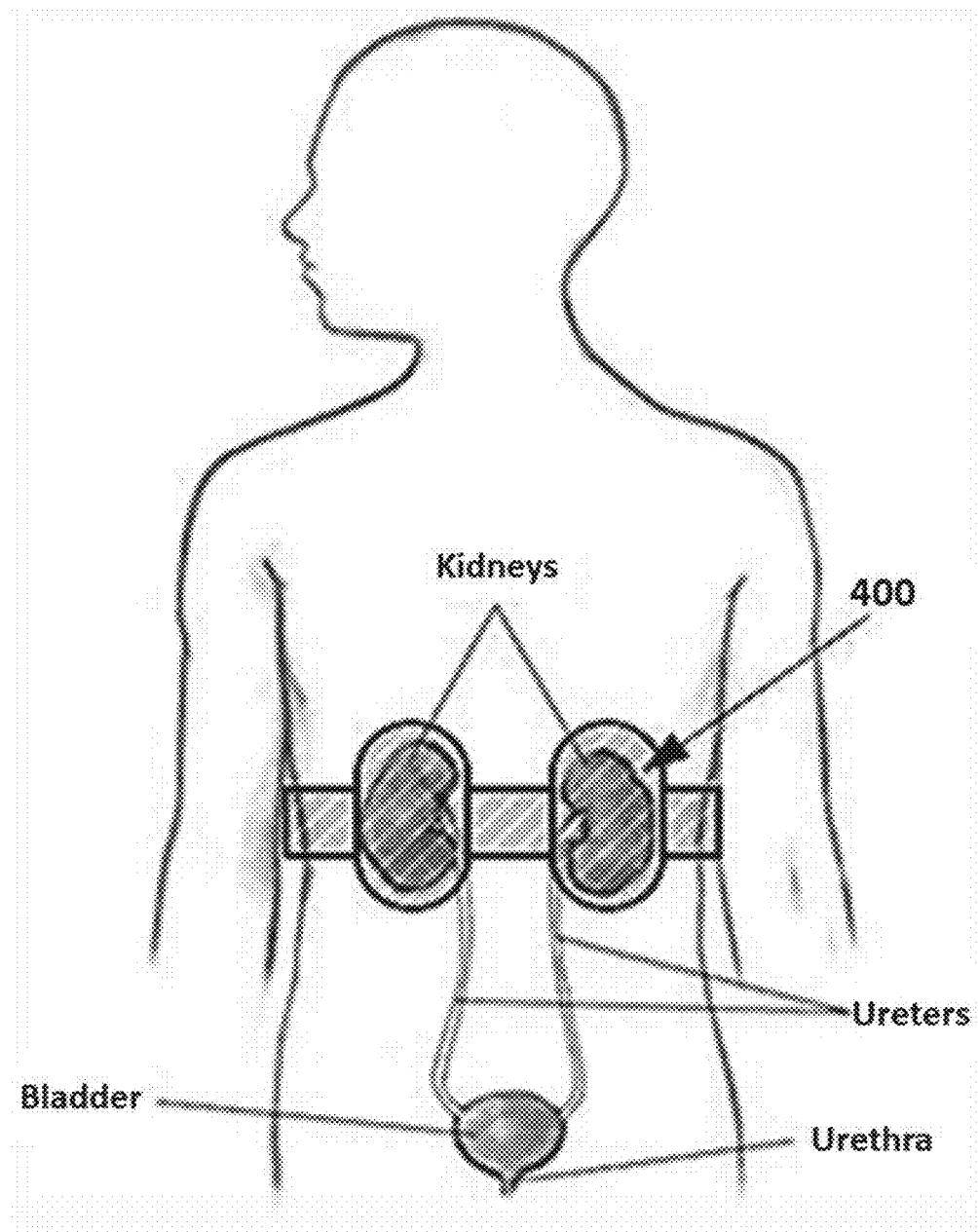
FIG. 4 is a schematic representation of an example of an embodiment of the device, in accordance with some embodiments of the invention.

In some embodiments, the digital controller dynamically changes different parameters of its output signals, according to pre-defined programs or in response to inputs from the sensor controller. In some embodiments, some of the parameters that are changed dynamically are: activation times and durations, transmission amplitude (power), shut-down in response to safety alerts (such as sudden patient movement), the phase delays between transducer elements, in order to scan the sonicated region, with one or more focal points, as illustrated in FIG. 3b. In some embodiments, the focal point scan patterns are changed dynamically as well, in a predetermined manner or in response to the inputs (tracking changes in the kidney location, for example tracking the periodic movement of the kidney with the patient's breathing or other movements).

In some embodiments, the waveform generator coverts the N digital signals received from the digital controller to amplified analogue signals (4), which induce the transducer array.

In some embodiments, when the transducer array comprises a single transducer element (N=1), the array is designed and shaped to produce a large spot of ultrasound, large enough to cover significant portions of the kidney, or even the entire kidney, when placed facing the kidney properly.

Exemplary Energy and Power Supply

In some embodiments, when a battery pack is used, it has a capacity to allow operation time, for example, of from about 2 hours to about 10 hours. In some embodiments, the battery pack provides power for a full day. In some embodiments, the battery pack provides power for up to a week.

In some embodiments, for example, the battery pack manufactured in a Li-polymer technology, in a 12 Volt configuration weighing about 1 Kg should provide about 20 Ampere-hour of charge capacity. It would allow for an estimated 10 hours of use.

In some embodiments, the device includes a battery charger and spare batteries, which are easy to replace by a person with no special training.

In some embodiments, a docking station is provided for battery recharge. In some embodiments, these docking stations are used in hospitals and/or at home.

In some embodiments, when the device is stationary used, in ICU for example, a 3rd-party medical approved charger (with isolations) is used.

Exemplary Embodiments of Devices

In some embodiments, the device is manufactured so the different components are integrated into one device. In some embodiments, the device is manufactured so the different components are located in two separate regions of the same device. In some embodiments, the device is configured, for example, as a wearable device (e.g.: a belt). In some embodiments, the device is configured, for example, on furniture (e.g.: mattress, chair, etc.). The different configurations are further disclosed below.

Exemplary Wearable Embodiment

In some embodiments, the device is fully mobile and worn by the patient as a vest or a belt 400, for use at home or outdoors—that optionally host the acoustic actuator (ultrasonic transducer that converts electrical energy into acoustic vibrations and pressure waves) system which induces ultrasound vibration to the kidneys.

In some embodiments, the transducers are positioned against the skin in the vicinity of the kidneys, and other system components (sensors, controllers, battery pack) are located in the vest or in a belt and attached by wires to the transducers.

In some embodiments, the transducers are stiff, and are made, for example, from a ceramic piezoelectric material. In some embodiments, the transducers are flexible, and are made, for example, from PVDF, a piezoelectric polymer, or different co-polymers of it. In some embodiments, the transducers are shaped to ergonomically fit the patient's body shape at the back or sides regions facing the kidneys.

In some embodiments, the transducers are coupled acoustically to the skin by a coupling material, such as an ultrasound gel, which may be integrated in the device in different forms. In some embodiments, the coupling material is contained as a disposable pad, pressed by the transducers against the patient's skin. In some embodiments, the coupling material is applied as a liquid or gel directly on the skin where the transducers are positioned, and replenished during treatment by the patient, a care-giver, or by an automatic dispenser integrated in the device. In some embodiments, the gel is replaced periodically, or between treatment sessions, or as indicated by the device when it senses that the ultrasonic coupling is not good enough (resulting in strong reflection close to the transducer's surface).

Figure 5:
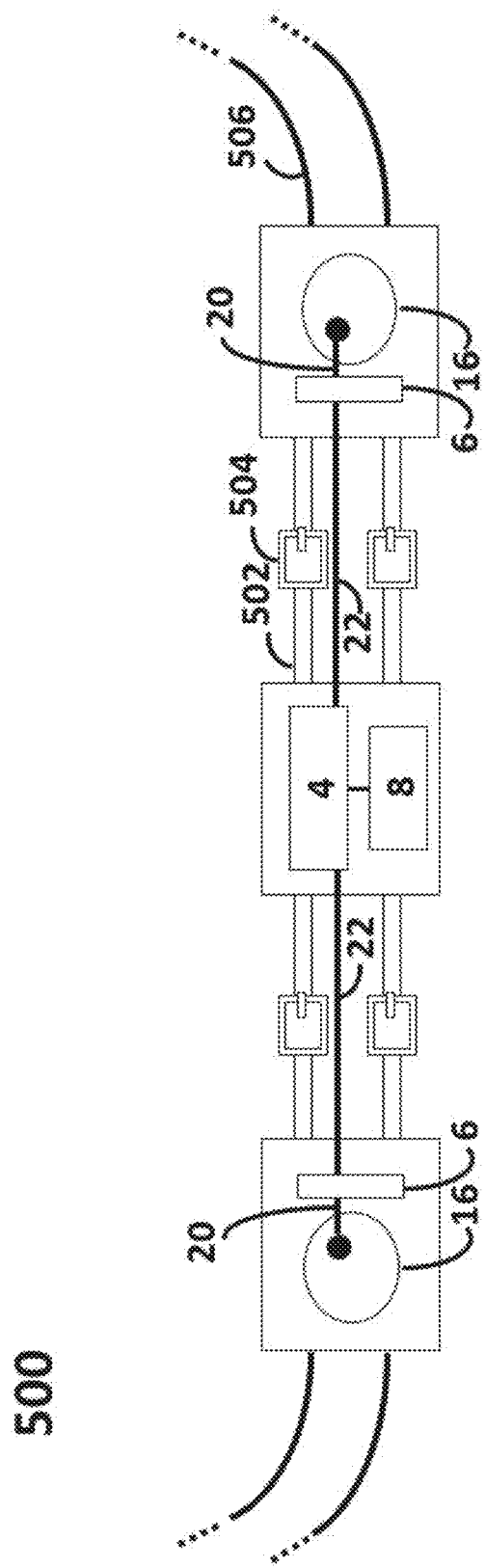
FIG. 5 is a schematic representation of an example of an embodiment of the device, in accordance with some embodiments of the invention.

In some embodiments, as an example, the vest and the position of the transducers in it are configurable to fit an individual patient, and once configured by the patient or the medical staff, the vest may be removed or worn as required. In some embodiments, as shown for example in embodiment 500 in FIG. 5, the position of the transducers can be adjusted, for example, by elastic straps 502 of adjustable length with buckles 504. In some embodiments, the straps connect two side elements housing the transducer and transmitter for each side, to a central element housing the digital controller, sensor controller and possibly the power cells. In some embodiments, the vest formed by these 3 elements wraps around the patient's back and torso, and the two sides are fastened together by clips 506.

Exemplary Temporary in Care Embodiment

In some embodiments, as an example, the transducers are installed and/or held by the medical staff during a check-up at the clinic. In some embodiments, the transducers are installed in a pad that is taped to the patient's back or side at the desired location. In some embodiments, the pads remain facing the kidneys for a certain duration (possibly more than a day) until it is replaced by the medical staff with new pads. In some embodiments, the transducers are held in position by the medical staff for some or all of the treatment duration.

In some embodiments, the transducers chamber may include a bar or color (red-yellow-green) indicator to assist with positioning the transducers in the right location (as estimated by the digital controller).

In some embodiments, the battery pack may be housed in the vest or on a belt, may have a charge capacity indicator, and may provide a warning when close to depletion and should be replaced. In some embodiments, the packs are easily connected and removable by the patient, and also easily connected to a docking-station charger that is provided with the device.

Exemplary in Bed/Chair Embodiment

Figure 6A:
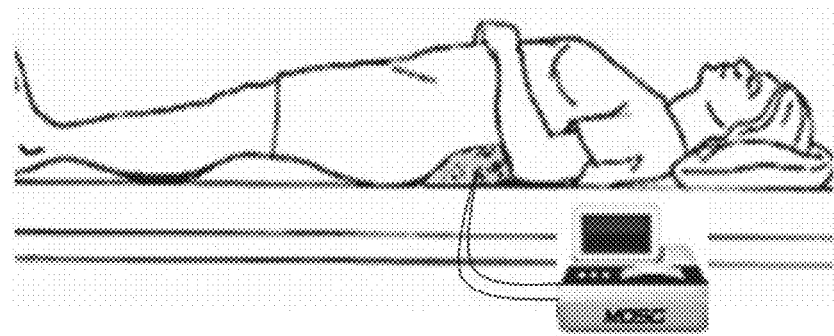
FIGS. 6a and 6b are schematic representations of examples of embodiments of the device, in accordance with some embodiments of the invention.

In some embodiments, as an example, the system is used in at home, at a hospital or a clinic to treat a patient lying on a bed or sitting on a chair, as shown, for example in FIG. 6*a*. In some embodiments, the transducer and sensors unit is worn by the patient, and is attached by wires to a bed-side unit containing the digital controller, power supply, processor, and possibly a screen to view the received image and other sensor data. In some embodiments, the bed-side unit is a mobile cart, allowing the patient a certain degree of mobility.

Figure 6B:
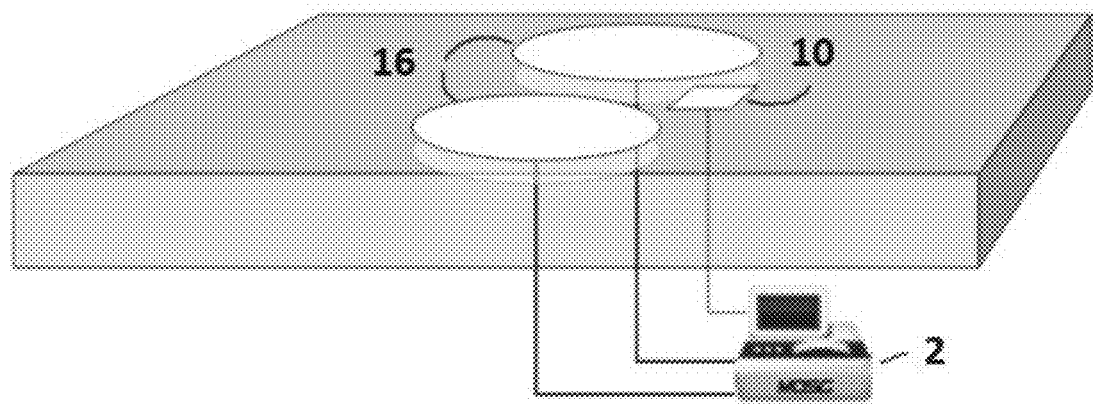

In some embodiments, the transducer and sensors unit are stationary on the bed, and interact with the patient when he is lying in a designated position and place. In some embodiments, it may be part of/integrated with a mattress, as shown for example in FIG. 6*b*: for example, an electrical/electroacoustic unit at the bottom of the mattress (integrated with or below the mattress), and an acoustic conductor layer above it that well fit anatomically with the patient body curvatures: so some areas are supported regularly by the mattress and some areas are supported by acoustic coupling bag, for example, plastic bag filled with water or gel with appropriate acoustic properties for coupling.

Figure 7A:
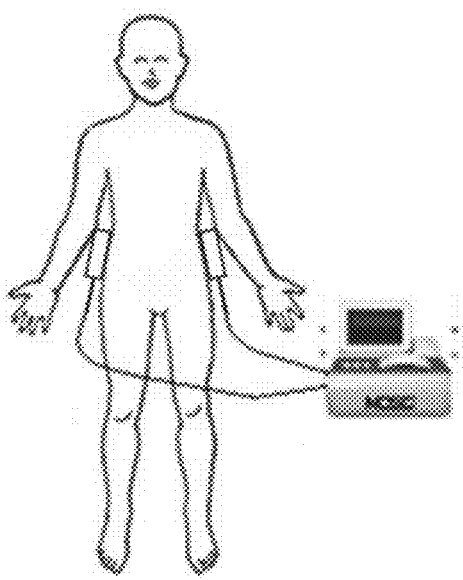
FIGS. 7a and 7b are schematic representations of examples of embodiments of the device, in accordance with some embodiments of the invention.
Figure 7B:
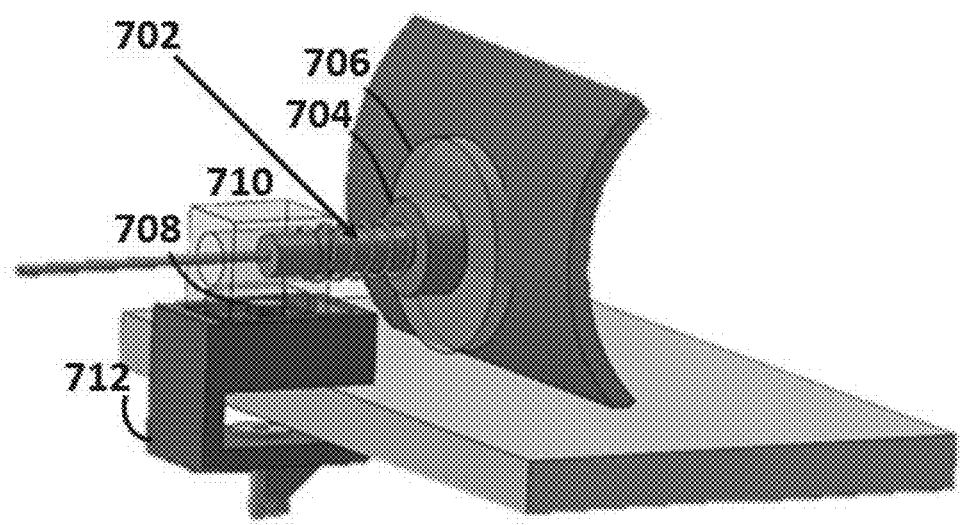

In some embodiments, the transducer is brought near the kidney location with a device (chamber) that is positioned laterally to the patient, and supports the patient from the sides, as shown for example in FIG. 7*a*. In some embodiment, the device controls the pressure applied to hold the transducers in place, measures it to ensure good acoustic contact on one hand, and low pressure and patient safety one the other hand. In some embodiments, as shown for example in FIG. 7*b*, this is performed by a spring 702 maintaining subtle pressure of the transducer 704 and a gel pad 706 against the patient's skin, while a pressure sensor detects any movement of the patient. If the pressure is changed the controller activates a motor 708 that pushes or pulls the transducer holder 710 to adjust the spring back to the desired pressure. The motor is housed in a unit 712 clamped to the bed.

In some embodiments, the probe is positioned by the operator on one or both sides of the patient about the line of the end of the ribs, and brings the device to be in contact with the patient's skin. In some embodiments, the device has an acoustic coupling cover which is replaced between one patient and the other, and once in some time of usage.

In some embodiments, the default height is about 3 to 30 cm above the bed, for example between 5 and 15 cm, for example about 10 cm above the bed. In some embodiments, the orientation of the device relative to the bed is about 0 degrees (parallel to the bed), and/or about +/−15 degrees from the parallel to the bed, and/or about 30 degrees and/or about 45 degrees, and/or about 60 degrees.

In some embodiments, the acoustic coupling cover has a pre-filled gel which is dispensed continuously and/or in response to pressure and/or in a controlled manner to maintain sufficient acoustic coupling with between the device and the patient skin.

In some embodiments, the cover has a chip for communicating with the device to control the dispensing of the gel and/or to measure parameters associated with skin contact, e.g. acoustic coupling, spill off of acoustic energy, cavitation, temperature, physiological parameters, pressure, and/or others). In some embodiments, the cover is replaced between patients and/or replaced every sometime of operation and/or replaced once the pre-filled gel or fluids are depleted.

In some embodiments, the power supply may be a battery pack, in a similar manner to the worn device. In some embodiments, is a power converter connected to the power grid with proper isolation for safety, and, in some embodiments, it is a combination of these two options, where the battery pack is charged when plugged to the grid and is being consumed when unplugged.

Exemplary Internal Embodiments

In some embodiments, some or all parts of the device can be implanted inside the body of the subject, making the device an implantable device. In some embodiments, the device is implanted inside the body, in the vicinity of the kidneys. In some embodiments, the device is controllable wirelessly from a cellphone, smartphone, tablet and/or a dedicated device. In some embodiments, only the transducer (and possibly associated driving circuitry) is implanted inside the body of the subject, connected by wires to the external electronics and power source. In some embodiments, the transducer and waveform generator (and possibly associated circuitry, e.g. power circuitry and/or communication circuitry and/or control circuitry) are implanted inside the body of the subject, with the signal and/or power transmitted to it wirelessly from the external components, either by RF, wireless technology or by coupled coils, or by acoustic energy transmission.

In some embodiments, the device is adapted to be used in a catheter configuration. In some embodiments, the transducers are brought to the end of a catheter, while the rest of the parts remain outside the body of the patient.

Exemplary Parameters

Exemplary Power

In some embodiments the average emitted acoustic power is lower than 20 Watts, preferably lower than 10 Watts, for example in the range of 0.05 to 5 Watts, for example in the range of 0.5-3 Watts, for example about 1-2 Watts.

Exemplary Timing

In some embodiments, the digital controller 4 generates a digital signal, for each of the N channels, as depicted for example in FIG. 8. Four timing parameters define the digital controller output signal: $T_1$—pulse duration, $T_2$—burst cycle, $T_3$—burst duration, $T_4$—repetition cycle.

In some embodiments, the waveform generator 6 generates an analogue signal for each of the pulse duration, for each of the N channels. The signal is denoted as $X_i(t)$ where $i \in [1,N]$. The signal is defined by its amplitude—A, its period $T_0$ and its shape.

Figure 9A:
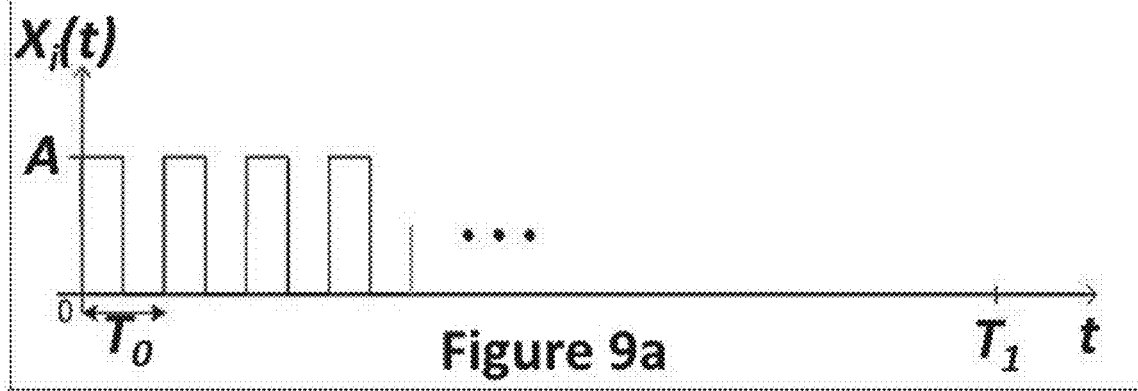
FIGS. 9a-d are schematic representations of examples of output signals, in accordance with some embodiments of the invention.
Figure 9B:
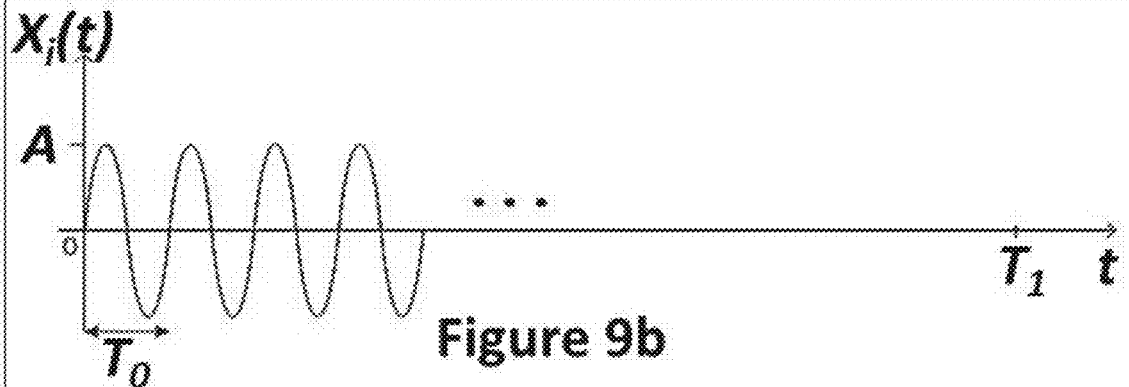
Figure 9C:
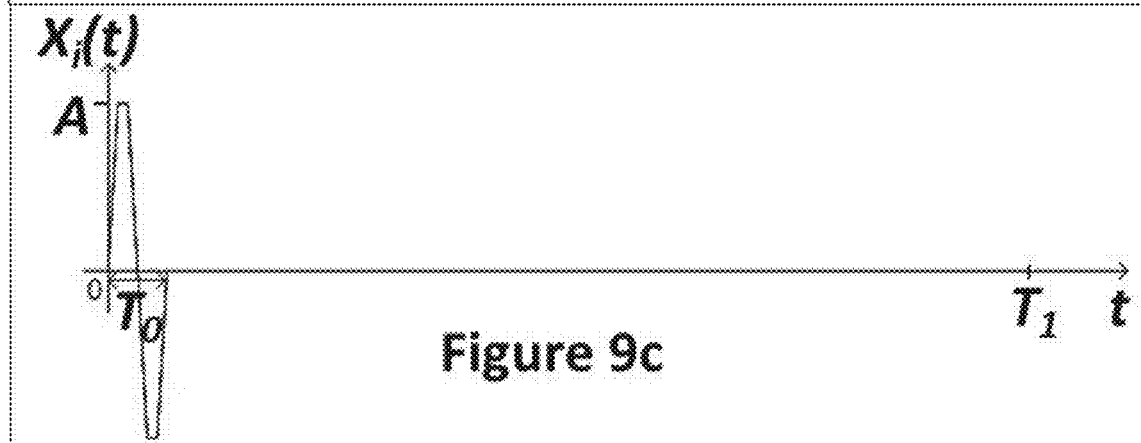
Figure 9D:
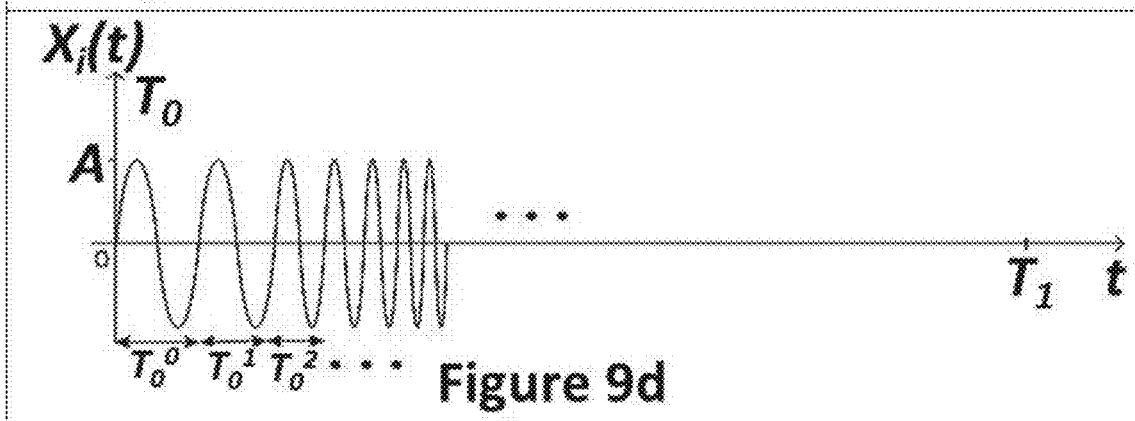

In some embodiments, the waveform generator output signal, may be a rectangular wave, with frequency of $f_0=1/T_0$—as depicted for example in FIG. 9a. This optional method lets the electro-acoustic frequency response, of the Transducer Array, determine the ultrasonic signal shape. Alternatively, in some embodiments, the signal generator may perform a signal shaping in the electrical domain and output a shaped signal, as depicted for example in FIG. 9b with a sine wave as an example. Alternatively, the Waveform Generator may generate a time narrow, high power, spike signal, as illustrated in FIG. 9c. Alternatively, the Waveform Generator may generate a chirp signal, with varying frequency ($T_0^0 > T_0^1 > T_0^2 > \ldots$), as illustrated in FIG. 9d.

Exemplary Basic Frequency

In some embodiments, for the ultrasonic signal to effectively impact the nephrons of the kidneys, including for example the glomerulus and the tubules of the kidney, an acoustic wavelength in the order of the glomerular size and the tubules size, is desired. Since the average glomerular diameter is bounded: $D_g < 250$ μm, ($D_g > 100$ μm, but tubular structure are smaller, and maybe desired to be impacted as well), and since the tubules may have narrower diameter and longer length to be desired to treated, for example of up to 350-400 μm, and since the sound velocity in soft tissue—as is the kidney and its surrounding tissues—is approximately C=1500 m/sec, the desired acoustic spectrum should have, in some embodiments, a central frequency at f>6 MHz, for example about 5-7 MHz, a range above 5 MHz, 4-9 MHz, 5-15 MHz, above 8 MHz, 7-13 MHz, above 10 MHz, 7-25 MHz, 10-50 MHz. This may be achieved by setting the signal central frequency, at the Waveform Generator output with, $f_0 > 6$ MHZ. Generally speaking the energy to be delivered shall have energy predominantly (almost entirely, e.g. >80% of the power, preferably >90% of the power) in frequencies above 4 MHz, for example in frequencies above 5 MHz. In some embodiments, the frequency may be varied depending on the tissue to be targeted and/or the targeting by harmonics.

In some embodiments, the Transducer Array may be designed accordingly, to have a resonance frequency $f_c = f_0 > 6$ MHz, so as to maximize the electroacoustic transduction efficiency at the relevant frequency, and have high acoustic power at the transducer output.

Exemplary Safety Considerations

In some embodiments, some of the parameters in this method are set based on safety considerations, with special consideration given to the risks of cavitation and heating.

Cavitation:

In some embodiments, the following parameters: electrical power at transducer input, signal frequency, transducer central frequency, are set in a manner that maintains the Mechanical Index limit, defined by the US FDA:

$$MI = \frac{P_{0.3}}{\sqrt{f_c}} < 1.9$$

Where $P_{0.3}$ is the pressure (in MPa) of the acoustic field, decreased at 0.3 dB/cm/MHz, and $f_c$ is the center frequency (in MHz) of the field.

Heating:

In some embodiments, the following parameters: electrical power at transducer input, timing parameters $T_1$, $T_2$, $T_3$, $T_4$, signal frequency (electric), transducer central frequency (acoustic), are set in a manner that maintains the Thermal Index limit recommended by the US FDA:

$$TIS = \frac{W_0 \cdot f_c}{210} < 6.0$$

In some embodiments, during treatment application, an elevation in the temperature of the site of radiation is no higher than 2 degrees Celsius over the present temperature of the site at the moment of the treatment. In some embodiments, during treatment application, an elevation in the temperature of the site of radiation is no higher than 1 degree Celsius over the present temperature of the site at the moment of the treatment. In some embodiments, during treatment application, no elevation and/or unnoticeable change and/or non-significant change in the temperature of the site of radiation is detected and or induced over the present temperature of the site at the moment of the treatment.

Other Considerations

In some embodiments, assuming the total acoustic energy of a single signal is $E_s$, being delivered over a duration of $T_1$, the mean power if that signals was continuously delivered would have been $W_0 = E_s/T_1$. In case TIS under this calculation is lower than 6.0, then no further restriction applies other than the MI restriction.

In some embodiments, alternatively, the pulse duty cycles T1/T2 and the burst duty cycles T3/T4, provide ability to lower the accumulated heat, and therefore ensure meeting the TIS<6.0 requirement. Hence, $W_0 = E_s * T_3/(T_2 * T_4)$ In some embodiments, the T2 is set to interact with timing properties that typically characterize stretch receptors response, for example between 20 Hz and 200 Hz, for example between 50 Hz to 120 Hz, for example about 80 Hz (i.e. T2 of about 12.5 milliseconds).

Exemplary Methods of Use

In some embodiments, the treatment provided by the device and the method is performed as a preemptive treatment.

In some embodiments, the treatment provided by the device and the method is performed before a surgical intervention on a patient.

In some embodiments, the treatment provided by the device and the method is performed after a surgical intervention on a patient.

Figure 10:
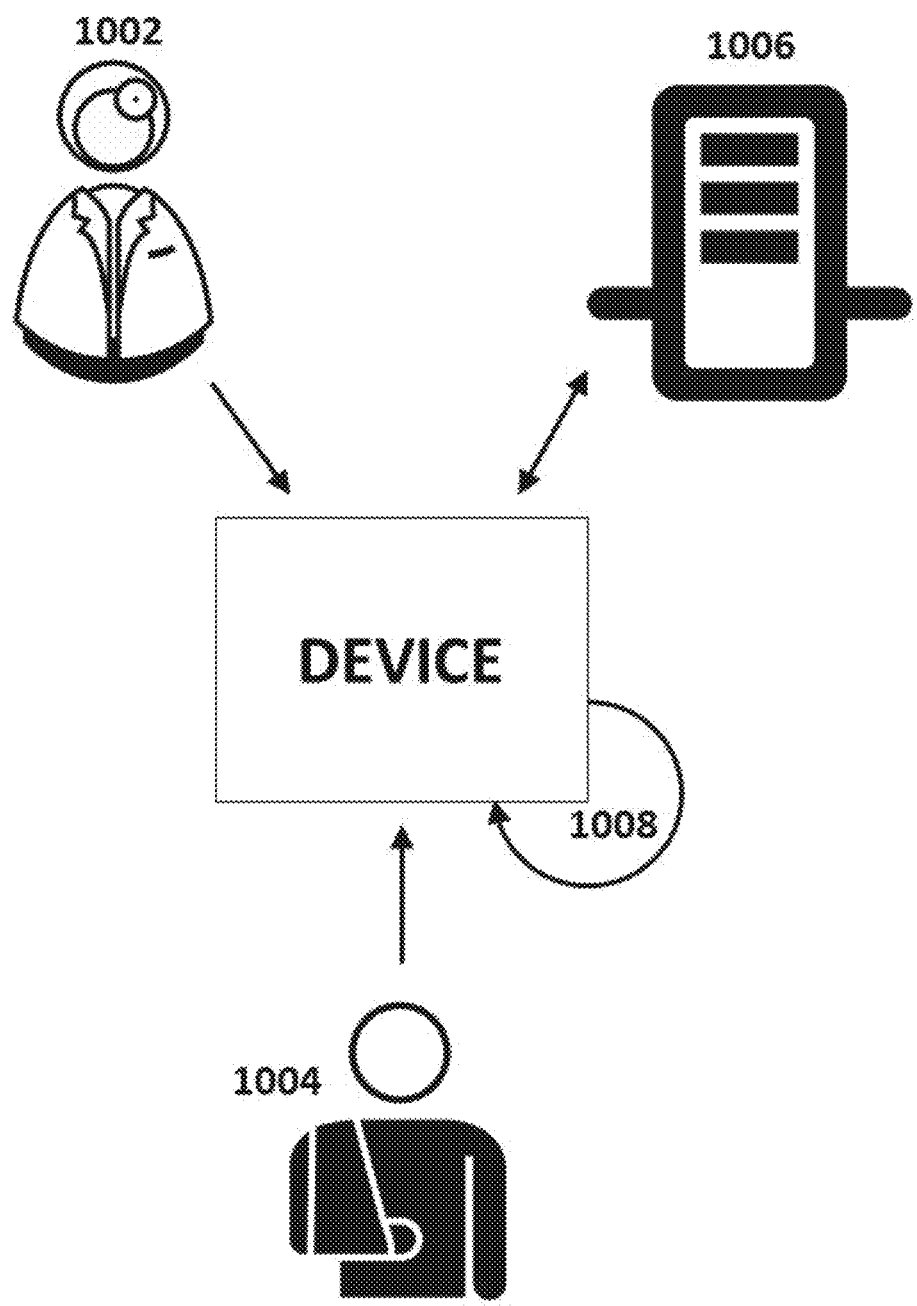
FIG. 10 is a schematic diagram of examples of sources of activation of the device, in accordance with some embodiments of the invention.
Figure 11:
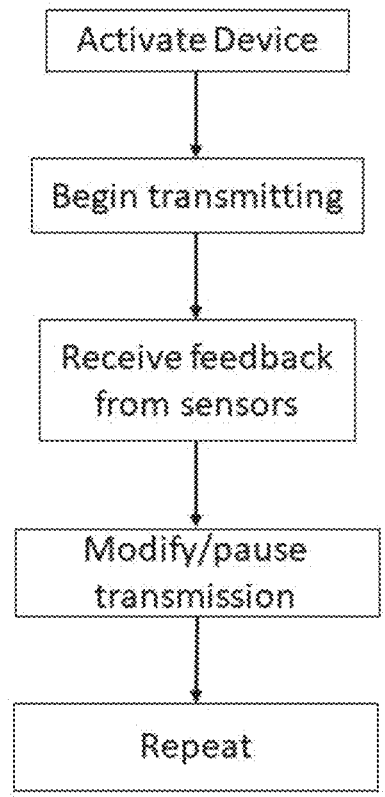
FIG. 11 is a schematic flowchart of an example of a method of operation of the device, in accordance with some embodiments of the invention.
Figure 12:
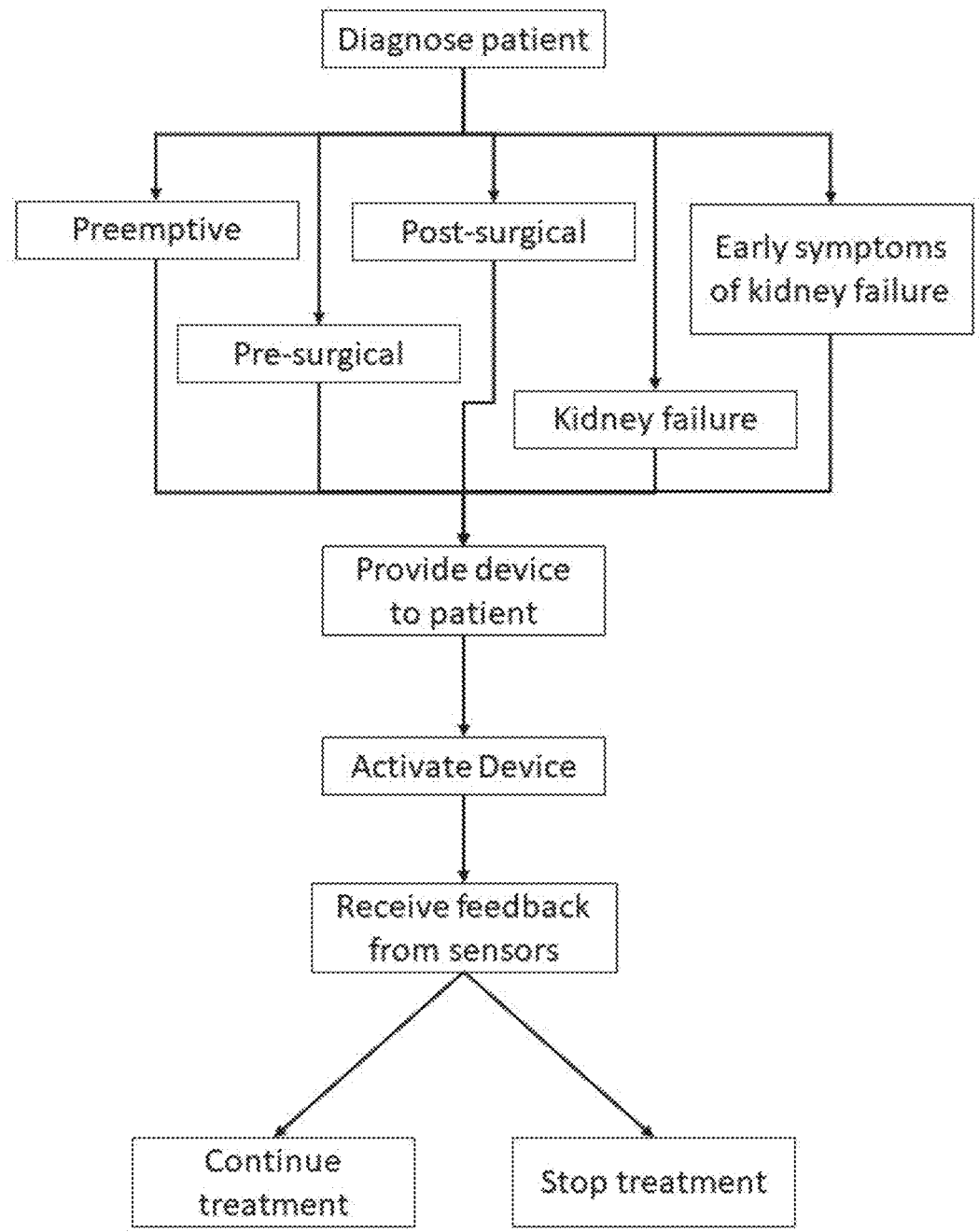
FIG. 12 is a schematic flowchart of some examples of activation criteria of the device, in accordance with some embodiments of the invention.

In some embodiments, the treatment is activated by a human (e.g.: a physician 1002, a nurse, the user 1004, or any other dedicated personnel), as shown for example in FIG. 10.

In some embodiments, the treatment is activated by a centralized system 1006, as shown for example in FIG. 10, which receives information regarding the patient from a variety of sensors. For example, when the patient is at the hospital and connected to a variety of sensors, the information provided by the sensors is sent to a centralized system which activates the device when the parameters received match a predetermined threshold.

In some embodiments, the treatment is activated by the device itself 1008, as shown for example in FIG. 10, which receives information regarding the patient from a variety of sensors. For example, when the patient is wearing the device, a variety of sensors monitors the patient, and the device activates itself when the parameters received from the sensors match a predetermined threshold.

In some embodiments, the treatment activation or deactivation is a combination of activation by a human, activation by a centralized system and/or activation by the device itself.

In some embodiments, the treatment is activated when early symptoms of kidney failure are detected. In some embodiments, the treatment is activated when symptoms of kidney failure are detected. In some embodiments, the treatment is activated when kidney failure is detected.

In some embodiments, the treatment is activated when at least one monitored parameter arrives at a certain threshold. In some embodiments, the monitored parameters are, for example: decreased urine output, increase of creatinine and/or urea in the blood, increase of KIM-1 (HaVCR), increase of neutrophil gelatinase-associated lipocalin (NGAL) (Lipocalin, Keroton 20) in the urine, and/or increase of TIMP-2 and IGFBP-7 in blood (NephroCheck® test).

In some embodiments, the treatment is activated when the user has a medical history indicating low kidney performance.

In some embodiments, the treatment is activated after the subject has suffered a traumatic event, for example: sepsis, heart problems, hemorrhagic shock, hypovolemic shock, liver failure, or any other situation where kidney failure is expected to appear.

In some embodiments, the treatment is performed for few hours, a few days, or for a longer period. During that time it may be active intermittently every few hours, every few minutes, and up to a constant activation, or as required by the patient or healthcare provider. Activation times and periods may also be regulated automatically based on readings from the set of sensors on the device.

Exemplary Indications and Protocols

In some exemplary embodiments of the present invention, the system is used for patients arriving at a clinic already with indication of renal failure. For example, in some exemplary embodiments of the present invention, the system is used for patients arriving at a clinic already with acute renal dysfunction. In some exemplary embodiments of the present invention, the system is used for patients arriving at a clinic with known chronic kidney disorder.

In some exemplary embodiments of the present invention, the system is used for treating a patient with known risk of developing kidney disorder. In some examples, such patients include, patients with only one kidney, and/or diabetes, and/or existing kidney stones, and/or patients undergoing a condition with reduced blood pressure, and/or patients undergoing a condition with reduced cardiac output and/or patients that are exposed to nephrotoxic condition.

In some exemplary embodiments of the present invention, the system is used for treating a patient with known risk of worsening of already known kidney disorder. In some examples, such patients include, patients with only one kidney, and/or known CKD, and/or present AKI/ATN, and/or diabetes, and/or patients undergoing a condition with reduced blood pressure, and/or patients undergoing a condition with reduced cardiac output and/or patients that are exposed to nephrotoxic condition (including for example due to infection and/or due to contrast media, and/or due to other toxins). In some examples, such patients include, patients having a medical condition in which they might no longer benefit (or worsen) from use of ACE inhibitors and/or diuretics.

In some exemplary embodiments of the present invention, the system is used for support and/or improve urination function of the kidney.

In some exemplary embodiments of the present invention, the system is used for preventing or reducing potential damage of an event that might cause acute kidney dysfunction.

In some exemplary embodiments of the present invention, the system is used for preventing or reducing potential damage of an event that might cause chronic kidney dysfunction.

In some exemplary embodiments of the present invention, the system is used for preventing or reducing long term damage (e.g. development of CKD) as a result of an acute kidney dysfunction.

In some exemplary embodiments of the present invention, the system is used for treating a patient with known risk of developing kidney disorder due to sepsis, ischemia, dehydration, hypovolemic condition, hemorrhagic shock and/or cariogenic shock, and/or acute myocardial infarction, and/or sustained cardiac arrhythmia causing non-optimal cardiac output or blood flow, and/or acute heart failure and/or chronic heart failure.

In some exemplary embodiments of the present invention, the system is used for treating a patient with known risk of developing kidney disorder due to a procedure that might impair normal cardiac output and/or blood pressure and/or blood flow and/or perfusion to kidney. For example, patients undergoing cardiac surgery, and particularly patients with prolonged surgery duration, and/or patients undergoing use of heart-lung machine, and/or patients undergoing use of cardiac assist devices (including, without limitation, VAD, LVADs, intra-aortic balloon pumps, artificial heart, etc), and/or patients undergoing interventional cardiac procedure (e.g. coronary intervention).

In exemplary embodiment of the present invention, the treatment starts before the procedure.

In exemplary embodiment of the present invention, the treatment starts during the procedure.

In exemplary embodiment of the present invention, the treatment starts after the procedure.

In exemplary embodiment of the present invention, the treatment starts during or after the procedure if a kidney damage risk factor was identified.

In exemplary embodiment of the present invention, one or more biomarkers are evaluated for the patient and the treatment starts during or after the procedure if the one or more biomarkers indicate elevation in kidney damage risk beyond a threshold.

In exemplary embodiment of the present invention, one or more of serum Creatinine, and/or urine NGAL, KIM-1, and/or NephroCheck are evaluated a few hours after the start of the procedure (for example, within 12 hours, or about within 2-8 hours, or within about 3-6 hours after beginning of the procedure), and an elevation in one or more of the indicators beyond a predetermined threshold indicates start of treatment.

In some embodiments of the present invention, the treatment lasts at least an hour.

In some embodiments of the present invention, the treatment lasts at least 3 hours.

In some embodiments of the present invention, the treatment lasts at least 5 hours.

In some exemplary embodiments of the present invention, the system is used for treating a patient with GFR below 40 ml/min and/or with NGAL of above 100 ng/ml and/or with Serum Creatinine of above 1.2 mg/dl, or with a combination thereof.

In some exemplary embodiments of the present invention, the system is used for treating a patient after an onset of an acute heart failure episode, if the patient has GFR below 40 ml/min and/or with NGAL of above 100 ng/ml and/or with Serum Creatinine of above 1.2 mg/dl, or with a combination thereof.

In some exemplary embodiments of the present invention, the system is used for treating a patient before, and/or during and/or after an interventional procedure or a cardiac surgery, if the patient has GFR below 40 ml/min and/or with NGAL of above 100 ng/ml and/or with Serum Creatinine of above 1.2 mg/dl and/or with a combination thereof.

Exemplary Indications and Protocols for the Device

In exemplary embodiments of the present invention, the system is configured to deliver the ultrasonic energy to the kidney for prolonged period without producing an image of the kidney.

In exemplary embodiments of the present invention, the system is configured to deliver the ultrasonic energy to the kidney for prolonged period while producing an image of the kidney.

In exemplary embodiments of the present invention, the system is configured to deliver the ultrasonic energy to the kidney for prolonged period with only producing an image of the kidney once in an hour or more.

In exemplary embodiments of the present invention, the system is configured to deliver the ultrasonic energy to the kidney for prolonged period with only producing an image of the kidney at setting time.

In exemplary embodiments of the present invention, the system is configured to deliver the ultrasonic energy to the kidney for prolonged period without producing an image of the kidney. The system comprises transducers positioned on the back side of the patient, or laterally, wither within a belt or a wearable garment or within a bed or within a mattress, or as a bedside component or as a chair component, with the transducers position at a distance of no larger than 10 cm from the kidney's cortex, preferably no more than 7 cm, preferably no more than 5 cm from the kidney's cortex. In some embodiments, the system safely delivers ultrasonic energy at frequency ranges of 5 MHz and above, preferably most of the energy is between 5-10 MHz. In some embodiments, the system delivers the ultrasonic energy towards the target organ at least once in every second, in at least 500 seconds of every treatment hour. In some embodiments, the system delivers the ultrasonic energy towards the target organ at least 5 times in every second, in at least 1000 seconds of every treatment hour. In an example, the system delivers the ultrasonic energy towards the target organ at least 5000 times in every treatment hour, for at least one hour.

In an example, the system further comprises pressure and coupling measurement, for example for limiting the pressure on the skin and for ensuring proper coupling. In an example, the system delivers at least $1/100$ of the maximal permitted safe delivery of the ultrasonic energy in the desired frequency range. In another example, the system delivers at least $1/10$ of the maximal permitted safe delivery of the ultrasonic energy in the desired frequency range. In an example, the system further comprises cavitation detection and temperature monitoring, for ensuring safe energy transmission.

Various embodiments and aspects of the present invention as delineated hereinabove and as claimed in the claims section below find experimental support in the following paragraphs.

Pig Experimental Study

The reported procedures, performed in animals, were authorized by the Council for Experiments in Animals. Two healthy female pigs (PIG-1 and PIG-2), weighing 53 Kg each, were treated with low intensity and high frequency ultrasonic energy, induced to the kidneys area in a noninvasive and prolonged manner Both kidneys—left and right—were treated simultaneously. The experiment was divided into repeated alternating sessions of baseline and activation. The baseline session, in which ultrasonic induction was off, served as control. In the activation sessions, both kidneys were treated with ultrasonic energy induction. Urine and blood samples were taken in predetermined times during each session, for biochemistry analysis, which served for evaluation of the method's efficacy and safety. After each experiment, the animal was sacrificed and its kidneys were harvested for histological analysis, which served for safety evaluation. Temperature and drip rate were measured as well.

Animal Preparation

Both animals weren't fed for at least 12 hours before the experiments. The animals were laid on their belly. Prior to the experiment the animals were sedated and medicated with Ketamine, Xylzin and Atropine. Throughout the experiment the animals were kept anesthetized using a changing dosage of Isoflurane: 2-3.5%. An IV port was placed for taking blood samples. A second IV port was placed for infusion of fluids. Throughout the experiment, drip rate of the fluids infusion was kept in an estimated range of 8-25 milliliter per second (1.6 to 5 drips per second, estimating 5 ml per drip). An arterial port was placed for blood pressure measurement. During the experiment blood pressure, heart rate and oxygen saturation (SpO2) were monitored and documented. A femoral artery line was placed for injection of Iohexol, for the purpose of Iohexol clearance evaluation. A Foley catheter was inserted into the bladder, for urine volume measurement and for collection of urine samples for biochemistry analysis. The animal's kidneys were confirmed using an Ultrasound imaging device and their position was marked on the surface of the skin. The animals were left to stabilize for about 90 minutes from start of anesthesia before the beginning of the experiment.

Sonication Method

Figure 13A:
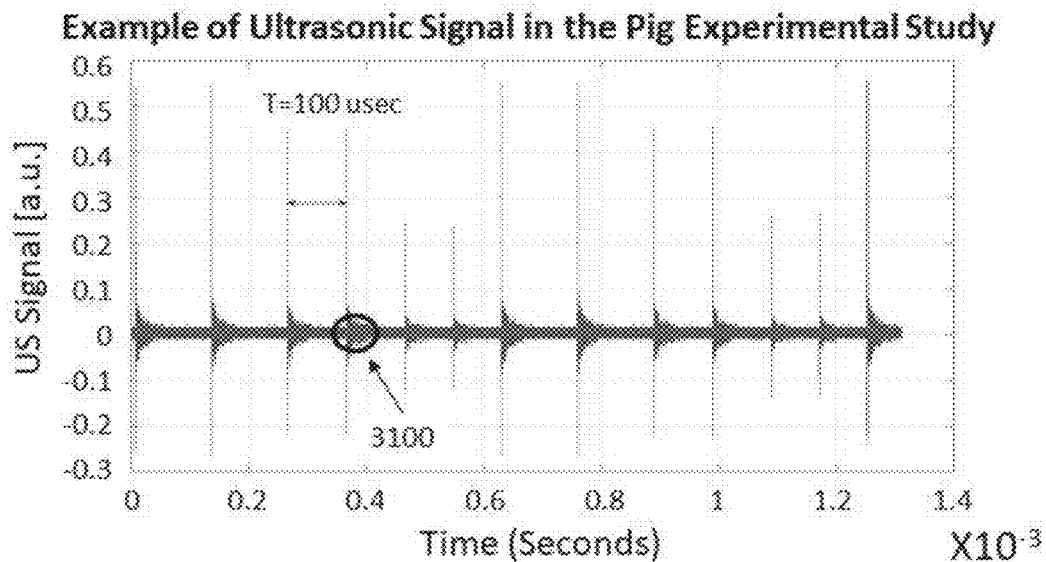
FIGS. 13a-c are time and frequency domain graphs of ultrasonic signal used in studies, in accordance with some embodiments of the invention.
Figure 13B:
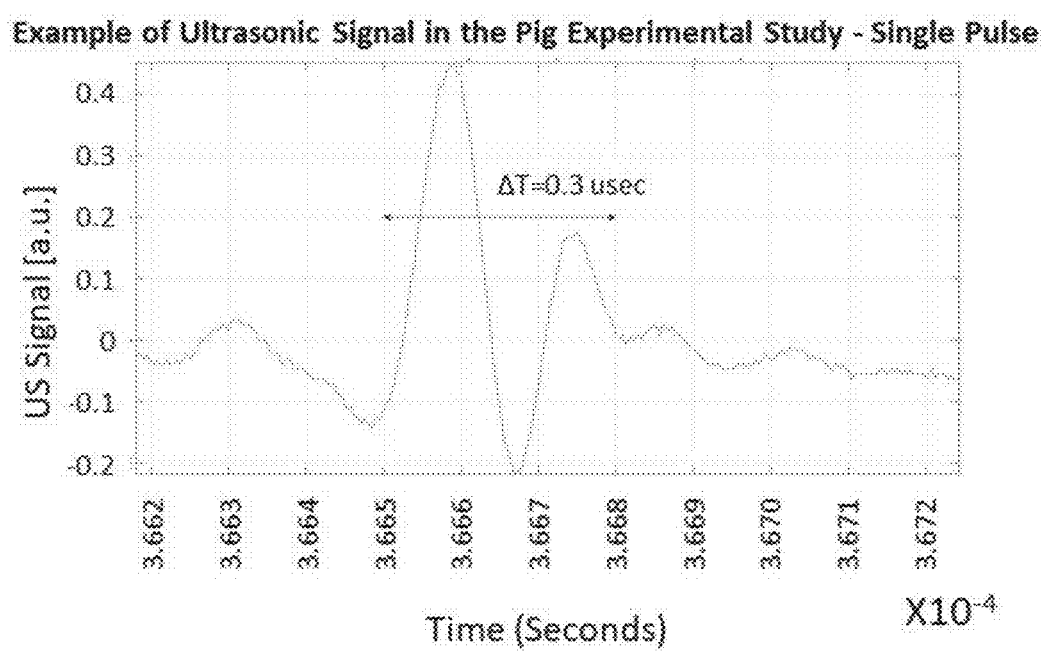
Figure 13C:
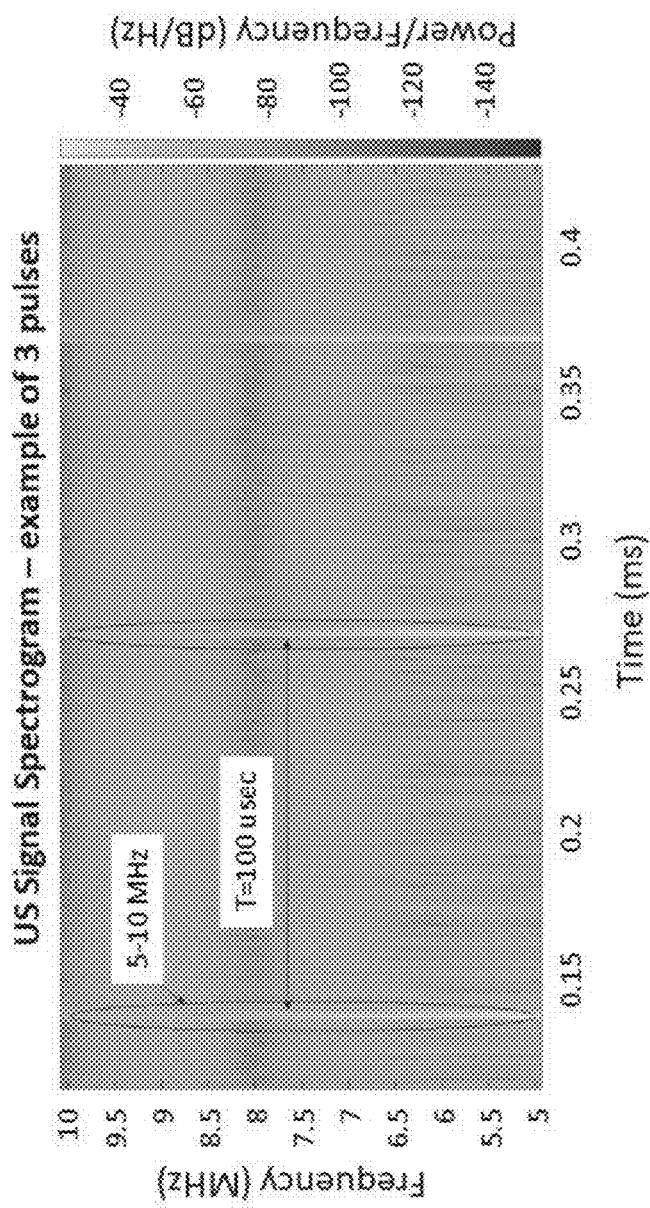

The ultrasound energy delivery system included a transducer probe consisting of a row array of piezoelectric elements and a signal generation and amplification unit that supplied the signal to the probe. The system was programmed to produce a sequence of narrow pulses with pulse duration of 0.3 micro-seconds and a repetition rate of 10 KHz. The pulses were shaped by the transducer electroacoustic frequency response with a frequency bandwidth of 5-10 MHz with central frequency of about 7.5 MHz. The temporal pattern of the ultrasonic signal is depicted, for example, in FIGS. 13a-c. An example of the ultrasonic signal used in the study can be seen, for example, in FIG. 13a. An example of a single pulse 3100 in the ultrasonic signal can be seen, for example, in FIG. 13b. An example of 3 pulses of the ultrasound signal spectrogram can be seen, for example, in FIG. 13c.

An electrical programmed beam-forming mechanism generated a focused beam and a periodic spatial steering of the beam, in a manner similar to the transmission of an ultrasonic signal in an Ultrasound Imaging device—in a 2 dimensional imaging mode (2D). We estimated the location of the kidney to be in a depth of 3-9 cm (from end to end), with substantial portion of the tissue at about 6.5 cm, and focused the beam to that depth. Intensity of focused ultrasound derived a Mechanical Index of MI=0.3 well below MI of 1.0, and certainly well below the maximal allowed MI=1.9 for medical imaging devices by the FDA.

The sonication was performed by a manual slow scanning of the kidneys area, using US imaging gel for acoustical coupling to the body, with as minimal as possible deviation to the signal.

Experiment Timeline

Figure 14:
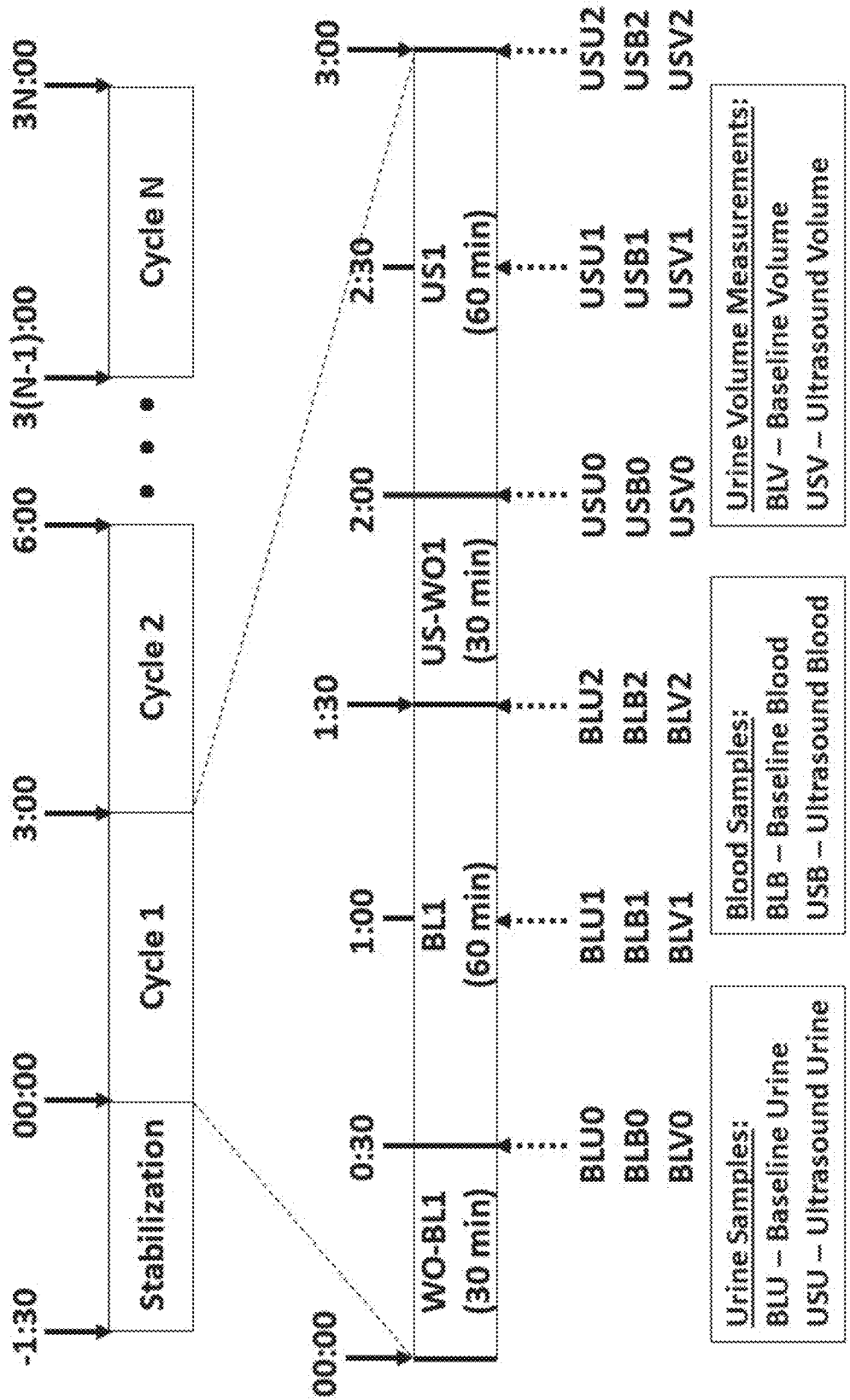
FIG. 14 is a schematic representation of the experiment timeline, in accordance with some embodiments of the invention.

Each experiment consisted of a repetition of the following 4 sessions several times, as shown in FIG. 14:

1. Baseline Washout—WO-BL: lasted about 30 minutes and intended to allow urine that may have been left in the bladder from previous session to be cleared, before baseline sampling and measurement of urine started
2. Baseline—BL: lasted about 60 minutes and intended for taking blood and urine samples that served as a reference for the US activation session.
3. Ultrasound Activation Washout—US-WO: lasted about 30 minutes in which ultrasound was activated and intended to allow urine that may have been left from previous session to clear.
4. Ultrasound Activation—US: lasted about 60 minutes in which ultrasound energy was induced to the both kidneys simultaneously.

In PIG-1 this sequence of sessions was repeated 4 times. In PIG-2 the sequence was repeated 3 times.

Measurements

In each BL or US session urine volume was measured, and blood and urine were sampled 3 times: at the beginning of the session and 30 minutes and 1 hour into the session. Volume was measured relative to the previous measurement and was intended for Urine Flow evaluation and for estimations of GFR.

Urine samples were analyzed in a Biochemistry lab, for concentrations of: Creatinine, Protein, Sodium, Potassium and Chlorine. Blood samples were analyzed in a Biochemistry lab, for concentrations of: Creatinine, Calcium, Phosphor, Urea, Sodium, Potassium and Chlorine.

Urine samples were also analyzed semi-quantitatively during the experiment, using standard urine dipstick analysis kit, for close to real-time identification of potential damage to the kidneys function, if any, possibly caused by the experimented US method and/or by the clinical procedure. Urine stick test was performed at the end of each BL or US session, and analyzed levels of: Urobilinogen, Glucose, Bilirubin, Ketones, S.G, Blood, pH, Protein, Nitrite, and Leukocytes. No significant deviation from normal levels was observed by the activation of the US.

In an exemplary pig experiment, at the beginning of each BL (baseline) or US (Ultrasound activation) session, 20 ml of 755 mg/ml of Iohexol was injected for the purpose of Iodine clearance evaluation. Urine samples, taken at each baseline and ultrasound activation session, were analyzed for concentration of Iohexol. Analysis method included taking X-ray images of vials with urine samples (X-ray image taken on frozen vials, positioned with the same height of urine in the vials), evaluating Iohexol concentration according to image intensity in each vial (grey scale, with darker indicating higher iohexol concentration) and scaling the result based on intensity analysis of X-ray images of reference vials having known concentrations of Iohexol.

Analytical Method

Renal Function Measures:

There were estimated the following 5 measures: Urine Flow Rate, GFR (Glomerular filtration rate), Urine Creatinine Clearance Rate, Urine to Blood Creatinine Ratio, Urine Protein to Creatinine Ratio, Urine to Blood Sodium Ratio.

Figure 15:
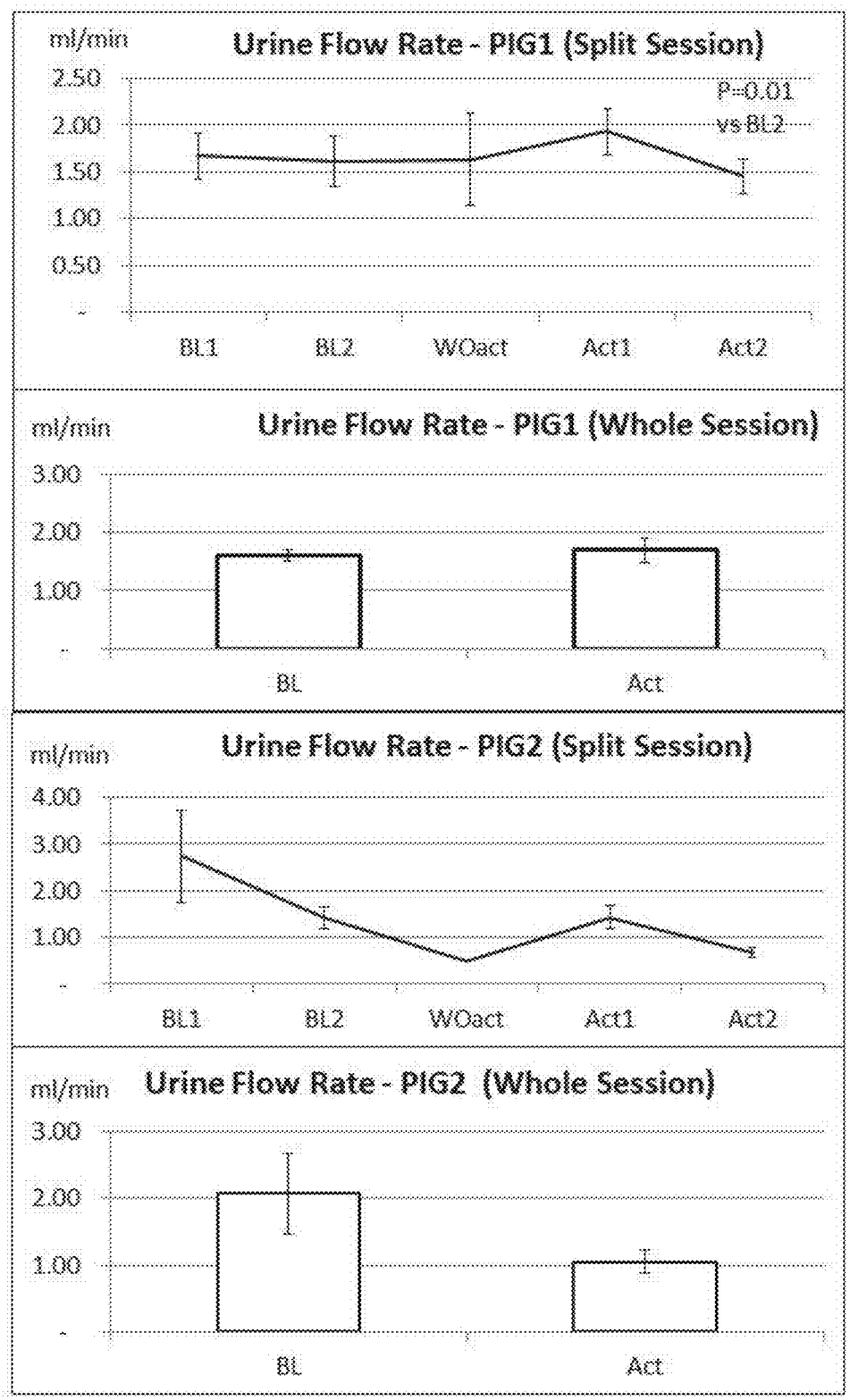
FIG. 15 are graphs showing the urine flow rate of the pigs during the experiments, in accordance with some embodiments of the invention.

1. Urine Flow Rate (see FIG. 15):
Urine flow rate is estimated as the ratio of urine volume excreted in a period of time and the time length of that period:

$$\text{Urine Flow Rate} = \frac{\text{Urine Volume}}{\text{Time}}$$

Figure 16:
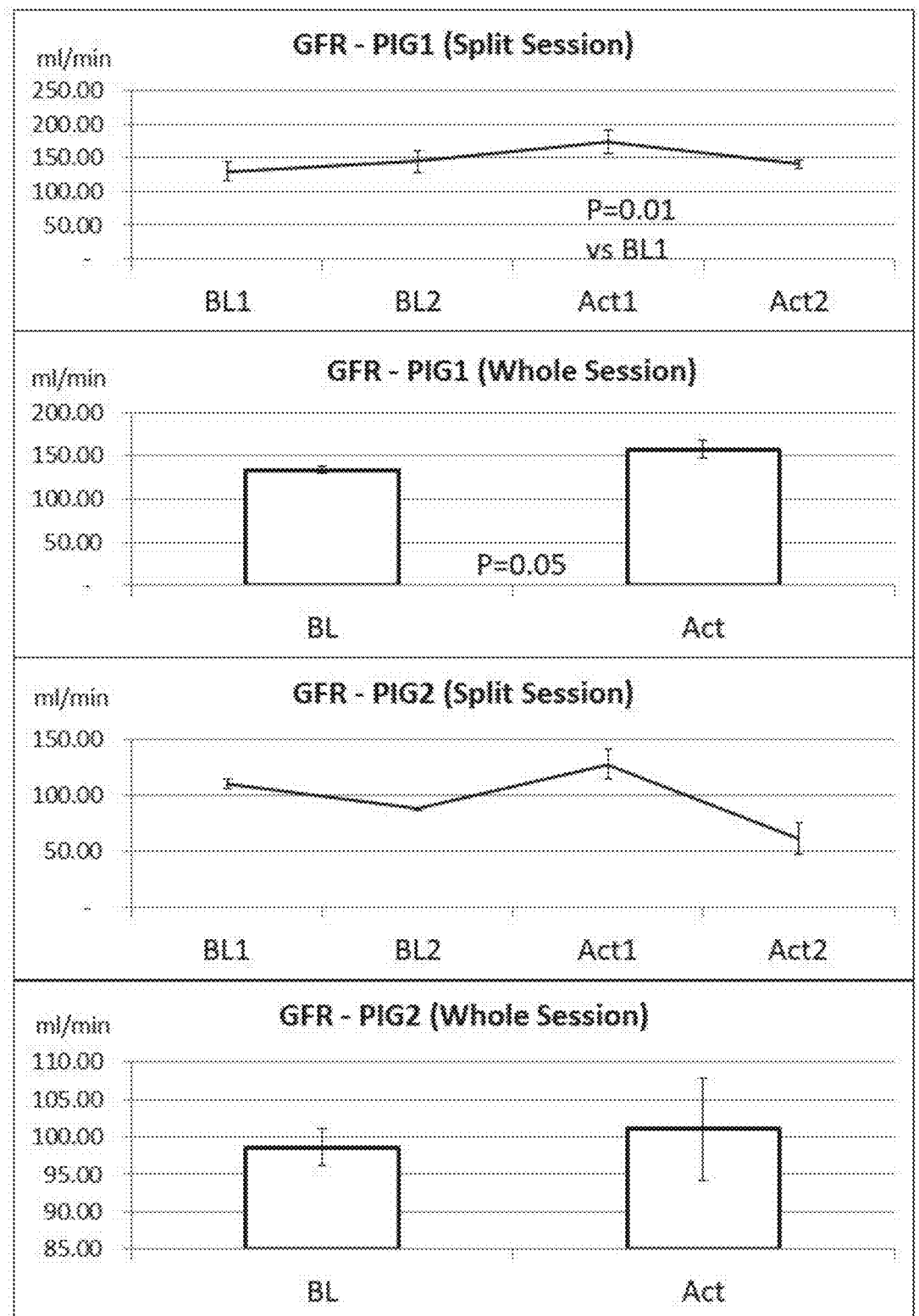
FIG. 16 are graphs showing the GFR of the pigs, in accordance with some embodiments of the invention.

2. GFR (see FIG. 16):
GFR is a measure of renal function. GFR is the volume of fluid filtered from the renal glomerular capillaries into the Bowman's capsule per unit time. In accordance with clinical practice, we estimated GFR by the Creatinine Clearance Rate: Creatinine is produced naturally by the body and is freely filtered by the glomerulus. Although the peritubular capillaries actively secrete Creatinine in small amounts and hence Creatinine overestimates actual GFR by 10% to 20%, this margin of error is considered acceptable. We estimate GFR as the product of urine concentration of Creatinine and urine flow rate (which gives the mass of Creatinine excreted during the time that urine has been collected), divided by the blood concentration of Creatinine:

$$GFR = \frac{\text{Urine Creatinine Concentration} \times \text{Urine Flow}}{\text{Blood Creatinine Concentration}} [\text{mL/min}]$$

Figure 17:
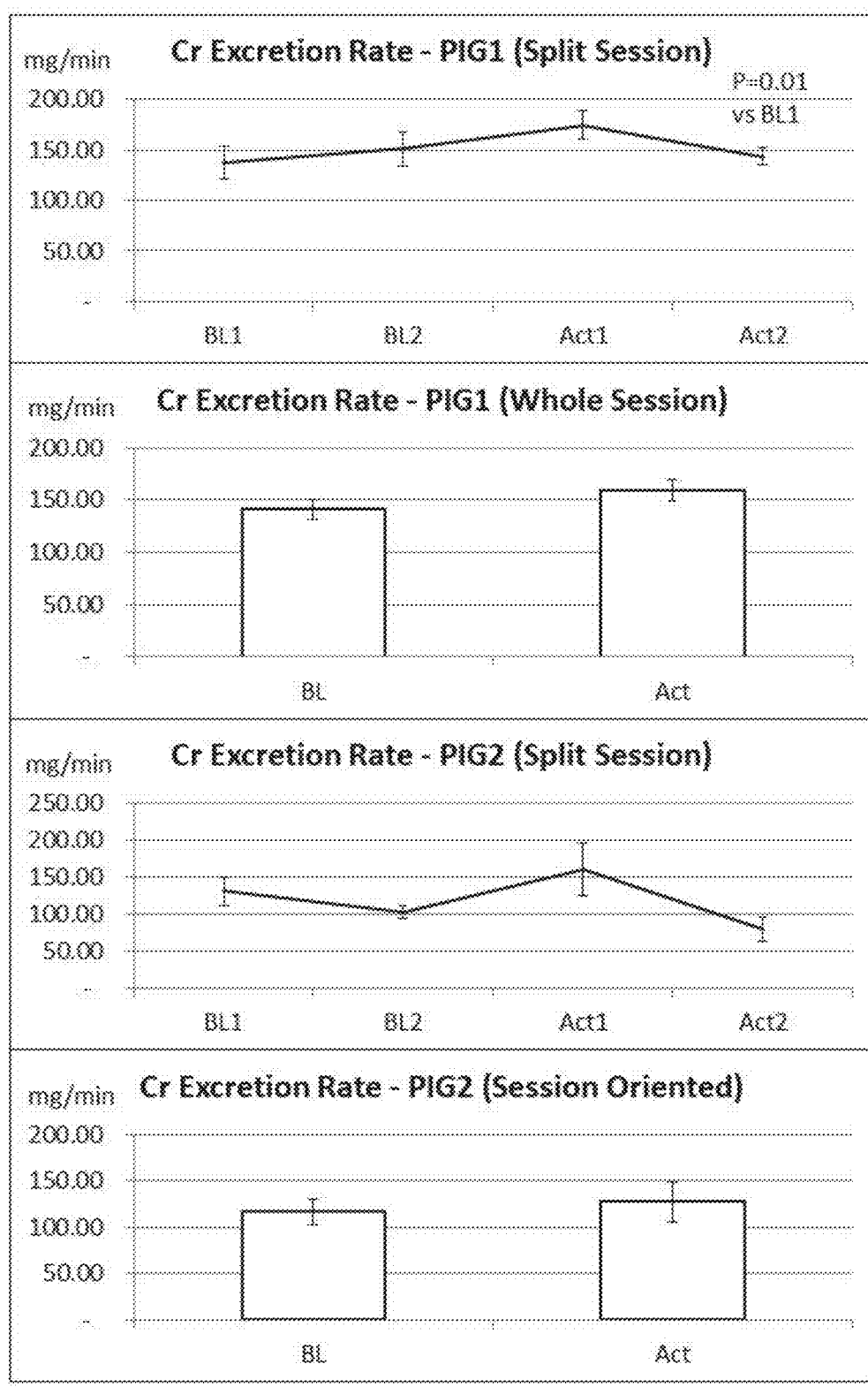
FIG. 17 are graphs showing the urine creatinine clearance rate of the pigs, in accordance with some embodiments of the invention.

3. Urine Creatinine Clearance Rate (see FIG. 17):
Urine creatinine clearance rate is another measure of kidney function and is the product of urine concentration of Creatinine and urine flow rate—which gives the mass of Creatinine excreted during the time that urine has been collected:

Urine Creatinine Clearance Rate=Urine Creatinine Concentration×Urine Flow [gr/min]

Figure 18:
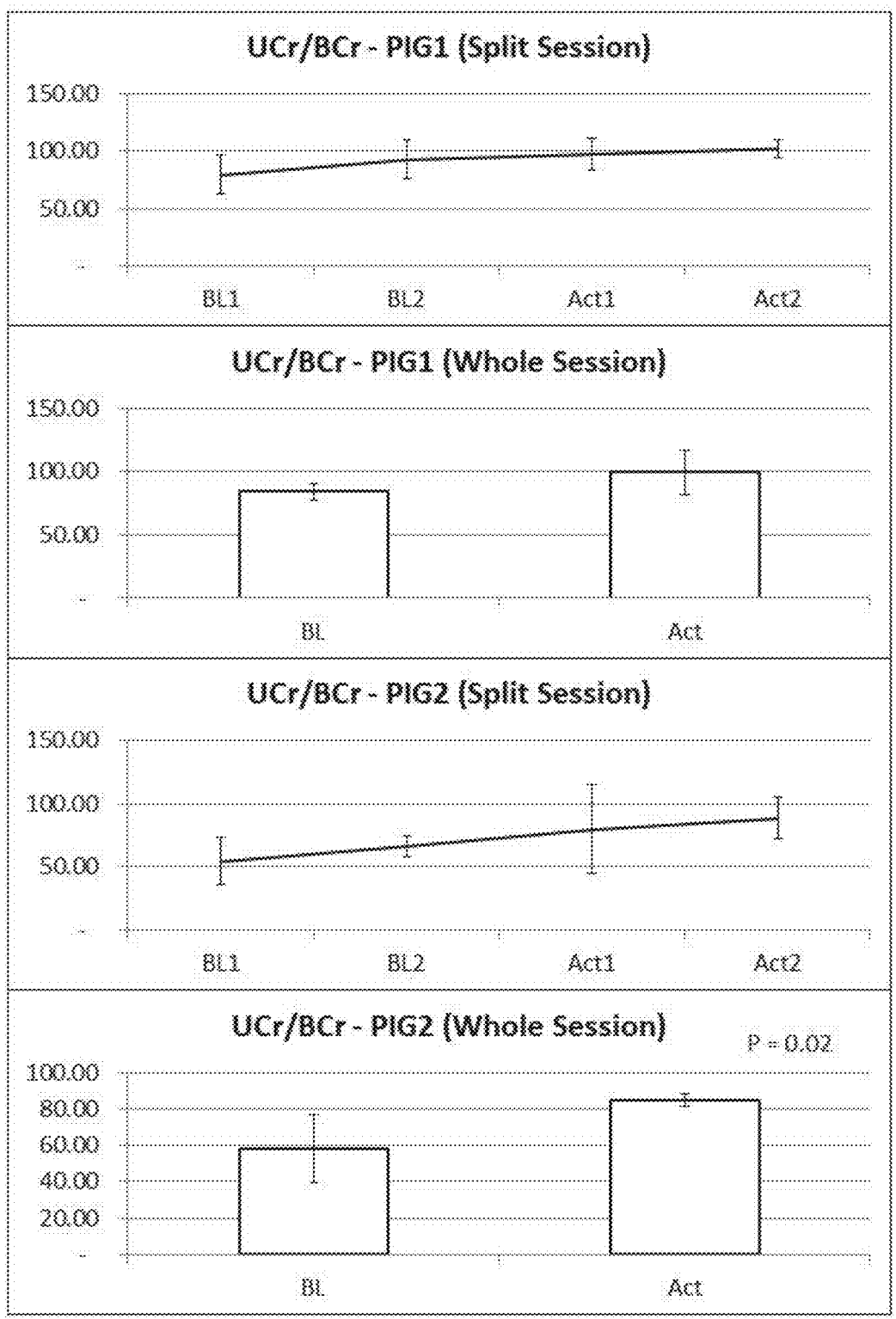
FIG. 18 are graphs showing the urine to blood creatinine ratio of the pigs, in accordance with some embodiments of the invention.

4. Urine to Blood Creatinine Ratio (see FIG. 18):
Another measure of renal function is the Urine to blood creatinine ratio:

$$\text{Urine to Blood Creatinine Ratio} = \frac{\text{Urine Creatinine Concentration}}{\text{Blood Creatinine Concentration}}$$

Figure 19:
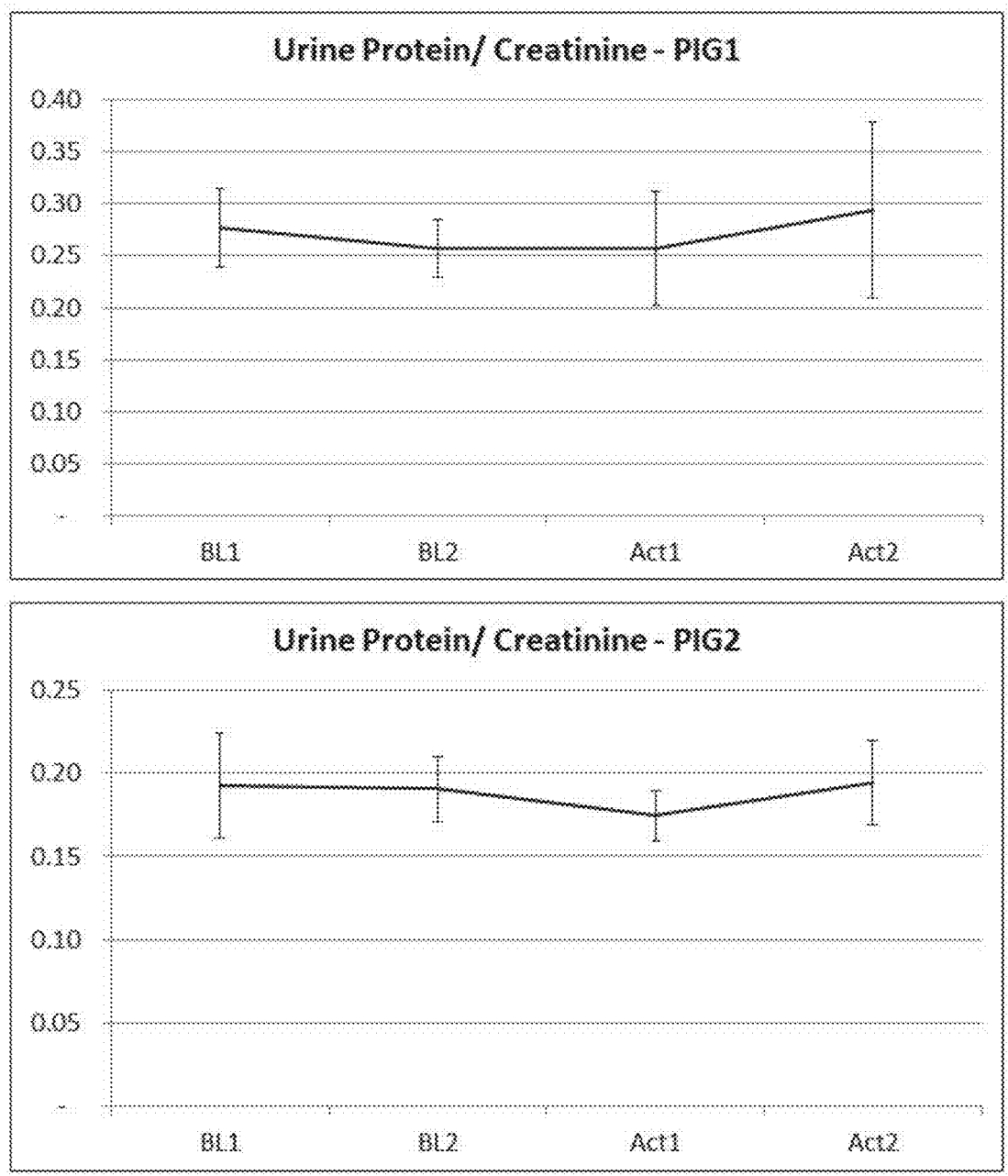
FIG. 19 are graphs showing the urine protein to creatinine ratio of the pigs, in accordance with some embodiments of the invention.

5. Urine Protein to Creatinine Ratio (see FIG. 19):
Protein to Creatinine ration, in the urine, is an indicative of potential damage to the kidneys and is estimated as follows:

$$\text{Urine Protein to Creatinine Ratio} = \frac{\text{Urine Protein Concentration}}{\text{Urine Cretinine Concentration}}$$

Analysis Periods:
Two time periods were used for analysis:
 1. Split Session Analysis (0.5 hour)—in which each measure is estimated per 2 time periods in a session: the 1'st half (between samples 0 end 1) and the 2'nd half (between samples 1 and 2).
 2. Whole Session Analysis (1 hour)—in which each measure is estimated per the entire session—between samples 0 and 2.

Results

The experiment was performed in healthy animals with healthy kidneys. PIG-1 was with good hydration condition over many hours of anesthesia, while PIG-2 was on a course of continuous slow dehydration (except for bolus of fluids that was provided once during the experiment). Generally speaking, the animals were stable throughout many hours of anesthesia. As shown by the results, shown in FIGS. 15-19, in all cases it is apparent that there is a delayed response, by about 15-45 min in elevation of urine output flow as observed through urine collected by Foley catheter (could be that some delay is due to the flow through the urethra, bladder and urethral catheter). The elevation in urine output is statistically and clinically significant relative to the corresponding baseline levels. The elevation was repeated consecutively, thus the effect is reproduced, with no residual damage. Interestingly, and as may potentially be expected in healthy animal with healthy kidneys, the effect was reduced after about 60 minutes, suggesting that the body could act to preserve fluids in response to the elevated urine output due to the treatment in the 30 min beforehand. This phenomena repeated again and again, suggesting that it is real, and that the kidneys maintain their normal function and fluid control capabilities.

Glomerular filtration rate was elevated by the treatment in statistically and clinically significance, in the same manner as the elevation in urine output flow.

Likewise, Creatinine clearance rate were elevated by the treatment, as well as ability to clear iohexol by the kidney.

No signs of damage were apparent by Urine protein/Creatinine ration throughout the experiment. No sign of material damage were apparent in Urine sticks evaluation, and no signs of meaningful heating or cavitation damage were observed in histo-pathology.

Figure 20:
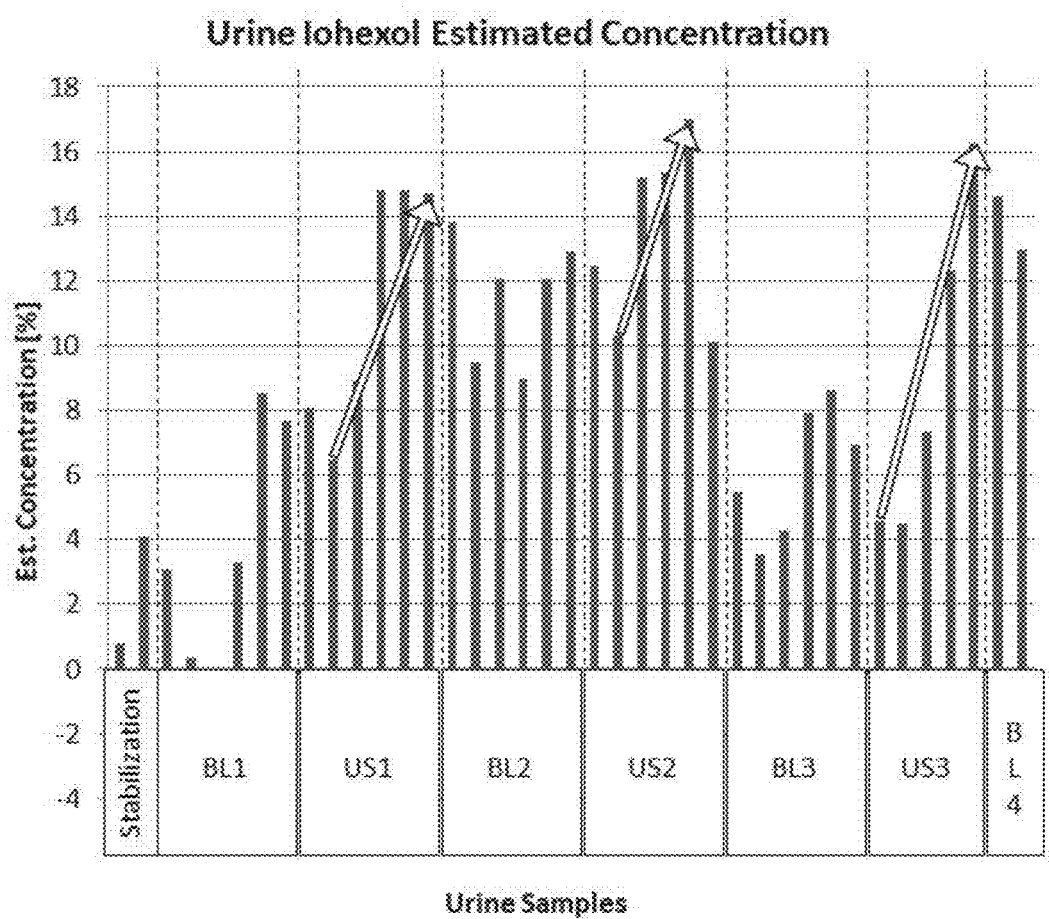
FIG. 20 is a graph showing an estimation of Iodine concentration in urine during the experiment, in accordance with some embodiments of the invention.

The results of the analysis on PIG-2 experiment—presented for example in the graph in FIG. 20—provide an estimation of Iodine concentration in urine, during the experiment. Arrows in the graph indicate on significant increase in Iodine concentration in the urine, during the ultrasound activation sessions, compared to the preceding baseline sessions, which is indicative of improved Iodine clearance. It may be appreciate by a person skilled in the art that improved contrast-media clearance may be potentially associated with better tolerance of the kidneys to the nephrotoxic effect of the contrast media, and therefore potentially useful for prevention or reduction of Contrast Induced Nephropathy (CIN). Therefore, in some exemplary embodiments of the present invention the system is used before a procedure that involves use of contrast media, in some exemplary embodiments of the present invention the system is used during a procedure that involves use of contrast media, and in some exemplary embodiments of the present invention the system is used after a procedure that involves use of contrast media, for example when the amount of contrast media that was injected was higher than a certain threshold (e.g. more than 200 ml of iohexol) and/or when biomarkers appear to be indicative of potential damage (e.g. elevated serum creatinine, and/or elevated NGAL values, and/or elevated Nephrocheck levels and/or substantial reduction in urine output) and/or when the patient is considered to be at high risk of developing CIN and/or AKI and/or ATN already prior to the procedure and/or due to steps that occurred during the procedure.

Rat Experimental Study

The purpose of the experiment is to evaluate the effect of low intensity ultrasonic energy (LIU) on the formation, protection and recovery from AKI/ATN (a.k.a. acute renal failure/acute kidney injury/acute tubular necrosis).

The reported procedures, performed in animals, were authorized by the Council for Experiments in Animals. About 30 Sprague Dawley rats, male, mean weight of about 350 gr were used. At each time point blood vials of about 200 uL were collected. Two/One/None Urine vials (up to 100 uL each) were collected according to availability by the animal. All samples were centrifuged before freezing. All samples were sent to a blinded lab (AML—American Medical Labs) for analysis as a single batch.

AKI/ATN model: AKI/ATN is induced by ischemic reperfusion, using simultaneous clamping of renal arteries on both sides for 45 minutes.

Animal Preparation

Anesthesia: AKI/ATN induction and treatments are done during 3-4 hours of anesthesia using isoflurane (about 1%).

Sonication Methods

LIU Treatment:

Mode 1: delivery for about 3 hours, in the range of 5-8 MHz (fixed probe location, curved probe), MI=0.3, in direct contact (zero distance) to tissue, intermittently changing between left and right kidney every 5 minutes.

Mode 2: beginning of treatment delayed for 24 after beginning of ischemia, then delivery for about 3 hours, in the range of 5-8 MHz (fixed probe location, curved probe), MI=0.3, in direct contact (zero distance) to tissue, intermittently changing between left and right kidney every 5 minutes.

Mode 3: delivery for about 3 hours, in the range of 6-13 MHz (high frequency, fixed probe location, curved probe), MI=0.6, in direct contact (zero distance) to tissue, intermittently changing between left and right kidney every 5 minutes.

Mode 4: left kidney only, continuous delivery for about 1 hours, in the range of 5-8 MHz (fixed probe location, curved probe), MI=0.3, in direct contact (zero distance) to tissue.

Mode 5: right kidney only, continuous delivery for about 1 hours, in the range of 6-13 MHz (high frequency, fixed probe location, curved probe), MI=0.6, in direct contact (zero distance) to tissue.

Mode 6: left kidney only, continuous delivery for about 4.5 hours, in the range of 5-8 MHz (fixed probe location, curved probe), MI=0.3, in direct contact (zero distance) to tissue.

Mode 7: right kidney only, continuous delivery for about 4.5 hours, in the range of 6-13 MHz (high frequency, fixed probe location, curved probe), MI=0.6, in direct contact (zero distance) to tissue.

Experiment Timeline

Study Design:
1. Sham operated normal control (no AKI/ATN)
2. Immediate treatment: 3 h treatment immediately after AKI induction (Mode 1)
3. Delayed treatment: 3 h delayed treatment, at 24 h and at 48 h after AKI induction (Mode 2)
4. AKI with sham treatment
5. More cases and other treatment configuration arms to be evaluated at next stage (Modes 3-7)

Follow-up time points: (T=0 is start of AKI induction by renal ischemia): pre-induction (baseline), 1 h, 6 h, 23 h, 48 h, 72 h, 1 wk, 2 wk.

Endpoints:
1. Primary (for efficacy and safety): Blood (serum) Creatinine level
2. Secondary: Blood (serum) Urea level
3. Secondary: histopathology—evaluating casts formation or major tissue damage
4. Tertiary: other blood and urine values, if available (e.g. serum Na, serum K, Urine Protein/Creatinine, Urine Creatinine, Urine Protein, Urine NGAL), weight and average water consumption per group.

Measurements

Analysis: The endpoints would be compared between the groups with a focus evaluating the immediate treatment method (for potential prevention or amelioration of AKI development)

Comparison at each time point shall be between all available data of the treated group vs. all available data in normal-control cases, and vs. all available data among the groups with non-treated-AKI cases at that time point.

For example, in analysis of data for non-treated cases: up to 24 h the data is from 6 animals (groups 3 and 4 were not treated during the first 24 h) and afterwards it is from 3 animals (group 4)

Analysis was evaluated per time point mean over the cohort of absolute changes in the values of the endpoint at the time point, and shall evaluate mean over the cohort of relative changes from baseline per case (i.e. mean over the cohort of each case, % change from baseline to a certain time point).

Data Exceptions: Cases that cannot tolerate the procedure (due major complication or death) or the prolonged anesthesia will be excluded from analysis, or their data be used only to the extent it is reliable (e.g. before major complication or severe deterioration which is not reasonably associated with the evaluated treatment)

Results

Figure 21:
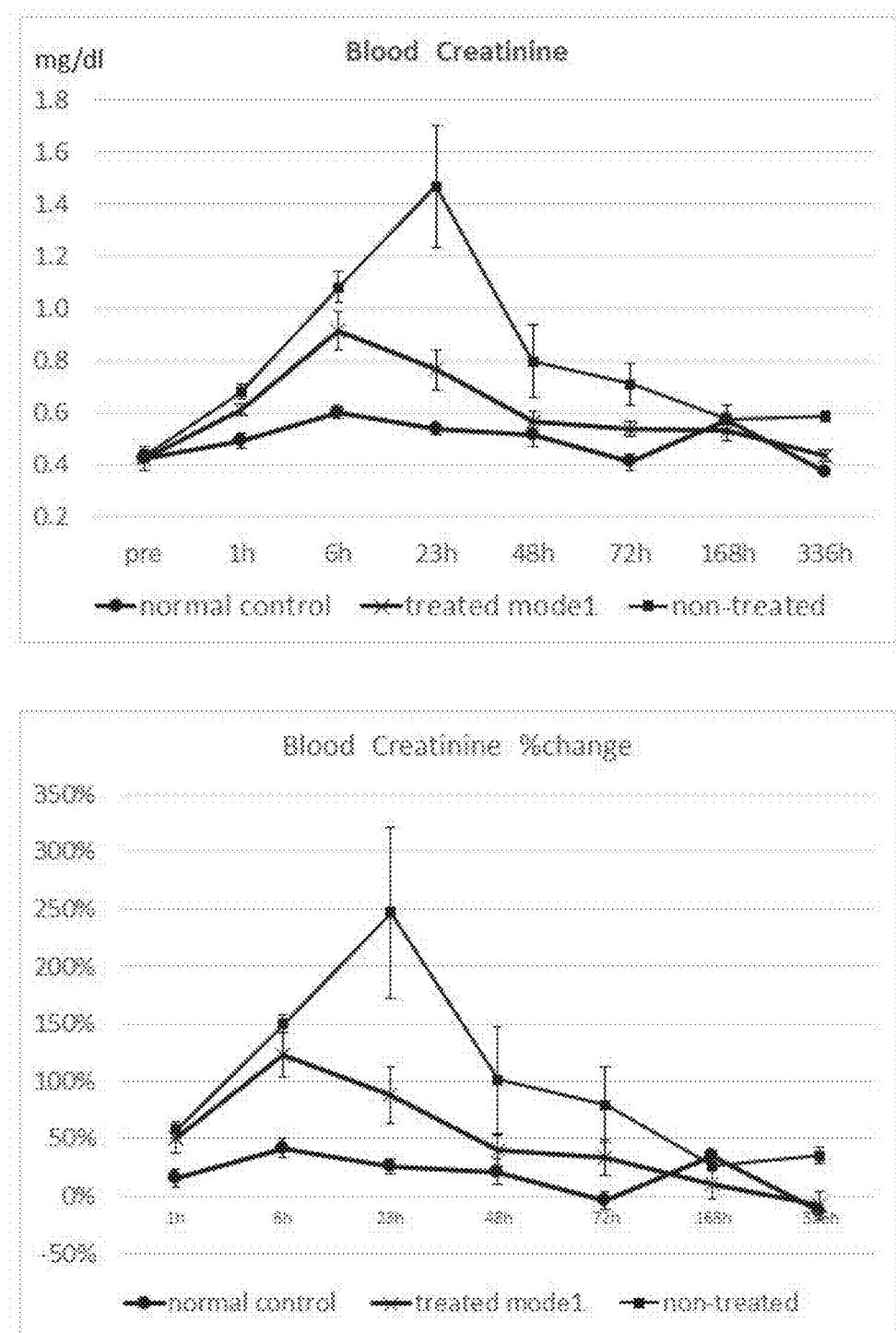
FIG. 21 are graphs showing the creatinine levels in the blood and the percentage of change creatinine levels in the blood of the rats, in accordance with some embodiments of the invention.

FIG. 21 show the creatinine levels in the blood and the percentage of change in the creatinine levels in the blood, in three experimental groups (control, treated with Mode 1 and non-treated). As can be seen in the graphs, the levels of Creatinine the in blood of the treated rats show great improvement in comparison to the non-treated rats.

Figure 22:
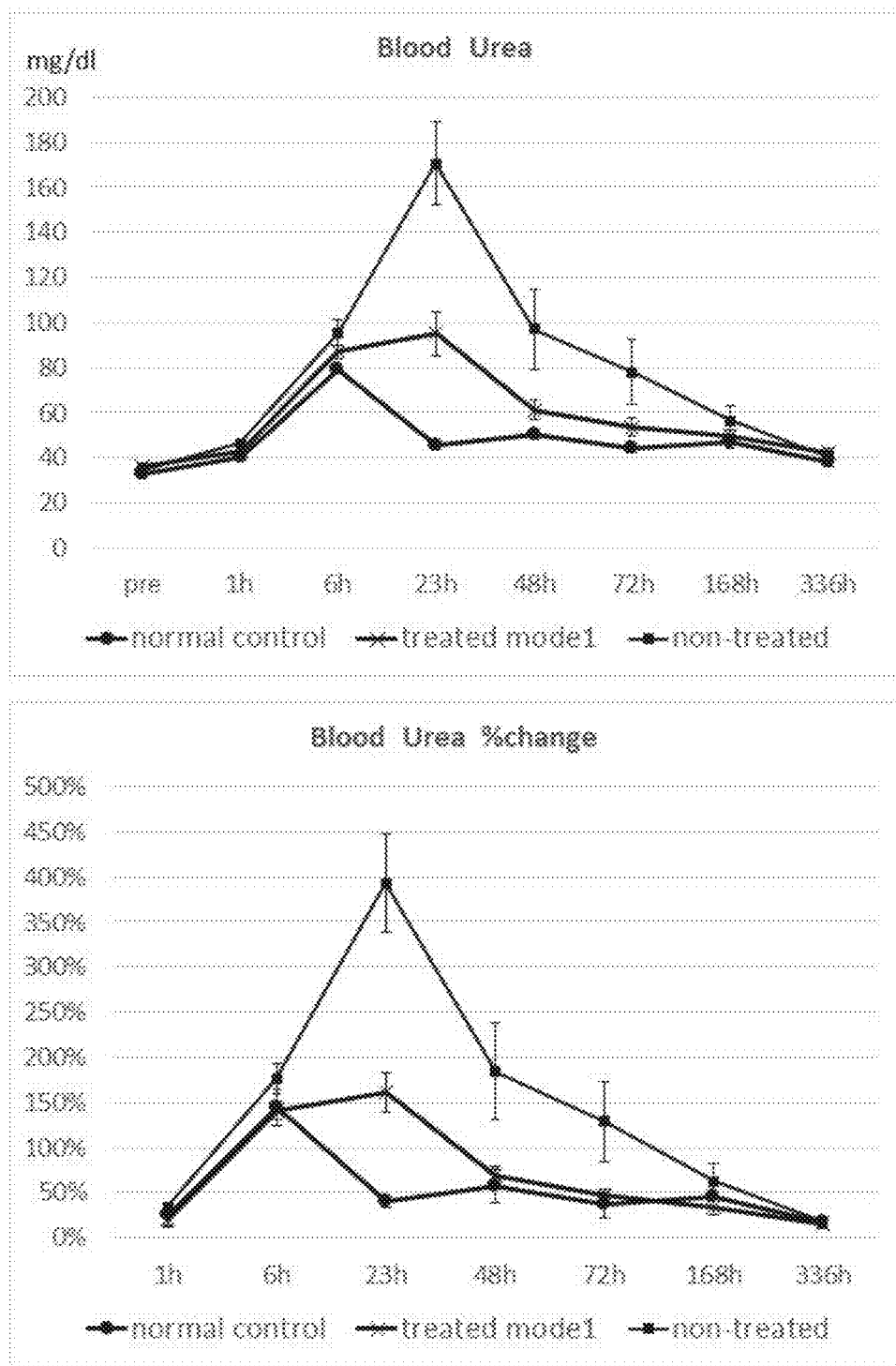
FIG. 22 are graphs showing the urea levels in the blood and the percentage of change urea levels in the blood of the rats, in accordance with some embodiments of the invention.

FIG. 22 show the urea levels in the blood and the percentage of change in the urea levels in the blood, in three experimental groups (control, treated with Mode 1 and non-treated). As can be seen in the graphs, the levels of urea in the blood of the treated rats show great improvement in comparison to the non-treated rats.

Figure 23:
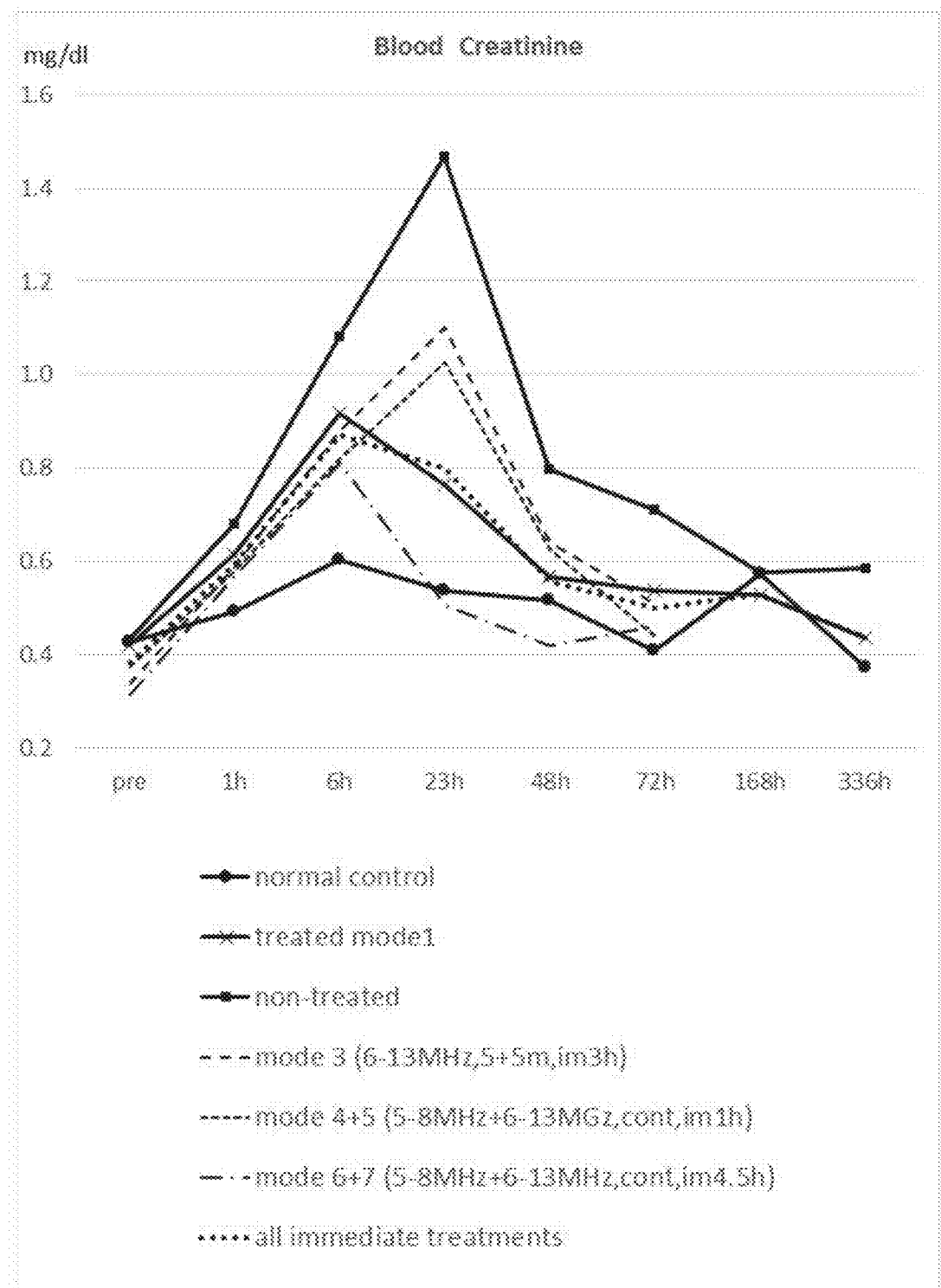
FIG. 23 is a graph showing the creatinine levels in the blood in seven experimental groups, in accordance with some embodiments of the invention.

FIG. 23 show the creatinine levels in the blood in seven experimental groups (control, treated with Mode 1, non-treated, treated with Mode 3, treated with Mode 4 and 5, treated with Mode 6 and 7, and a collection of all immediate treatments (not delayed)). As shown before, the levels of Creatinine in the blood of the treated rats show great improvement in comparison to the non-treated rats. Interestingly, Modes 4+5 showed a higher improvement in relation to the results of Mode 1 and Mode 3. Indicating that a longer period of treatment is better than a shorter one, and that the range of frequency 5-8 MHz is better than the range of frequency 6-13 MHz.

Figure 24:
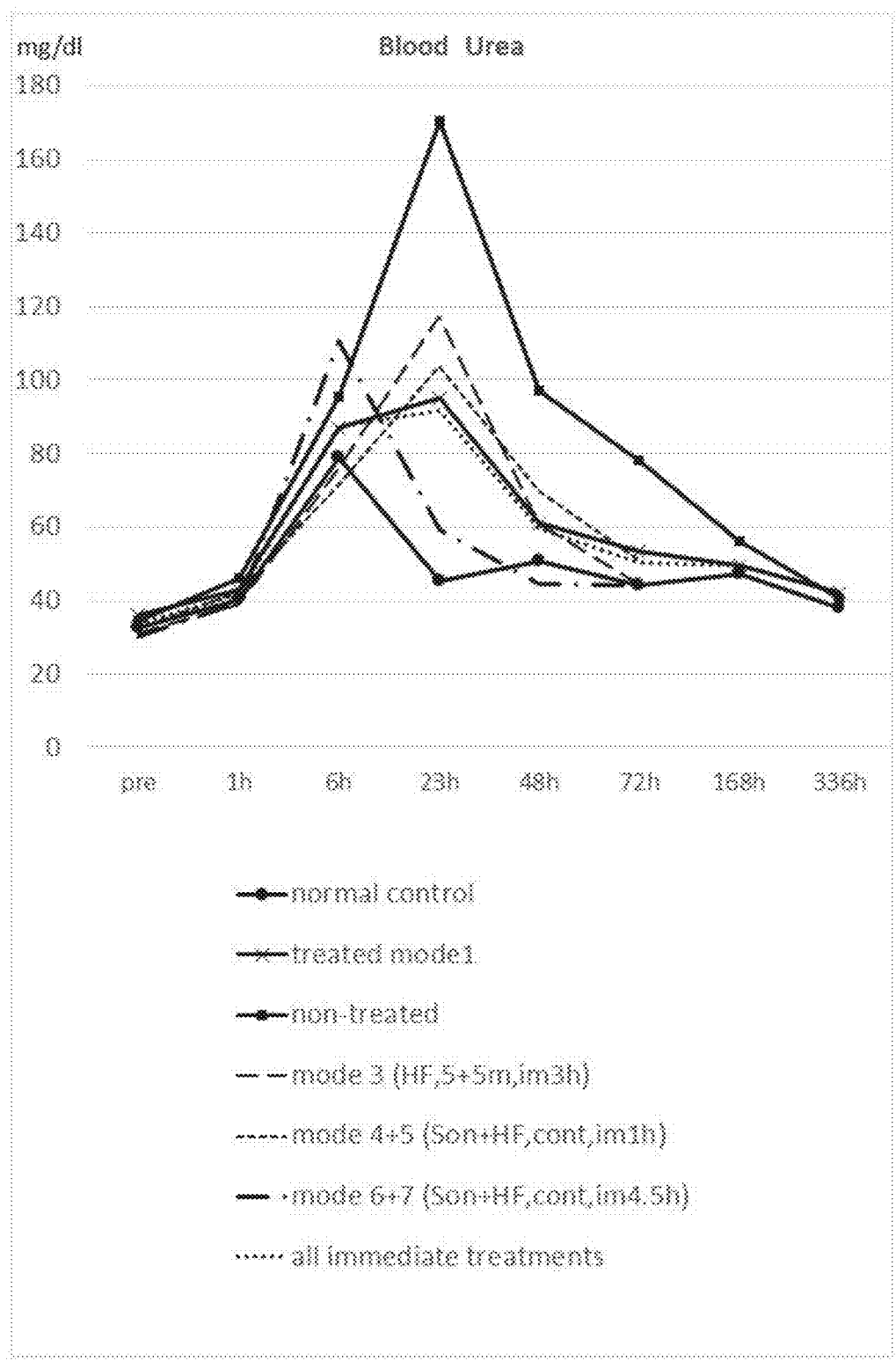
FIG. 24 is a graph showing the urea levels in the blood in seven experimental groups, in accordance with some embodiments of the invention.

Similar results can also be seen, for example, in FIG. 24, showing the urea levels in the blood of the same groups described in FIG. 23.

Figure 25:
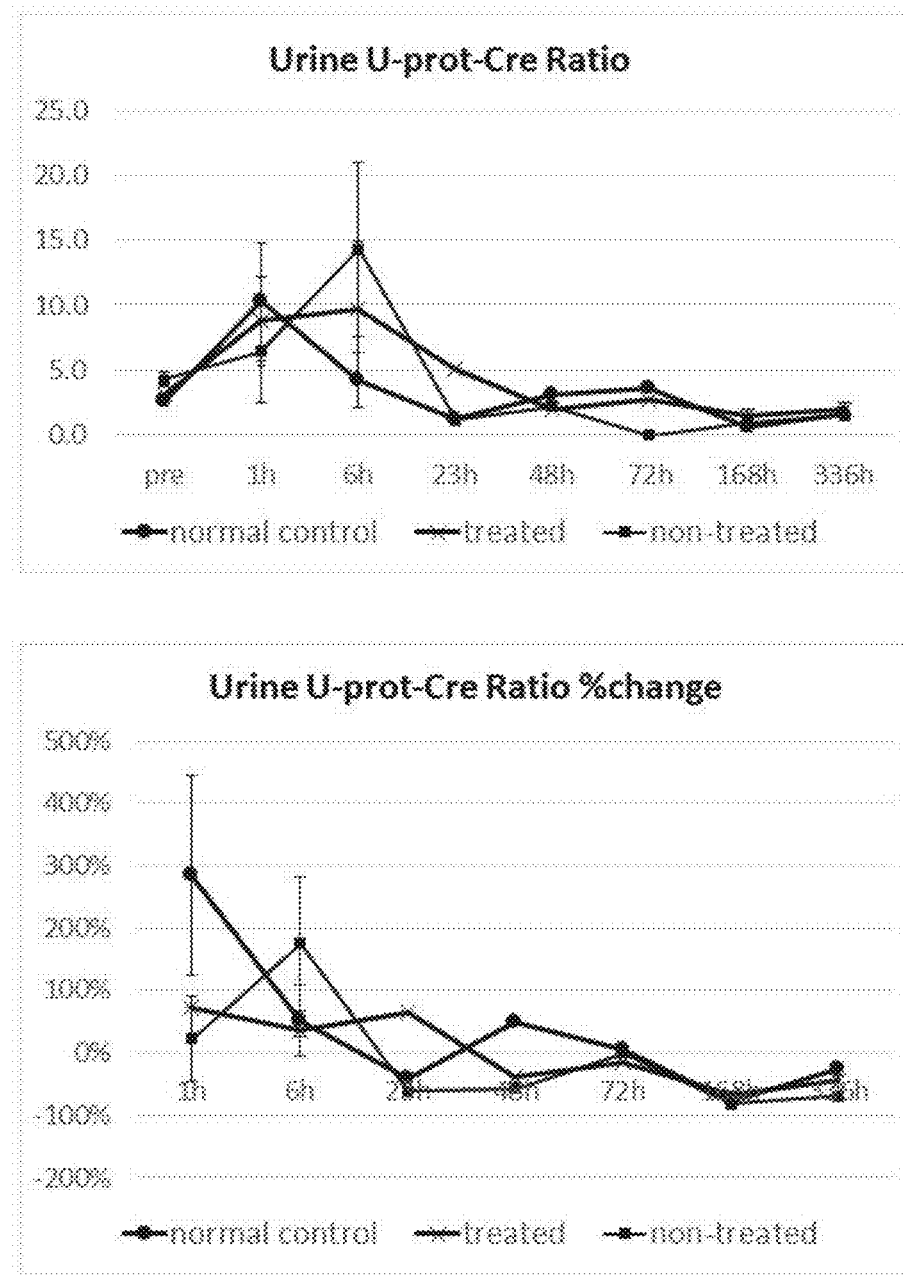
FIG. 25 are graphs showing the protein/creatinine levels in the urine and the percentage of change protein/creatinine levels in the urine of the rats, in accordance with some embodiments of the invention.

FIG. 25 show the Protein/Creatinine in the urine and the percentage of change in the Protein/Creatinine levels in the urine, in three experimental groups (control, treated with Mode 1 and non-treated). Also here, the levels of Protein/Creatinine the in urine of the treated rats show improvement in comparison to the non-treated rats.

Histopathology Observations

Based on histology scoring system (adapted from Khalid et al, Whalena H et al and Melnikov et al), scores of total damage are provided in the range of 0 (normal) to 14 (severe damage) as a sum of scores for Tubular, Endothelial, Glomerular, and Tubulointerstitial tissue for each observed kidney, as shown in the table below:

| Group (6 kidneys per group) | Total Damage Score (P vs. treated group) | Total Damage Score (P vs. treated group) | Glomerular Damage |
|---|---|---|---|
| Normal control | 0.33 ± 0.52 ($P < 0.01$) | 0.33 ± 0.52 ($P = 0.01$) | 0.0 |
| Treated ATN | 2.67 ± 0.82 | 1.17 ± 0.41 | 0.5 ± 0.55 |
| Non-Treated ATN | 4.33 ± 1.03 ($P = 0.01$) | 2.17 ± 0.75 ($P = 0.02$) | 0.83 ± 0.41 |

Figure 26:
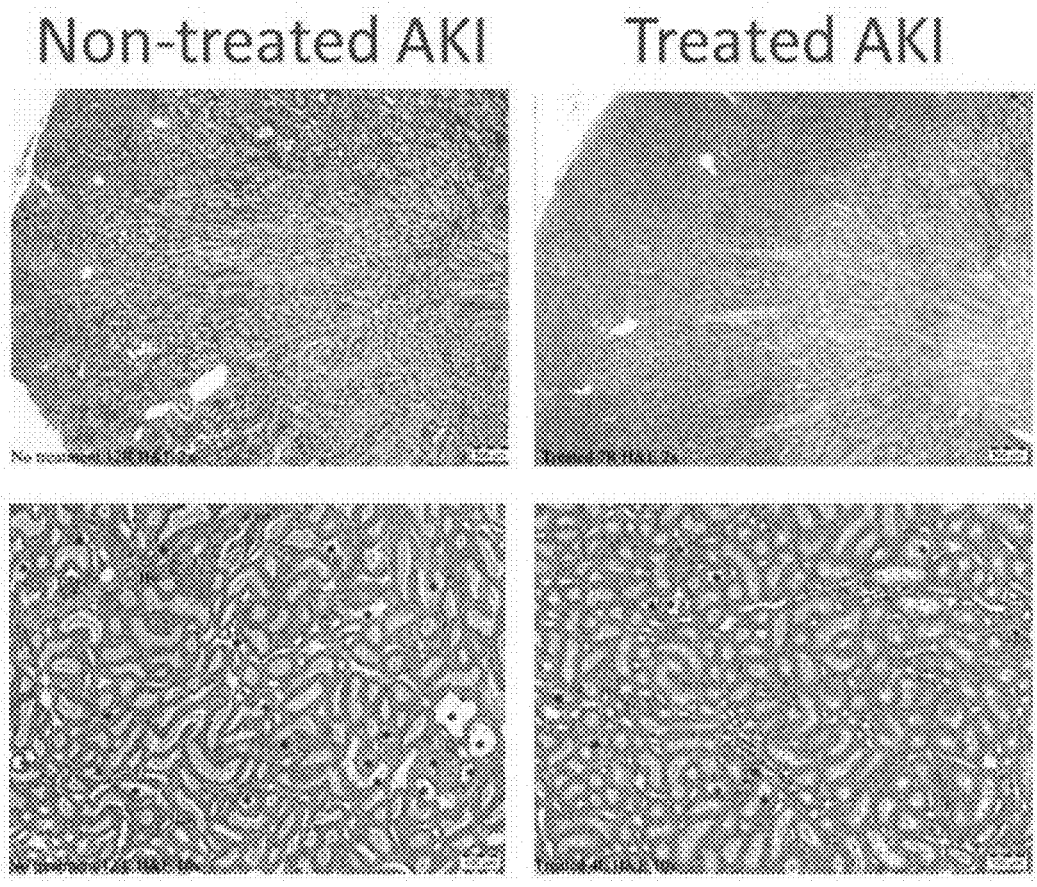
FIG. 26 are histology results of the experiments with the rats, in accordance with some embodiments of the invention.

Results show an apparently lower score in ATN treated kidneys vs. ATN non-treated kidneys, as can be seen in FIG. 26.

The findings suggest slightly faster or more complete tubular regeneration in the treated samples vs. non treated samples as the tubular score seems lower in the treated samples.

There was no evidence of thermal damage, cavitation or necrosis in any of the kidneys examined.

Figure 27:
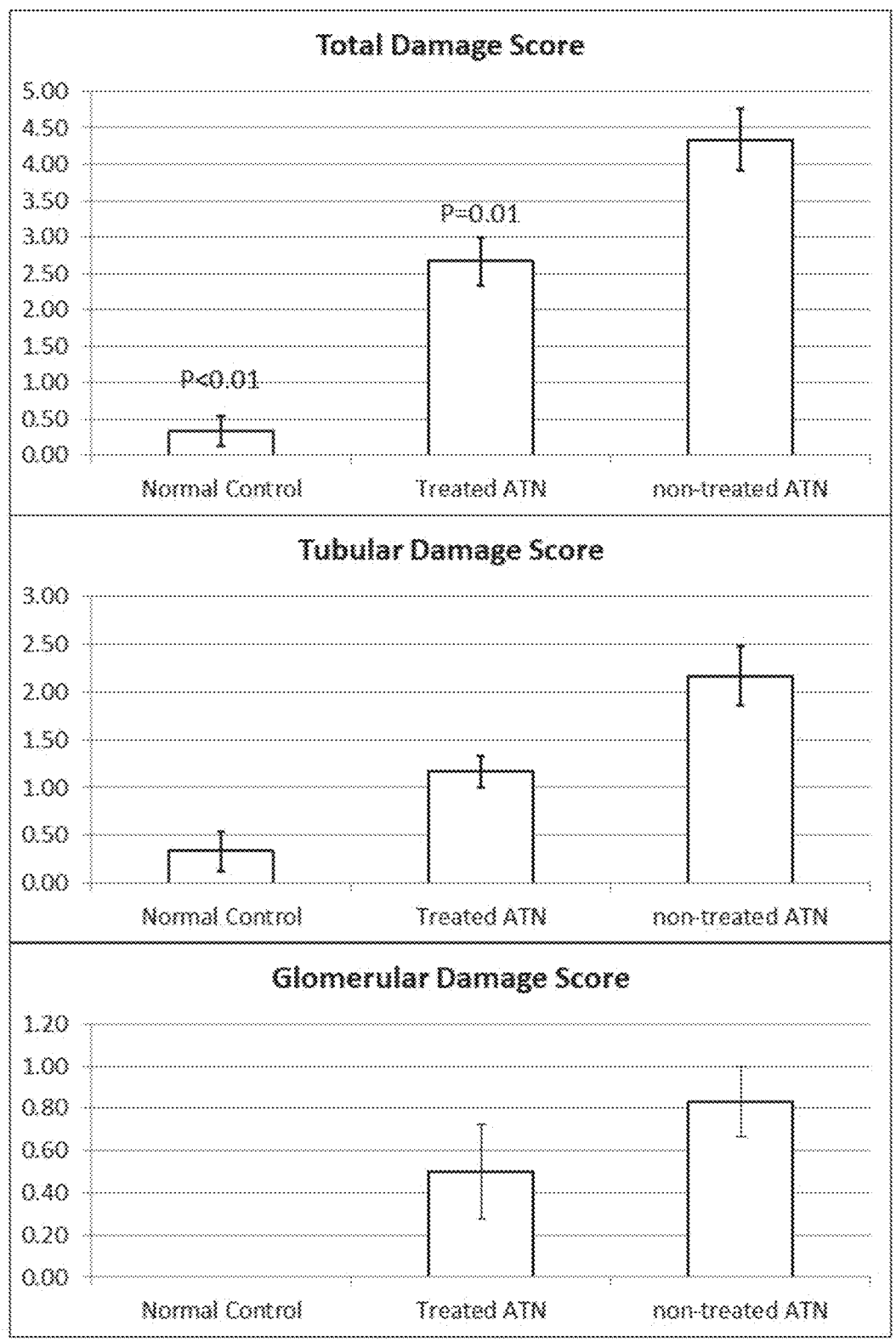
FIG. 27 are graphs showing the different damage levels in the rats, in accordance with some embodiments of the invention.

Score of extent of tubular regeneration appears lower in the treated samples, suggesting either slightly decrease in lesions or faster recovery of the renal parenchyma, as shown in FIG. 27.

Marked increased basophilia in kidney 12R (total score 6), on the left, when compared to kidney 7R (total score 4) on the right.

Normal tubules are bright pink and homogeneous. Regenerating tubules have increased basophilia, (bluer), tubular epithelial cells. The cells are generally attenuated (flattened), so that the tubular lumens look dilated.(*)

Non-treated (12L): It is estimated that the regenerating tubules are slightly above 50% when compared to the normal tubules, score 3. There is also minimal interstitial fibrosis (IF).

Treated (4L): It is estimated that the regenerating tubules are less than 25% of the parenchyma in this sample, score 1.

Conclusion

In these rats, 45 min ischemia simultaneously applied to both kidneys successfully induced active ATN/AKI for at least 24 hours, with recovery phase starting during 24-48 hours.

LIU applied immediately over 3 hours successfully blunted the ATN/AKI development, showing clear reduction the build-up of Blood Creatinine and Urea levels, and faster recovery to normal levels, as shown in FIGS. 21-24.

There is an indication that LIU applied at longer periods of time, in a continuous manner, at a frequency from about 5 MHz to about 8 MHz, provide better results. It is obvious from the results, that using the other parameters also provided better results, when compared with the non-treated group.

Based on blood and urine samples, no negative impact or damage was identified, for example, by observing Urine Protein/Creatinine ratio (see FIG. 25).

Histological analysis suggests slightly faster or more complete tubular regeneration in the treated samples vs. non treated samples, and either slightly decrease in lesions or slightly faster recovery of the renal parenchyma, with no residual damage due to treatment (see FIGS. 26-27).

Based the observations that suggest better and/or improved and/or faster and/or more complete regeneration and/or better preserved structure by the treatment, it is hypothesized that the treatment potentially triggers hormonal changes, and/or neuronal response, and/or reno-renal reflex, and/or modulation of activity in the stretch receptors within the kidney, some of which may be associated with triggering or modulating regeneration processes.

It is expected that during the life of a patent maturing from this application many relevant irradiation techniques and transducers will be developed; the scope of the term irradiation is intended to include all such new technologies a priori.

As used herein with reference to quantity or value, the term "about" means "within ±10% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a kidney, modifying kidney function, preventing kidney dysfunction or preventing deterioration of kidney function, said method is performed while excluding the use of any microbubble contrast material, the method comprising:
   emitting a quantity of ultrasound energy to at least a portion of a kidney at a frequency, pulse shape, pulse duration, repetition rate and amplitude suitable to affect kidney function in at least a portion of said kidney;
   repeating said emitting for at least 30 minutes;
   wherein said emitting does not induce substantial thermal damage or cavitation damage to tissues in the patient's kidney;
   wherein said frequency of most of said ultrasound energy is at a frequency higher than 5 Megahertz (MHZ);
   wherein said emitting said quantity of ultrasound energy comprises emitting ultrasound energy having a mechanical index below 1.0.

2. The method according to claim 1, wherein more than 80% of said ultrasound energy is emitted at said frequency.

3. The method according to claim 1, wherein said emitting is repeated for at least 1 hour.

4. The method according to claim 1, wherein during said emitting a thermal index soft tissue or thermal index bone lower than 1.0 is kept.

5. The method according to claim 1, wherein said emitting comprises emitting at a main frequency selected to have a wavelength of a size or harmonic of a nephron structure of said kidney to be affected.

6. The method according to claim 1, wherein said pulse duration is from about 0.1 microsecond to about 100 microseconds.

7. The method according to claim 1, wherein said pulse duration is from about 0.1 microsecond to about 20 microseconds.

8. The method according to claim 1, wherein said emitting is performed for a period of time from about 1 hour to about 24 hours.

9. The method according to claim 1, wherein said emitting is performed daily.

10. The method according to claim 1, wherein said emitting is performed for a period of time from at least 3 hours.

11. The method according to claim 1, wherein said emitting is performed intermittently.

12. The method according to claim 1, wherein said affected kidney function comprises blood pressure.

13. The method according to claim 1, wherein said affected kidney function comprises at least one of metabolic activity and hormone secretion.

14. The method according to claim 13, wherein a rate of creation of at least one metabolite is changed by at least 10% on the average for 10 minutes.

15. The method according to claim 1, wherein said affected kidney function comprises clearance of previously injected contrast material for imaging procedures and/or iodine; and
   wherein at least one of the following is true:
   a. at least 10% of said previously injected contrast material for imaging procedures and/or iodine is excreted into urine during up to 24 hours from when said irradiating starts;
   b. at least 50% of said previously injected contrast material for imaging procedures and/or iodine is excreted into urine during up to 24 hours from when said irradiating starts;
   c. at least 50% of said previously injected contrast material for imaging procedures and/or iodine is excreted into urine during up to 4 hours from when said irradiation starts;
   d. a degree of kidney dysfunction caused by said previously injected contrast material for imaging procedures and/or iodine is reduced by at least 10%, as measured after 24 hours; and
   e. a degree of kidney dysfunction caused by said previously injected contrast material for imaging procedures and/or iodine is reduced by at least 10% relative to anticipated degree of kidney dysfunction, as measured after 24 hours.

16. The method according to claim 1, wherein said irradiation is synchronized to at least one selected from the group consisting of:
   a. a cardiac cycle;
   b. a cardiac systole;
   c. a cardiac diastole;
   d. a change in blood flow to an irradiated kidney;
   e. an arrival of a pulse wave to a part of said kidney; and
   f. detected changes in rate of urine output.

17. The method according to claim 1, wherein said emitting is intermittent between multiple independently transmitting transducers.

18. The method according to claim 1, wherein said emitting is activated when at least one monitored parameter arrives at a certain threshold.

19. The method according to claim 18, wherein said monitored parameters are selected from a group consisting of: decreased urine output, increase of creatinine and/or urea in the blood, increase of KIM-1, increase of neutrophil gelatinase-associated lipocalin (NGAL) in the urine, and/or increase of TIMP-2 and IGFBP-7 in blood, and any combination thereof.

20. The method according to claim 18, wherein said emitting reduces a quantity of said monitored parameters in said subject.

21. The method according to claim 18, further comprising identifying a renal artery and measuring one or more of renal artery blood flow, peak flow velocity and pulsatility index in a renal artery.

22. The method according to claim 1, wherein said emitting is activated after a subject has suffered at least one traumatic event selected from the group consisting of: sepsis, heart problems, hemorrhagic shock, hypovolemic shock, liver failure, and any combination thereof.

23. The method according to claim 1, wherein said emitting is activated when a subject shows at least one of the following parameters: a GFR below 40 ml/min, a NGAL of above 100 ng/ml, a Serum Creatinine of above 1.2 mg/dl, and any combination thereof.

24. The method according to claim 1, wherein said emitting is activated when a subject shows an onset of an acute heart failure episode, when said subject shows at least one of the following parameters: a GFR below 40 ml/min, a NGAL of above 100 ng/ml, a Serum Creatinine of above 1.2 mg/dl, and any combination thereof.

25. The method according to claim 1, wherein said emitting is activated on a subject at one or more of before, during and after an interventional procedure or a cardiac surgery, when said subject shows at least one of the following parameters: a GFR below 40 ml/min, a NGAL of above 100 ng/ml, a Serum Creatinine of above 1.2 mg/dl, and any combination thereof.

26. The method according to claim 1, wherein said emitting said quantity of ultrasound energy comprises emitting a continuous waveform of ultrasound energy.

27. The method according to claim 26, wherein said continuous waveform of energy is delivered for at least 1 hour.

28. The method according to claim 1, further comprising monitoring of a location of said kidney and further comprising modifying an orientation of said emitting according to a result of said monitoring of said location of said kidney.

29. The method according to claim 1, further comprising monitoring a movement of said patient during said emitting and further comprising modifying said emitting according to a result of said monitoring of said movement of said patient during said emitting.

30. The method according to claim 1, further comprising automatically moving and orienting said ultrasound energy to kidney regions relative to a location of a renal artery according to a signal provided by at least one sensor.

31. The method according to claim 1, further comprising utilizing information of location of tissues in the kidney and/or in the vicinity of the kidney for the activation and/or deactivation of the apparatus in the kidney.

32. The method according to claim 31, wherein said locations are locations of one or more of bones and other organs.

33. The method according to claim 1, wherein said type of information comprises one or more of estimation of distance to said kidney, Doppler effect flow velocities within a sonicated space, organ edge detection, automatic organ classification, detection of gas/air pockets in different organs, detection of lack of proper coupling between a transducer array and a patient's skin, renal artery blood flow imager, renal artery blood flow tracker, image stabilization and/or tracker that traces fiduciary and/or reference points in a body and/or placed on a body.

34. Apparatus for treating a kidney, modifying a kidney function, preventing a kidney dysfunction and/or preventing a deterioration of kidney function, the apparatus comprising:
   a. an energy source configured to deliver ultrasound energy towards at least a portion of said kidney;
   b. circuitry configured to perform at least one protocol to emit said ultrasound energy at a frequency, pulse shape, pulse duration, repetition rate and amplitude suitable to affect kidney function in at least a portion of said kidney;
   wherein said circuitry is further configured to deliver said ultrasound energy for at least 30 minutes while not inducing substantial thermal damage or cavitation damage to tissues in the patient's kidney;
   wherein said frequency of most of said ultrasound energy is at a frequency higher than 5 Megahertz (MHZ);
   wherein said circuitry is further configured to emit said quantity of ultrasound energy at a mechanical index below 1.0.

35. The apparatus according to claim 34, comprising:
   at least one transducer configured to be acoustically coupled to a tissue and configured to deliver said ultrasound energy towards said at least a portion of said kidney; and
   said circuitry for powering said at least one transducer with a waveform and power and duration causing said ultrasound energy to positively affect said kidney function in said at least a portion of said kidney.

36. The apparatus according to claim 35, wherein said at least one transducer comprises a plurality of flexibly interconnected transducers.

37. The apparatus according to claim 35, wherein said at least one transducer comprises a phased array.

38. The apparatus according to claim 35, wherein said at least one transducer comprises a beam-forming transducer.

39. The apparatus according to claim 35, wherein said at least one transducer is incorporated in an endoscopy device.

40. The apparatus according to claim 34, comprising at least one sensor and wherein said circuitry modifies said powering according to a signal from said sensor.

41. The apparatus according to claim 40, wherein said circuitry automatically moves and orients said ultrasound energy to kidney regions relative to a location of a renal artery according to a signal provided by said at least one sensor.

42. The apparatus according to claim 34, wherein said apparatus is implantable in the body of the user.

43. The apparatus according to claim 34, wherein said circuitry comprises instructions for monitoring said delivered ultrasound energy for avoiding inducing substantial thermal effect or cavitation effect to the patient's kidney.

44. The apparatus according to claim 34, wherein said at least one protocol is designed to not inducing substantial thermal effect or cavitation effect to the patient's tissue.

45. The apparatus according to claim 34, wherein said circuitry is further configured to deliver said ultrasound energy as a continuous waveform of energy.

46. The apparatus according to claim 45, wherein said continuous waveform of energy is delivered for at least 1 hour.

47. The apparatus according to claim 34, wherein said apparatus is integrated with an imaging system.

48. The apparatus according to claim 34, further comprising a coupling element configured to anatomically fit with body curvatures of a patient and provide acoustic coupling between at least one transducer and a skin of said patient, comprising:
 a. at least one acoustically coupling material;
 b. at least one holding structure configured to hold said at least one acoustically coupling material;
 wherein said coupling element comprises at least one sensor adapted to provide feedback to at least one controller unit, said at least one controller unit controls said transducer.

49. The apparatus according to claim 48, wherein said at least one acoustically coupling material comprises at least one selected from the group consisting of gel, gel pad, fluid, fluid container, polymer layer and any combination thereof.

50. The apparatus according to claim 48, wherein said at least one holding structure is selected form a group consisting of a mattress, a sticker, a belt, a holder, and any combination thereof.

51. The apparatus according to claim 48, wherein said coupling element is disposable.

52. The apparatus according to claim 48, wherein said at least one sensor is a pressure sensor for monitoring a pressure applied by said coupling element on said skin of said patient.

53. The apparatus according to claim 48, wherein said at least one sensor is a pressure sensor for monitoring a pressure applied by said transducer on said skin of said patient.

54. The apparatus according to claim 48, wherein said at least one sensor is for monitoring a movement performed by said patient.

55. The apparatus according to claim 34, wherein said apparatus comprises at least one sensor is selected from a group consisting of a cavitation detector, ultrasonic coupling meter, ultrasonic impedance meter a blood pressure meter, heart rate meter, temperature sensor, vital signs monitor, ECG, SpO2, water/saline/fluid intake, urine flow meter, or a meter of the presence of blood or proteins in the urine, and any combination thereof.

56. The apparatus according to claim 34, wherein said apparatus utilizes information of location of tissues in the kidney and/or in the vicinity of the kidney for the activation and/or deactivation of the apparatus in the kidney.

57. The apparatus according to claim 34, wherein said type of information comprises one or more of estimation of distance to said kidney, Doppler effect flow velocities within a sonicated space, organ edge detection, automatic organ classification, detection of gas/air pockets in different organs, detection of lack of proper coupling between a transducer array and a patient's skin, renal artery blood flow imager, renal artery blood flow tracker, image stabilization and/or tracker that traces fiduciary and/or reference points in a body and/or placed on a body.

* * * * *